United States Patent
Li et al.

(10) Patent No.: US 11,788,118 B2
(45) Date of Patent: Oct. 17, 2023

(54) METHOD FOR DETECTING TARGET NUCLEIC ACID SEQUENCES

(71) Applicant: XIAMEN ZEESAN BIOTECH CO., LTD., Xiamen (CN)

(72) Inventors: Qingge Li, Xiamen (CN); Dongmei Chen, Xiamen (CN); Qiuying Huang, Xiamen (CN); Ye Xu, Xiamen (CN); Yiqun Liao, Xiamen (CN)

(73) Assignee: XIAMEN ZEESAN BIOTECH CO., LTD., Xiamen (CN)

( * ) Notice: Subject to any disclaimer, the term of this patent is extended or adjusted under 35 U.S.C. 154(b) by 178 days.

(21) Appl. No.: 17/392,027

(22) Filed: Aug. 2, 2021

(65) Prior Publication Data

US 2022/0017949 A1    Jan. 20, 2022

Related U.S. Application Data

(62) Division of application No. 16/327,256, filed as application No. PCT/CN2018/084794 on Apr. 27, 2018, now Pat. No. 11,111,522.

(30) Foreign Application Priority Data

Apr. 28, 2017    (CN) .......................... 201710299957.4

(51) Int. Cl.
  *C12Q 1/68* (2018.01)
  *C12Q 1/6818* (2018.01)
  *C12N 15/11* (2006.01)

(52) U.S. Cl.
  CPC ............ *C12Q 1/6818* (2013.01); *C12N 15/11* (2013.01); *C12Q 2527/107* (2013.01); *C12Q 2531/113* (2013.01); *C12Q 2537/143* (2013.01); *C12Q 2563/107* (2013.01)

(58) Field of Classification Search
  None
  See application file for complete search history.

(56) References Cited

U.S. PATENT DOCUMENTS

| | | |
|---|---|---|
| 2013/0109588 A1 | 5/2013 | Chun et al. |
| 2014/0057264 A1 | 2/2014 | Chun et al. |
| 2014/0315747 A1 | 10/2014 | Roth et al. |
| 2015/0072887 A1 | 3/2015 | Chun et al. |

FOREIGN PATENT DOCUMENTS

| | | |
|---|---|---|
| JP | 2014533107 A | 12/2014 |
| KR | 20120081482 A | 7/2012 |
| WO | WO 2016/025452 A1 | 2/2016 |

OTHER PUBLICATIONS

Faltin et al. Clinical Chemistry 2012 58:11 pp. 1546-1556. (Year: 2012).*
Jong-Yoon et al. High Multiplex Molecular Diagnostics Seegene Bulletin 2012 vol. 12 pp. 1-4 (Year: 2012).*
Faltin et al., "Mediator Probe PCR: A Novel Approach for Detection of Real-Time PCR Based on Label-Free Primary Probes and Standardized Secondary Universal Fluorogenic Reporters", Clinical Chemistry, 2012, 58(11): 1546-1556.
Wadle et al., "Simplified development of multiplex real-time PCR through master mix augmented by universal fluorogenic reporters", Biotechniques, 2016, 61(3): 123-128.
International Search Report issued for International Application No. PCT/CN2018/084794, dated Jul. 18, 2018.
Chun et al., "High Multiplex Molecular Diagnostics", Seegene Bulletin, Jul. 2012, vol. 1, pp. 1-4.

* cited by examiner

*Primary Examiner* — Juliet C Switzer
(74) *Attorney, Agent, or Firm* — James S. Keddie; Bozicevic, Field & Francis LLP

(57) ABSTRACT

The present application relates to multiplex detection of nucleic acid molecules. In particular, the present application provides a method for detecting target nucleic acid sequences, said method can simultaneously detect the presence of multiple target nucleic acid sequences in a sample. In addition, the present application further provides a probe set, and a kit comprising one or more said probe sets, said probe set and said kit can be used to carry out the method of the invention.

20 Claims, 8 Drawing Sheets

Specification includes a Sequence Listing.

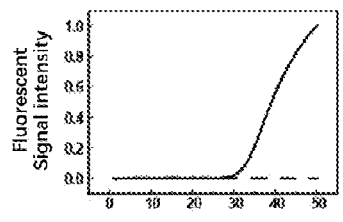 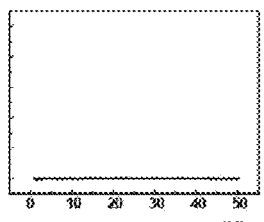 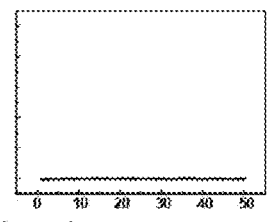 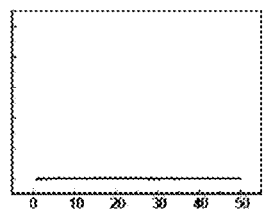
Fig. 2A  Fig. 2B  Fig. 2C  Fig. 2D
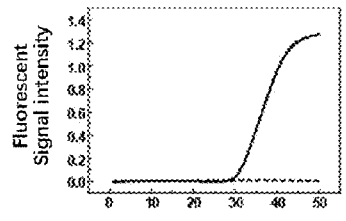 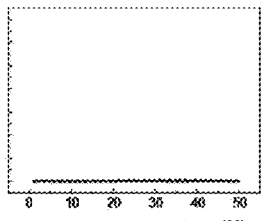 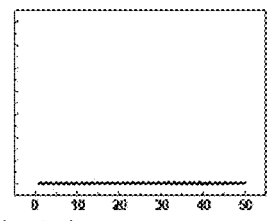 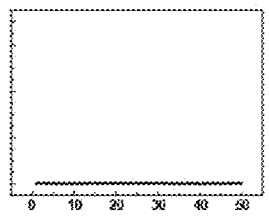
Fig. 3A  Fig. 3B  Fig. 3C  Fig. 3D
Fig. 4A
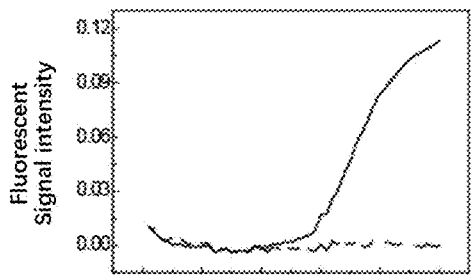 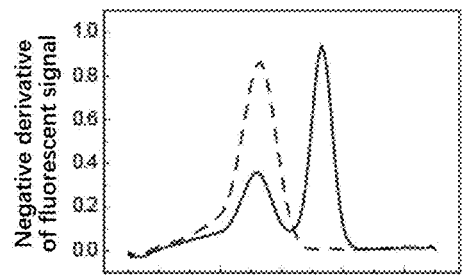
Fig. 4B
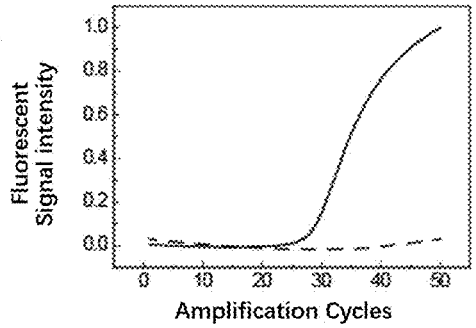 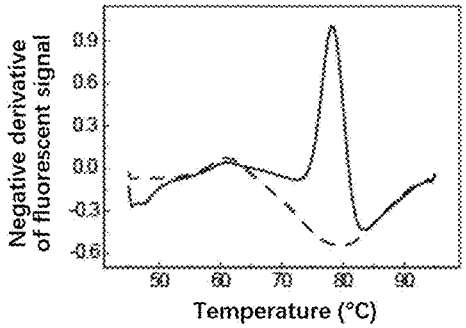

Amplification Cycles    Temperature (°C)

Amplification Cycles

Temperature (°C)

Figs. 9A
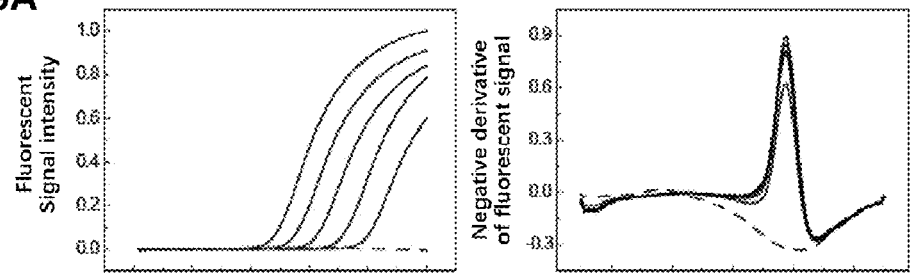
Fig. 9B
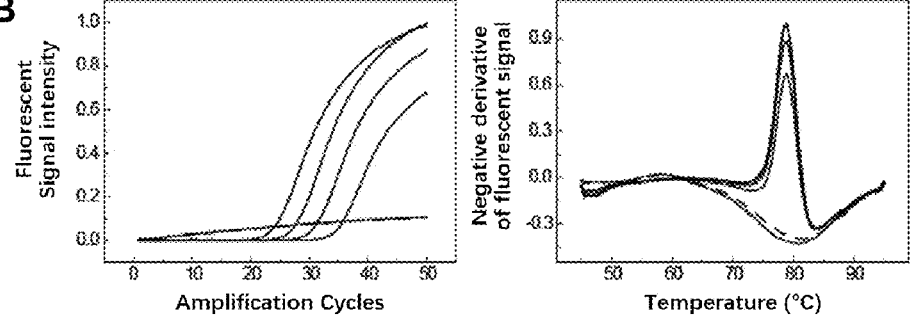
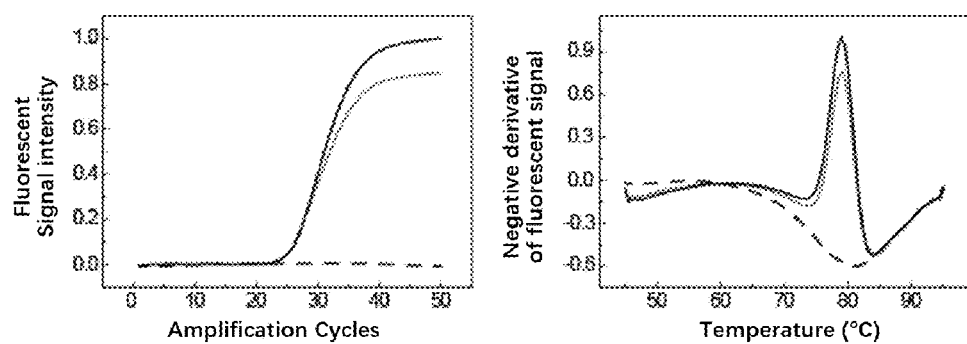
Fig. 10
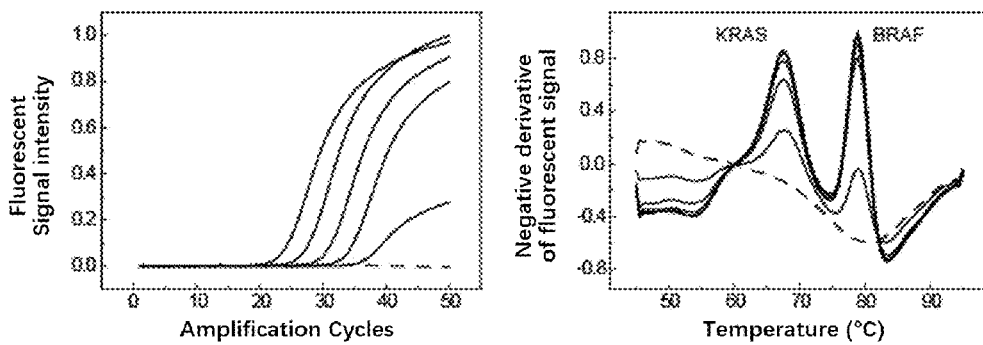
Fig. 11

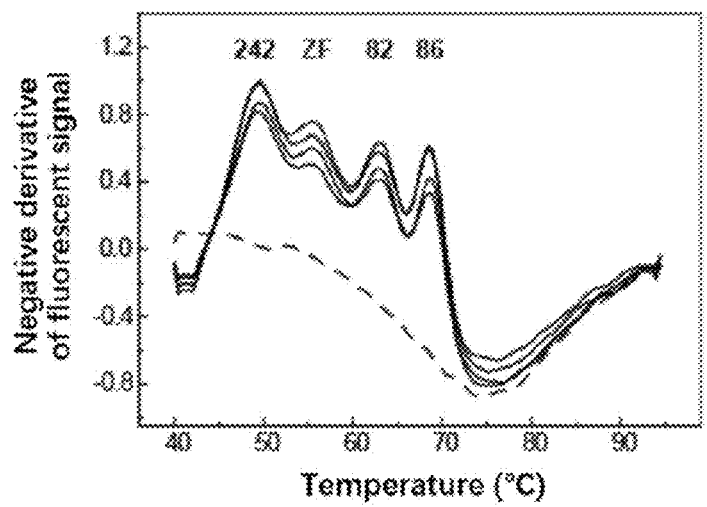
Fig. 12
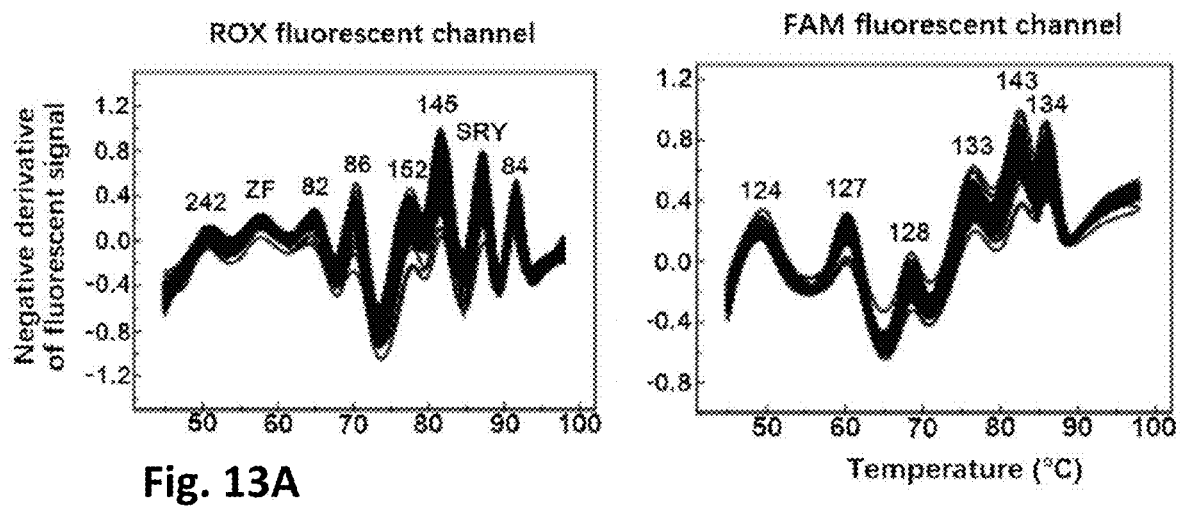
Fig. 13A
Fig. 13B
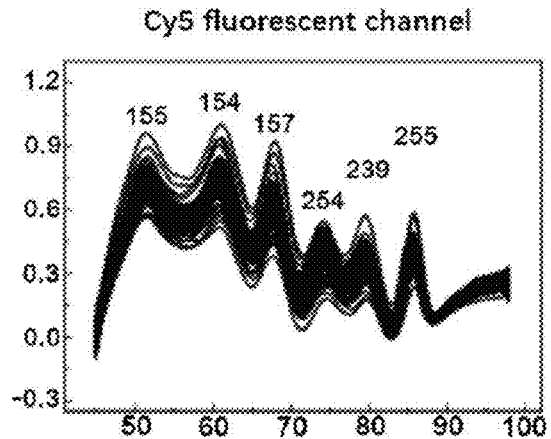
Fig. 13C

METHOD FOR DETECTING TARGET NUCLEIC ACID SEQUENCES

CROSS-REFERENCE TO RELATED APPLICATIONS

This application is a divisional of Ser. No. 16/327,256, filed on Feb. 21, 2019, which is a § 371 national phase of International Application No. PCT/CN2018/084794, filed on Apr. 27, 2018, which claims the benefit of Chinese Patent Application No. 201710299957.4, filed on Apr. 28, 2017, which applications are incorporated by reference herein.

TECHNICAL FIELD

The present application relates to multiplex detection of nucleic acid molecules. In particular, the present application provides a method for detecting target nucleic acid sequences, said method can simultaneously detect the presence of multiple target nucleic acid sequences in a sample. In addition, the present application further provides a probe set, and a kit comprising one or more said probe sets, said probe set and kit can be used to carry out the method of the invention.

BACKGROUND ART

Real-time PCR is a common method for detecting nucleic acids, which is operated easily and used widely. Moreover, by using multiplex real-time PCR, multiple target sequences can be detected simultaneously in a single reaction tube, which not only improves detection efficiency, but also reduces cost.

In real-time PCR methods, target sequences can be detected by using fluorophore-labeled oligonucleotide probes. In general, a fluorophore-labeled probe specifically binds to the target sequence between two primers for PCR amplification, so as to avoid the interference signal resulted from the nonspecific amplification of the primer dimer, and enhance the specificity of the detection result. For multiplex real-time PCR, when multiple oligonucleotide probes specific for target sequences are used, each oligonucleotide probe can be labeled with a different fluorophore group. Therefore, by detecting the unique fluorescent signal carried by each probe, the target sequence specifically recognized by each probe can be detected. In real-time PCR methods, a target sequence can be detected by two modes, i.e. real-time detection mode and melting curve analysis after amplification (also called post-PCR MCA mode). In the real-time detection mode, the detection and PCR amplification of a target sequence are carried out simultaneously, without additional steps. Therefore, the real-time detection mode is simple and direct. However, the maximal number of target sequences, which can be detected in a single-round detection in such a mode, is restricted by the number of fluorescent detection channels in a real-time PCR instrument, generally no more than 6. In the MCA mode, an additional step has to be carried out after PCR amplification, i.e., analyzing the melting point of the duplex formed by a probe and a target sequence. In the MCA mode, a target sequence can be recognized or distinguished by fluorescent color and/or melting point. Therefore, although MCA mode is relatively complicated (i.e. an additional step is needed), the maximal number of target sequences, which can be detected in a single-round detection, is increased.

However, there are also some problems in fluorescent probe-based detection in multiplex real-time PCR. Firstly, the preparation of fluorescent probes involves complicated chemical modification and purification process, and the preparation cost is much higher than that of non-labeled probes. Therefore, use of multiple fluorescent probes will increase the detection cost. Secondly, in a multiplex real-time PCR method, the co-existence of multiple fluorescent probes can increase the background fluorescence of a reaction system, which will further result in a decrease of detection sensitivity. Therefore, multiplex real-time PCR method needs to be improved, in order to detect as many target sequences as possible by using as few fluorescent probes as possible.

Faltin et al. (Clinical Chemistry 2012, 58(11): 1546-1556) describes a "mediator probe"-based real-time PCR detection method. In traditional real-time PCR detection methods, a fluorescent probe specific for a target sequence is needed for each target sequence. However, in the method as reported by Faltin et al., two probes are needed for each target sequence: a non-fluorescently labeled mediator probe specific for a target sequence, and another fluorescently labeled probe (a fluorescent probe) that does not bind to a target sequence; wherein, the mediator probe consists of a target-specific sequence at 3'-end and a tag sequence (mediator) at 5'-end; the fluorescent probe consists of a single-stranded sequence at 3'-end comprising a mediator hybridization site, and a sequence at 5'-end comprising a quencher group and a fluorescent group and having a hairpin structure, wherein both the quencher group and the fluorescent group are located at the arms of the hairpin structure and are close to each other, and therefore fluorescence quenching can occur. During PCR, a mediator probe binds to a target sequence via its target specific sequence, and its tag sequence (mediator) at 5'-end retains single-stranded and free; and then the mediator probe is enzymatically cleaved in the presence of DNA polymerase having 5'-nuclease activity, to release a mediator carrying 3'-OH. The released mediator binds to the mediator hybridization site on the fluorescent probe, and is extended by the polymerase, so that the sequence labeled with a quencher group is cleaved off or replaced, and the fluorescent group is separated from the quencher group, resulting in an enhanced fluorescent intensity.

The method described by Faltin et al. is characterized in that the generation of a fluorescent signal depends on two probes: a mediator probe and a fluorescent probe; wherein, the mediator probe is used as a hybridization probe, which is not fluorescently labeled; the fluorescent probe is used to generate a fluorescent signal, which specifically binds to a mediator, but does not bind to a target sequence. In this method, the fluorescent probe can be used as a common probe. For example, when a singleplex real-time PCR is used to detect multiple target sequences, an identical fluorescent probe, and multiple mediator probes, each of which carries a unique target-specific sequence but comprises the same mediator sequence, can be used to carry out the PCR. In addition, for multiplex real-time PCR, when it does not need to recognize or distinguish each of target sequences, the screening of multiple target sequences can also be achieved by using a fluorescent probe and multiple mediator probes having the same mediator sequence. As compared with traditional real-time PCR methods, the method of Faltin et al. can detect multiple target sequences by using a common fluorescent probe, without synthesizing a unique fluorescent probe for each target sequence, which significantly reduces the detection cost.

However, the method of Faltin et al. has obvious defects. Particularly, when the method of Faltin et al. is used to carry out multiplex real-time PCR in which each target sequence needs to be distinguished, for each target sequence, it needs to design a mediator probe carrying a target specific sequence and a corresponding fluorescent probe carrying a unique fluorescent signal. In such a case, as compared with traditional multiplex real-time PCR in which a single probe is used for each target sequence, the method of Faltin et al. needs double number of probes. Correspondingly, the whole reaction system becomes more complicated, and the detection cost also becomes higher. For example, Faltin et al. disclose a duplex PCR method for simultaneous detection of HPV18 and human ACTB gene, in which 2 mediator probes and 2 fluorescent probes were used; by contrast, a traditional duplex real-time PCR method only needs 2 fluorescent probes. Similar examples can also be found in Wadle S et al. (Biotechniques 2016, 61 (3):123-8), which describes a pentaplex PCR system that uses 5 mediator probes and 5 fluorescent reporter probes in total. By contrast, in a traditional pentaplex real-time PCR method, only 5 fluorescent probes are needed. In such a case, as compared with a traditional multiplex real-time PCR, the method of Faltin et al. is more complicated and costly.

US 2013/0109588 A1 discloses a real-time PCR assay for melting curve analysis, which is similar to the method of Faltin et al., and achieves the detection of a target sequence by two probes (PTO probe, which corresponds to the mediator probe; and CTO probe, which corresponds to the fluorescent probe). Correspondingly, the method in US 2013/0109588 A1 has similar advantages and disadvantages as compared to the method of Faltin et al. Particularly, when the method described in the patent application is used to carry out a multiplex real-time PCR in which each target sequence needs to be distinguished, it needs to design a PTO probe and a CTO probe for each target sequence; i.e. double number of probes are used. For example, the patent application describes a duplex real-time PCR for simultaneous detection of Neisseria gonorrhoeae and Staphylococcus aureus, in which 2 PTO probes and 2 CTO probes are used. In such a case, as compared with a traditional multiplex real-time PCR in which a single probe is used for each target sequence, the method in US 2013/0109588 A1 is more complicated and costly.

US 2014/0057264 A1 discloses another real-time PCR method using two probes. In the method, the fluorescent signal is generated due to the cleavage of the labeled probe, and therefore, the method can only be used in real-time detection mode, instead of MCA mode. In addition, similar to the method of Faltin et al., when the method described in US 2014/0057264 A1 is used to carry out multiplex real-time PCR in which each target sequence needs to be distinguished, it needs to design 2 probes for each target sequence, which makes the reaction system more complicated and costly.

US 2015/0072887 A1 discloses a real-time PCR assay useful for melting curve analysis, in which the detection of a target sequence is achieved by three probes. However, when the method described in the patent application is used to carry out a multiplex real-time PCR in which each target sequence needs to be distinguished, it needs to design 3 probes for each target sequence, which makes the reaction system more complicated and costly. Similar real-time PCR assays using 3 probes are also disclosed in US 2015/0167060 A1 and US 2016/0060690 A1. However, these methods are similar to the methods as disclosed in US 2015/0072887 A1, and when they are used to carry out a multiplex real-time PCR in which each target sequence needs to be distinguished, they are more complicated and costly than the traditional real-time PCR method.

In general, as compared with traditional real-time PCR methods, the improved real-time PCR methods using two or three probes (e.g. the method of Faltin et al.) have significant advantages when carrying out a singleplex real-time PCR or a multiplex real-time PCR without the need of recognizing or distinguishing each target sequence: i.e. multiple mediator probes carrying the same mediator sequence but different target specific sequences, and a common fluorescent probe can be used so as to significantly reduce the detection cost. However, when carrying out a multiplex real-time PCR in which each target sequence needs to be distinguished, these improved real-time PCR methods need to use double or even triple number of probes, and instead, it is more complicated and costly than the traditional real-time PCR method.

Therefore, new real-time PCR detection methods need to be developed, so as to carry out a multiplex real-time PCR with the need of distinguishing each target sequence in a simpler reaction system, at a lower detection cost.

In the application, unless otherwise specified, the scientific and technical terms used herein have the meanings as commonly understood by those skilled in the art. Moreover, the laboratory operations of nucleic acid chemistry used herein are the conventional operations widely used in the corresponding fields. Meanwhile, in order to better understand the invention, definitions and explanations of the related terms are provided below.

As used herein, the terms "target nucleic acid sequence", "target nucleic acid" and "target sequence" refer to a nucleic acid sequence of interest to be detected. In the present application, the terms "a target nucleic acid sequence", "target nucleic acid" an "target sequence" have the same meaning and can be used interchangeably.

As used herein, the term "mediator probe" refers to a single-stranded nucleic acid molecule comprising in 5' to 3' direction, a mediator sequence and a targeting sequence (i.e. a target-specific sequence). In the present application, a mediator sequence does not comprise a sequence complementary to a target nucleic acid sequence, a target specific sequence comprises a sequence complementary to a target nucleic acid sequence. Therefore, under conditions that allow nucleic acid hybridization, annealing or amplification, a mediator probe hybridizes or anneals with a target nucleic acid sequence via a target specific sequence (i.e. forming a double-stranded structure), and the mediator sequence in a mediator probe does not hybridize with said target nucleic acid sequence, and is in a free state (i.e. retaining a single-stranded structure).

As used herein, the terms "targeting sequence", "target-specific sequence" and "target specific sequence" refer to a sequence that can selectively/specifically hybridize or anneal with a target nucleic acid sequence under conditions that allow nucleic acid hybridization, annealing or amplification, and comprises a sequence complementary to a target nucleic acid sequence. In the present application, the terms "targeting sequence", "target-specific sequence" and "target specific sequence" have the same meaning and can be used interchangeably. It is easy to understand that a targeting sequence or a target specific sequence is specific for a target nucleic acid sequence. In other words, under conditions that allow nucleic acid hybridization, annealing or amplification, a targeting sequence or a target specific sequence only hybridizes or anneals with a specific target nucleic acid sequence, but does not hybridize or anneal with other nucleic acid sequences.

As used herein, the term "mediator sequence" refers to an oligonucleotide sequence in a mediator probe, which is not complementary to a target nucleic acid sequence, and is located upstream (5' end) to a target specific sequence. In the present application, for each target nucleic acid sequence, a unique mediator probe is designed or provided, which has a unique mediator sequence (in other words, the mediator sequences in all the mediator probes used are different from each other); therefore, each target nucleic acid sequence corresponds to a unique mediator probe (a unique mediator sequence). Therefore, by detecting said unique mediator sequence, the target nucleic acid sequence corresponding thereto can be detected.

As used herein, the term "upstream oligonucleotide sequence" refers to an oligonucleotide sequence comprising a sequence complementary to a target nucleic acid sequence, which, under the conditions that allow nucleic acid hybridization (or annealing) or amplification, can hybridize (or anneal) with a target nucleic acid sequence, and, when hybridizing with a target nucleic acid sequence, is located upstream of a mediator probe.

As used herein, the term "complementary" means that hydrogen bonds can be formed between two nucleic acid sequences based on the principle of complementary base pairing (Waston-Crick principle), and therefore a duplex can be formed. In the present application, the term "complementary" includes "substantially complementary" and "completely complementary". As used herein, the term "completely complementary" means that each base in a nucleic acid sequence can be paired with a base in another nucleic acid strand, with no mismatches or gaps. As used herein, the term "substantially complementary" means that most of the bases in a nucleic acid sequence can be paired with the bases in another nucleic acid strand, and mismatches or gaps are allowed (e.g. one or more nucleotides mismatches or gaps can be present). In general, under conditions that allow nucleic acid hybridization, annealing or amplification, two "complementary" (e.g. substantially complementary or completely complementary) nucleic acid sequences will selectively or specifically hybridize or anneal with each other, to form a duplex. For example, in the present application, an upstream oligonucleotide sequence and the target specific sequence in a mediator probe each comprise a sequence complementary (e.g. substantially complementary or completely complementary) to a target nucleic acid sequence. Therefore, under conditions that allow nucleic acid hybridization, annealing or amplification, an upstream oligonucleotide sequence and the target specific sequence in a mediator probe will selectively/specifically hybridize or anneal with a target nucleic acid sequence. Correspondingly, the term "not complementary" means that two nucleic acid sequences, under conditions that allow nucleic acid hybridization, annealing or amplification, cannot hybridize or anneal with each other, and cannot form a duplex. For example, in the present application, a mediator sequence comprises a sequence not complementary to a target nucleic acid sequence. Therefore, under conditions that allow nucleic acid hybridization, annealing or amplification, a mediator sequence does not hybridize or anneal, and cannot form a duplex, with a target nucleic acid sequence, and is in a free state (i.e. retaining a single-stranded structure).

As used herein, the terms "hybridize/hybridization" and "anneal/annealing" refer to the process of forming a double-stranded nucleic acid by complementary single-stranded nucleic acid molecules. In the present application, "hybridize/hybridization" and "anneal/annealing" have the same meaning and can be used interchangeably. Generally, two completely complementary or substantially complementary nucleic acid sequences can hybridize or anneal with each other. The complementarity of two nucleic acid sequences required for hybridization or annealing depends on the hybridization conditions as used, particularly temperature.

As used herein, the expression "conditions that allow nucleic acid hybridization" has the meanings as commonly understood by a person skilled in the art and can be determined by conventional methods. For example, two nucleic acid molecules having complementary sequences can hybridize with each other under suitable hybridization conditions. Such hybridization conditions may relate to the following factors: temperature, pH value, components and ionic strength of a hybridization buffer, etc.; and can be determined according to the length and GC content of two complementary nucleic acid molecules. For example, when two complementary nucleic acid molecules have a relatively short length and/or a relatively low GC content, low stringent hybridization conditions can be used. When two complementary nucleic acid molecules have a relatively long length and/or a relatively high GC content, high stringent hybridization conditions can be used. Such hybridization conditions are well known by a person skilled in the art (see, for example, Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999). In the present application, the terms "hybridize/hybridization" and "anneal/annealing" have the same meanings and can be used interchangeably. Correspondingly, the expressions "conditions that allow nucleic acid hybridization" and "conditions that allow nucleic acid annealing" also have the same meanings and can be used interchangeably.

As used herein, the expression "conditions that allow nucleic acid amplification", which has the meanings commonly understood by a person skilled in the art, refers to the conditions that allow a nucleic acid polymerase (e.g. DNA polymerase) to use a nucleic acid strand as a template to synthesize another nucleic acid strand, and form a duplex. Such conditions are well known by a person skilled in the art, and may relate to the following factors: temperature, pH value, components, concentration and ionic strength of a hybridization buffer, etc. Suitable nucleic acid amplification conditions can be determined by conventional methods (see, for example, Joseph Sambrook, et al., Molecular Cloning, A Laboratory Manual, Cold Spring Harbor Laboratory Press, Cold Spring Harbor, N.Y. (2001)). In the method of the invention, "conditions that allow nucleic acid amplification" are preferably the working conditions of a nucleic acid polymerase (e.g. DNA polymerase).

As used herein, the expression "conditions that allow extension reaction of a nucleic acid polymerase", which has the meanings commonly understood by a person skilled in the art, refers to the conditions that allow a nucleic acid polymerase (e.g. DNA polymerase) to use a nucleic acid strand as a template to extend another nucleic acid strand (e.g. a primer or a probe), and form a duplex. Such conditions are well known by a person skilled in the art, and may relate to the following factors: temperature, pH value, components, concentration and ionic strength of a hybridization buffer, etc. Suitable nucleic acid amplification conditions can be determined by conventional methods (see, for example, Joseph Sambrook, et al., Molecular Cloning, A Laboratory Manual, Cold Spring Harbor Laboratory Press, Cold Spring Harbor, N.Y. (2001)). In the method of the invention, "conditions that allow extension reaction of a nucleic acid polymerase" are preferably the working conditions of a nucleic acid polymerase (e.g. DNA polymerase).

In the present application, the expression "conditions that allow extension reaction of a nucleic acid polymerase" and "conditions that allow nucleic acid extension" have the same meanings and can be used interchangeably.

As used herein, the expression "conditions that allow cleavage of mediator probes" refers to the conditions that allow an enzyme having 5' nuclease activity to cleave a mediator probe hybridized to a target nucleic acid sequence, and release a nucleic acid fragment comprising a mediator sequence or a part thereof. In the method of the invention, conditions that allow cleavage of mediator probes are preferably working conditions of an enzyme having 5' nuclease activity. For example, when the enzyme having 5' nuclease activity used is a nucleic acid polymerase having 5' nuclease activity, the conditions that allow cleavage of mediator probes may be working conditions of said nucleic acid polymerase.

The workings conditions of various enzymes can be determined by a person skilled in the art through conventional methods, and can generally relate to the following factors: temperature, pH value, components, concentrations and ionic strength of a buffer, etc. Alternatively, conditions recommended by the manufacturer of enzymes can be used.

As used herein, the term "nucleic acid denaturation", which has the meanings commonly understood by a person skilled in the art, refers to the process of dissociating a double-stranded nucleic acid molecule into single strands. The expression "conditions that allow nucleic acid denaturation" refers to the conditions that allow dissociation of a double-stranded nucleic acid molecules into single strands. Such conditions can be determined conventionally by a person skilled in the art (see, for example, Joseph Sambrook, et al., Molecular Cloning, A Laboratory Manual, Cold Spring Harbor Laboratory Press, Cold Spring Harbor, N.Y. (2001)). For example, nucleic acid denaturation can be carried out by conventional technologies such as heating, alkaline treatment, urea treatment, and enzymatic methods (e.g. methods using helicase). In the present application, nucleic acids are preferably denatured under heating conditions. For example, nucleic acids can be denatured by heating to 80-105° C.

As used herein, the term "upstream" is used to describe the relative position of two nucleic acid sequences (or two nucleic acid molecules), and has the meanings commonly understood by a person skilled in the art. For example, the expression "a nucleic acid sequence is located upstream to another nucleic acid sequence" means that when arranged in 5' to 3' direction, the former is located a position closer to the front (i.e. a position closer to 5' end) as compared to the latter. As used herein, the meaning of the term "downstream" is opposite to that of the term "upstream".

As used herein, the term "fluorescent probe" refers to an oligonucleotide that carries a fluorescent group and can generate fluorescent signal. In the present application, a fluorescent probe can be used as a detection probe.

As used herein, the term "melting curve analysis" has the meanings commonly understood by a person skilled in the art, and refers to a method for analyzing the presence or identity of a double-stranded nucleic acid molecule by having the melting curve of the double-stranded nucleic acid molecule, and is generally used to evaluate the dissociation characteristics of double-stranded nucleic acid molecules. Methods for carrying out melting curve analysis are well known by a person skilled in the art (see, for example, The Journal of Molecular Diagnostics 2009, 11 (2): 93-101). In the present application, the term "melting curve analysis" and the term "melting analysis" have the same meaning and can be used interchangeably.

In some preferred embodiments of the present application, a detection probe labeled with a reporter group and a quencher group can be used to carry out melting curve analysis. In brief, at an ambient temperature, a detection probe and its complementary sequence can form a duplex by virtue of base pairing. In this case, the reporter group (e.g. a fluorescent group) and the quencher group on the detection probe are separated from each other, the quencher group cannot absorb the signal generated by the reporter group (e.g. a fluorescent signal), and the signal (e.g. a fluorescent signal) can be detected. With the increase of temperature, the two strands of the duplex begin to dissociate (i.e. the detection probe is gradually dissociated from its complementary sequence), and the dissociated detection probe is in a single-stranded and randomly coiled state. In this case, the reporter group (e.g. a fluorescent group) and the quencher group on the dissociated detection probe are close to each other, and therefore the signal (e.g. a fluorescent signal) generated by the reporter group (e.g. a fluorescent group) is absorbed by the quencher group. Therefore, with the increase of temperature, the detected signal (e.g. a fluorescent signal) gradually weakens. When the two strands of the duplex are completely dissociated, all the detection probes are in a single-stranded and randomly coiled state. In this case, the signals (e.g. fluorescent signals) generated by the reporter groups (e.g. fluorescent groups) on all the detection probes are absorbed by the quencher groups. Therefore, the signals (e.g. fluorescent signals) generated by the reporter groups (e.g. fluorescent groups) cannot be detected substantively. Therefore, by detecting the signal (e.g. a fluorescent signal) generated by a duplex comprising a detection probe during heating or cooling, the hybridization and dissociation process of a detection probe and its complementary sequence can be observed, and a curve, in which the signal intensity changes with a change in temperature, is formed. Further, by derivation analysis of the obtained curve, a curve (i.e. the melting curve of the duplex), in which the rate of change in signal intensity is used as the ordinate and the temperature is used as the abscissa, can be obtained. The peak in the melting curve is the melting peak, and the temperature corresponding to the peak it is the melting point ($T_m$ value) of said duplex. In general, the higher the matching degree between a detection probe and its complementary sequence is (e.g. fewer bases are mismatched, and more bases are paired), the higher the $T_m$ value of a duplex is. Therefore, by detecting the $T_m$ value of a duplex, the presence and identity of the sequence complementary to the detection probe in the duplex can be determined. As used herein, the term "melting peak", "melting point" and "$T_m$ value" have the same meaning and can be used interchangeably.

Detection Method

Therefore, in an aspect, the invention provides a method for detecting the presence of at least two target nucleic acid sequences in a sample, comprising the following steps:

(1) under a condition that allows nucleic acid hybridization, contacting said sample with a first upstream oligonucleotide sequence, a first mediator probe, a second upstream oligonucleotide sequence and a second mediator probe, wherein, (i) said first upstream oligonucleotide sequence comprising a sequence complementary to a first target nucleic acid sequence; and, said first mediator probe comprising in 5' to 3' direction, a first mediator sequence and a first target specific sequence, wherein, said first mediator sequence comprises a sequence not complementary to the first target nucleic acid sequence, and, said first target specific sequence comprises a sequence complementary to the first target nucleic acid sequence; and, when hybridizing with the first target nucleic acid sequence, the first upstream oligonucleotide sequence is located upstream of the first target specific sequence;

(ii) said second upstream oligonucleotide sequence comprises a sequence complementary to a second target nucleic acid sequence; and, said second mediator probe comprising in 5' to 3' direction, a second mediator sequence and a second target specific sequence, wherein, said second mediator sequence comprises a sequence not complementary to the second target nucleic acid sequence, and, said second target specific sequence comprises a sequence complementary to the second target nucleic acid sequence; and, when hybridizing with the second target nucleic acid sequence, the second upstream oligonucleotide sequence is located upstream of the second target specific sequence; and, (iii) said first mediator sequence is different from said second mediator sequence; and, (2) under a condition that allows cleavage of mediator probes, contacting the product in Step (1) with an enzyme having 5' nuclease activity;

(3) under a condition that allows nucleic acid hybridization, contacting the product in Step (2) with a detection probe comprising in 3' to 5' direction, a first capture sequence complementary to the first mediator sequence or a part thereof, a second capture sequence complementary to the second mediator sequence or a part thereof, and a templating sequence; and, said detection probe is labeled with a reporter group and a quencher group, wherein, said reporter group can generate a signal, and, said quencher group can absorb or quench the signal generated by said reporter group; and, the signal, as generated by said detection probe when hybridizing with its complementary sequence, is different from the signal, as generated when not hybridizing with its complementary sequence;

(4) under a condition that allows extension reaction of a nucleic acid polymerase, contacting the product in Step (3) with a nucleic acid polymerase;

(5) subjecting the product in Step (4) to melting curve analysis; and according to the result of the melting curve analysis, determining whether said first target nucleic acid sequence and said second target nucleic acid sequence are present in said sample.

In Step (1) of the method of the invention, since said first upstream oligonucleotide sequence comprises a sequence complementary to the first target nucleic acid sequence, and said first target specific sequence comprises a sequence complementary to the first target nucleic acid sequence, when the first target nucleic acid sequence is present, both said first upstream oligonucleotide sequence and said first mediator probe hybridize with said first target nucleic acid sequence. Similarly, since said second upstream oligonucleotide sequence comprises a sequence complementary to the second target nucleic acid sequence, and said second target specific sequence comprises a sequence complementary to the second target nucleic acid sequence, when the second target nucleic acid sequence is present, both said second upstream oligonucleotide sequence and said second mediator probe hybridize with said second target nucleic acid sequence.

In Step (2) of the method of the invention, when the first target nucleic acid sequence is present, both said first upstream oligonucleotide sequence and said first mediator probe hybridize with said first target nucleic acid sequence. Further, since said first mediator sequence comprises a sequence not complementary to the first target nucleic acid sequence, the first mediator sequence in the first mediator probe is in a free state, and does not hybridize with the first target nucleic acid sequence. In such a case, in the presence of an enzyme having 5' nuclease activity, the first mediator sequence or a part thereof is cleaved off from the first mediator probe hybridized with the first target nucleic acid sequence due to the presence of the first upstream oligonucleotide sequence or an extension product thereof, to form a first mediator fragment. Similarly, when the second target nucleic acid sequence is present, both the second upstream oligonucleotide sequence and the second mediator probe hybridize with the second target nucleic acid sequence, and the second mediator sequence in the second mediator probe is in a free state, and does not hybridize with the second target nucleic acid sequence. In such a case, in the presence of an enzyme having 5' nuclease activity, the second mediator sequence or a part thereof is cleaved off from the second mediator probe hybridized with the second target nucleic acid sequence due to the presence of the second upstream oligonucleotide sequence or an extension product thereof, to form a second mediator fragment.

In Step (3) of the method of the invention, when the first mediator fragment is present, since the first mediator fragment comprises the first mediator sequence or a part thereof, and the detection probe comprises a first capture sequence complementary to the first mediator sequence or a part thereof, said first mediator fragment hybridizes with said detection probe. Similarly, when the second mediator fragment is present, since the second mediator fragment comprises the second mediator sequence or a part thereof, and the detection probe comprises a second capture sequence complementary to the second mediator sequence or a part thereof, said second mediator fragment hybridizes with said detection probe.

In Step (4) of the method of the invention, when the first mediator fragment is present, since said first mediator fragment hybridizes with said detection probe, and said detection probe comprises an additional sequence (e.g. the templating sequence), a nucleic acid polymerase will use said detection probe as a template, to extend the first mediator fragment, and form a first duplex. Similarly, when the second mediator fragment is present, since said second mediator fragment hybridizes with said detection probe, and said detection probe comprises an additional sequence (e.g. the templating sequence), a nucleic acid polymerase will use said detection probe as a template, to extend the second mediator fragment, and form a second duplex.

In Step (5) of the method of the invention, when the first duplex is present, the melting peak corresponding to the first duplex can be detected. Therefore, by determining the presence or absence of the melting peak corresponding to the first duplex, it can be determined that the first target nucleic acid sequence is present or absent in said sample. For example, when the melting peak corresponding to the first duplex is detected or not, it is determined that the first target nucleic acid sequence is present or absent in said sample. Similarly, by determining the presence or absence of the melting peak corresponding to the second duplex, it can be determined that the second target nucleic acid sequence is present or absent in said sample. For example, when the melting peak corresponding to the second duplex is detected or not, it is determined that the second target nucleic acid sequence is present or absent in said sample.

Particularly, in the method of the invention, since the first mediator sequence used is different from the second mediator sequence used, the first mediator fragment formed has a sequence different from that of the second mediator fragment, and hybridizes to said detection probe at a different position. Therefore, the first duplex comprising the extension product of the first mediator fragment and the detection probe are different from the second duplex comprising the extension product of the second mediator fragment and the detection probe, in terms of structure (sequence). Correspondingly, the first duplex will have a melting point ($T_m$ value) different from that of the second duplex. Therefore, in melting curve analysis, the first duplex exhibits a melting peak different from that of the second duplex. Therefore, by determining the melting peak of the first duplex or the second duplex, the presence of the first target nucleic acid sequence or the second target nucleic acid sequence in a sample can be determined.

In addition, since the sequences of the first mediator sequence, the second mediator sequence and the detection probe are known or pre-determined, the melting points ($T_m$ values) of the first duplex and the second duplex can be calculated beforehand. Therefore, by determining the melting peak corresponding to the melting point ($T_m$ value) of the first duplex or the second duplex in melting curve analysis, the presence of the first target nucleic acid sequence or the second target nucleic acid sequence in the sample can be determined.

Based on the same principle as described above, by designing more mediator probes, the method of the invention can be used to detect more target nucleic acid sequences simultaneously. Therefore, in some preferred embodiments, in Step (1), in addition to the first upstream oligonucleotide sequence, the first mediator probe, the second upstream oligonucleotide sequence and the second mediator probe, under a condition that allows nucleic acid hybridization, said sample is further contacted with a third upstream oligonucleotide sequence and a third mediator probe, wherein, said third upstream oligonucleotide sequence comprises a sequence complementary to a third target nucleic acid sequence; and, said third mediator probe comprises in 5' to 3' direction a third mediator sequence and a third target specific sequence, wherein, said third mediator sequence comprises a sequence not complementary to the third target nucleic acid sequence, and, said third target specific sequence comprises a sequence complementary to the third target nucleic acid sequence;

and, when hybridizing with the third target nucleic acid sequence, the third upstream oligonucleotide sequence is located upstream of the third target specific sequence; and, said third mediator sequence is different from said first and second mediator sequence;

and, in Step (3), the detection probe used further comprises a third capture sequence complementary to the third mediator sequence or a part thereof, which is located downstream of said templating sequence.

In such embodiments, in Step (1), when the third target nucleic acid sequence is present, said third upstream oligonucleotide sequence and said third mediator probe hybridize with said third target nucleic acid sequence. Further, in Step (2), when the third target nucleic acid sequence is present, the third mediator sequence or a part thereof is cleaved off from the third mediator probe hybridized with the third target nucleic acid sequence due to the presence of the third upstream oligonucleotide sequence or an extension product thereof, to form a third mediator fragment. Further, in Steps (3) and (4), when the third mediator fragment is present, said third mediator fragment hybridizes with said detection probe, and, said nucleic acid polymerase will use said detection probe as a template, to extend the third mediator fragment, and form a third duplex. Further, in Step (5), when the melting peak corresponding to the third duplex is determined or not, it is determined that the third target nucleic acid sequence is present or absent in said sample.

Similarly, in the method of the invention, since the first, second and third mediator sequence used are different, the first mediator fragment, second mediator fragment and third mediator fragment formed have different sequences, and hybridize to said detection probe at different positions. Therefore, the first duplex comprising an extension product of the first mediator fragment and the detection probe, the second duplex comprising an extension product of the second mediator fragment and the detection probe, and the third duplex comprising an extension product of the third mediator fragment and the detection probe, are different from each other in terms of structure (sequence). Correspondingly, said first, second and third duplex have different melting points ($T_m$ values). Therefore, in melting curve analysis, said first, second and third duplex show three melting peaks that are distinguishable from each other. Therefore, by determining the melting peak of the first, second or third duplex, the presence of the first, second or third target nucleic acid sequence in said sample can be determined.

In addition, since the sequences of the first, second and third mediator sequence and the detection probe are known or predetermined, the melting points ($T_m$ values) of the first, second and third duplexes can be calculated beforehand. Therefore, by determining the melting peak corresponding to the melting point ($T_m$ value) of the first, second or third duplex in melting curve analysis, the presence of the first, a second or a third target nucleic acid sequence in the sample can be determined.

In some preferred embodiments, in Step (1), in addition to the first upstream oligonucleotide sequence, the first mediator probe, the second upstream oligonucleotide sequence, the second mediator probe, the third upstream oligonucleotide sequence and the third mediator probe, said sample is further contacted with a fourth upstream oligonucleotide sequence and a fourth mediator probe, wherein, said fourth upstream oligonucleotide sequence comprises a sequence complementary to the fourth target nucleic acid sequence; and, said fourth mediator probe comprising in 5' to 3' direction, a fourth mediator sequence and a fourth target specific sequence, wherein, said fourth mediator sequence comprises a sequence not complementary to the fourth target nucleic acid sequence, and, said fourth target specific sequence comprises a sequence complementary to the fourth target nucleic acid sequence;

and, when hybridizing with the fourth target nucleic acid sequence, the fourth upstream oligonucleotide sequence is located upstream of the fourth target specific sequence; and, said fourth mediator sequence is different from said first, second and third mediator sequence;

and, in Step (3), the detection probe used further comprises a fourth capture sequence complementary to the fourth mediator sequence or a part thereof, which is located downstream of said templating sequence.

In such embodiments, in Step (1), when the fourth target nucleic acid sequence is present, said fourth upstream oligonucleotide sequence and said fourth mediator probe hybridize with said fourth target nucleic acid sequence. Further, in Step (2), when the fourth target nucleic acid sequence is present, the fourth mediator sequence or a part thereof is cleaved off from the fourth mediator probe hybridized with the fourth target nucleic acid sequence due to the presence of the fourth upstream oligonucleotide sequence or an extension product thereof, to form a fourth mediator fragment. Further, in Steps (3) and (4), when the fourth mediator fragment is present, said fourth mediator fragment hybridizes with said detection probe, and, said nucleic acid polymerase will use said detection probe as a template, to extend the fourth mediator fragment, and form a fourth duplex. Further, in Step (5), when the melting peak corresponding to the fourth duplex is detected or not, it is determined that the fourth target nucleic acid sequence is present or absent in said sample.

Similarly, in the method of the invention, since the first, second, third and fourth mediator sequence used are different, the first mediator fragment, the second mediator fragment, the third mediator fragment and the fourth mediator fragment formed have different sequences, and hybridize to said detection probe at different positions. Therefore, the first duplex comprising an extension product of the first mediator fragment and the detection probe, the second duplex comprising an extension product of the second mediator fragment and the detection probe, the third duplex comprising an extension product of the third mediator fragment and the detection probe, and the fourth duplex comprising an extension product of the fourth mediator fragment and the detection probe, are different from each other in terms of structure (sequence). Correspondingly, said first, second, third and fourth duplex have different melting points ($T_m$ values). Therefore, in melting curve analysis, said first, second, third and fourth duplex show four melting peaks that are distinguishable from each other. Therefore, by detecting the melting peak of the first, second, third or fourth duplex, the presence of the first, second, third or fourth target nucleic acid sequence in the sample can be determined.

In addition, since the sequences of the first, second, third and fourth mediator sequence and the detection probe are known or predetermined, the melting points ($T_m$ values) of the first, second, third and fourth duplexes can be calculated beforehand. Therefore, by detecting the melting peak corresponding to the melting point ($T_m$ value) of the first, second, third or fourth duplex in melting curve analysis, the presence of the first, second, third or fourth target nucleic acid sequence in the sample can be determined.

Similarly, more upstream oligonucleotide sequences and more mediator probes can be used to carry out the method of the invention. For example, in some embodiments, at least 5 upstream oligonucleotide sequences, at least 5 mediator probes and one detection probe can be used to carry out the method of the invention, wherein, each upstream oligonucleotide sequence comprises a sequence complementary to a target nucleic acid sequence; and, each mediator probe comprising in 5' to 3' direction, a mediator sequence and a target specific sequence, wherein said mediator sequence comprises a sequence not complementary to a target nucleic acid sequence, and, said target specific sequence comprises a sequence complementary to a target nucleic acid sequence; thereby, when a certain target nucleic acid sequence is present, an upstream oligonucleotide sequence and a mediator probe corresponding to the target nucleic acid sequence can hybridize with the target nucleic acid sequence; and, when hybridizing with the target nucleic acid sequence, said upstream oligonucleotide sequence is located upstream of the target specific sequence of said mediator probe; and, the mediator sequences comprised in all the mediator probes are different from each other; and, said detection probe comprises a templating sequence, and multiple sequences that are located downstream of said templating sequence, and are complementary to the mediator sequence or a part thereof in one mediator probe, respectively. In such embodiments, the method of the invention can be used to detect at least 5 target nucleic acid sequences simultaneously.

In some embodiments, the method of the invention can use at least 6 upstream oligonucleotide sequences, at least 6 mediator probes and one detection probe; preferably, at least 7 upstream oligonucleotide sequences, at least 7 mediator probes and one detection probe; preferably, at least 8 upstream oligonucleotide sequences, at least 8 mediator probes and one detection probe; preferably, at least 9 upstream oligonucleotide sequences, at least 9 mediator probes and one detection probe; preferably, at least 10 upstream oligonucleotide sequences, at least 10 mediator probes and one detection probe; preferably, at least 12 upstream oligonucleotide sequences, at least 12 mediator probes and one detection probe; preferably, at least 15 upstream oligonucleotide sequences, at least 15 mediator probes and one detection probe; preferably, at least 20 upstream oligonucleotide sequences, at least 20 mediator probes and one detection probe; wherein, said upstream oligonucleotide sequences, mediator probes and detection probes have the same meanings as defined above. In such embodiments, the method of the invention can be used to detect at least 6, at least 7, at least 8, at least 9, at least 10, at least 12, at least 15, or at least 20 target nucleic acid sequences simultaneously.

Therefore, in some embodiments, the invention provides a method for detecting the presence of n target nucleic acid sequences in a sample, wherein, n is an integer of ≥2 (e.g. n is an integer of 2, 3, 4, 5, 6, 7, 8, 9, 10, 11, 12, 13, 14, 15, 16, 17, 18, 19, 20 or greater), and, said method comprises the following steps:

(1) for each target nucleic acid sequence to be detected, providing an upstream oligonucleotide sequence and a mediator probe; wherein, said upstream oligonucleotide sequence comprises a sequence complementary to said target nucleic acid sequence; and, said mediator probe comprises in 5' to 3' direction, a mediator sequence and a target specific sequence, said mediator sequence comprises a sequence not complementary to said target nucleic acid sequence, and, said target specific sequence comprises a sequence complementary to said target nucleic acid sequence; and, when hybridizing with said target nucleic acid sequence, said upstream oligonucleotide sequence is located upstream of said target specific sequence; and, the mediator sequences comprised in all the mediator probes are different from each other;

and, under a condition that allows nucleic acid hybridization, contacting the sample with the upstream oligonucleotide sequences and the mediator probes as provided;

(2) under a condition that allows cleavage of mediator probes, contacting the product in Step (1) with an enzyme having 5' nuclease activity;

(3) under a condition that allows nucleic acid hybridization, contacting the product in Step (2) with a detection probe comprising in 3' to 5' direction, capture sequences complementary to each mediator sequence or a part thereof, and a templating sequence; and, said detection probe is labeled with a reporter group and a quencher group, wherein, said reporter group can generate a signal, and, said quencher group can absorb or quench the signal generated by said reporter group; and, the signal, as generated by said detection probe when hybridizing with its complementary sequence, is different from the signal, as generated when not hybridizing with its complementary sequence;

(4) under a condition that allows extension reaction of a nucleic acid polymerase, contacting the product in Step (3) with a nucleic acid polymerase;

(5) subjecting the product in Step (4) to melting curve analysis; and according to the result of the melting curve analysis, determining whether said n target nucleic acid sequences are present in said sample.

In Step (1) of such embodiments, when a certain target nucleic acid sequence is present, both an upstream oligonucleotide sequence corresponding to the target nucleic acid sequence (i.e. an upstream oligonucleotide sequence comprising a sequence complementary to the target nucleic acid sequence), and a mediator probe corresponding to the target nucleic acid sequence (i.e. a mediator probe comprising a target specific sequence comprising a sequence complementary to the target nucleic acid sequence) hybridize with the target nucleic acid sequence.

Further, in Step (2) of such embodiments, when a certain target nucleic acid sequence is present, an upstream oligonucleotide sequence and a mediator probe corresponding to the target nucleic acid sequence hybridize with the target nucleic acid sequence, however, the mediator sequence in said mediator probe is in a free state, and does not hybridize with the target nucleic acid sequence. In such a case, in the presence of an enzyme having 5' nuclease activity, the mediator sequence or a part thereof in said mediator probe (a mediator probe corresponding to the target nucleic acid sequence) is cleaved off from said mediator probe due to the presence of the upstream oligonucleotide sequence (or an extension product thereof) corresponding to the target nucleic acid sequence, to form a mediator fragment corresponding to the target nucleic acid sequence.

Further, in Steps (3) and (4) of such embodiments, when a mediator fragment corresponding to a certain target nucleic acid sequence is present, said mediator fragment hybridizes with said detection probe, and, said nucleic acid polymerase will use said detection probe as a template, to extend said mediator fragment, and form a duplex corresponding to said target nucleic acid sequence. Further, in Step (5) of such embodiments, when the melting peak of a duplex corresponding to a certain target nucleic acid sequence is detected or not, it is determined that said target nucleic acid sequence is present or absent in said sample.

Particularly, in such embodiments, since the mediator sequences comprised in all the mediator probes used are different from each other, each mediator fragment formed has a different sequence, and hybridizes to said detection probe at a different position. Therefore, each duplex consisting of the extension product of a mediator fragment and the detection probe is different in terms of structure (sequence). Correspondingly, each duplex has a different melting point ($T_m$ value). Therefore, in melting curve analysis, each duplex shows a different melting peak. Therefore, by detecting the melting peak of a certain duplex, the presence of the target nucleic acid sequence corresponding to the duplex in the sample can be determined.

In addition, since the sequences of each mediator sequence and the detection probe are known or predetermined, the melting point ($T_m$ value) of each duplex can be calculated beforehand. Therefore, by detecting the melting peak corresponding to the melting point ($T_m$ value) of a certain duplex in melting curve analysis, the presence of the target nucleic acid sequence corresponding to the duplex in the sample can be determined.

The basic principle of the method of the invention is briefly summarized above. By reference to the steps of the method of the invention, the method of the invention is explained in detail and illustrated.

With respect to Steps (1) and (2)

In the method of the invention, a target nucleic acid sequence (e.g. a first or a second target nucleic acid sequence; if present) in a sample first hybridizes with the corresponding upstream oligonucleotide sequence (e.g. a first or a second upstream oligonucleotide sequence) and the corresponding mediator probe (e.g. a first or a second mediator probe).

In the method of the invention, the sample may be any sample to be detected. For example, in some preferred embodiments, the sample comprises or is DNA (e.g. genomic DNA or cDNA). In some preferred embodiments, the sample comprises or is RNA (e.g. mRNA). In some preferred embodiments, the sample comprises or is a mixture of nucleic acids (e.g. a mixture of DNA, a mixture of RNA, or a mixture of DNA and RNA).

In the method of the invention, the target nucleic acid sequence to be detected is not limited with respect to its sequence or length. For example, said target nucleic acid sequence may be DNA (e.g. genomic DNA or cDNA) or RNA (e.g. mRNA) molecule. In addition, the target nucleic acid sequence to be detected may be single-stranded or double-stranded.

When the sample or the target nucleic acid sequence to be detected is mRNA, preferably, before carrying out the method of the invention, reverse transcription reaction is carried out to obtain cDNA complementary to said mRNA. With respect to the detailed description of reverse transcription reaction, please see, for example, Joseph Sam-brook, et al., Molecular Cloning, A Laboratory Manual, Cold Spring Harbor Laboratory Press, Cold Spring Harbor, N.Y. (2001).

The sample or the target nucleic acid sequence to be detected can be obtained from any source, including, but not limited to prokaryotes, eukaryotes (e.g. protozoa, parasites, fungi, yeasts, plants, animals including mammal and human) or viruses (e.g. Herpes virus, HIV, influenza virus, Epstein-Barr virus, hepatitis virus, poliovirus, etc.) or viroids. The sample or the target nucleic acid sequence to be detected can also be a nucleic acid sequence in any form, for example, a genomic sequence, an artificially isolated or fragmented sequence, a synthesized sequence, etc.

In some embodiments of the invention, the mediator probe can comprise or consist of naturally occurring nucleotides (e.g. deoxyribonucleotides or ribonucleotides), modified nucleotides, unnatural nucleotides, or any combination thereof. In some preferred embodiments, the mediator probe comprises or consists of natural nucleotides (e.g. deoxyribonucleotides or ribonucleotides). In some preferred embodiments, the mediator probe comprises modified nucleotides, for example, modified deoxyribonucleotide or ribonucleotide, for example, 5-methylcytosine or 5-hydroxymethylcytosine. In some preferred embodiments, the mediator probe comprises unnatural nucleotides, for example, deoxyhypoxanthine, inosine, 1-(2'-deoxy-β-D-ribofuranosyl)-3-nitropyrrole, 5-nitroindole or locked nucleic acid (LNA).

In the method of the invention, the mediator probe is not limited with respect to its length. For example, the mediator probe may have a length of 15-1000 nt, for example, 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, 900-1000 nt. For example, a mediator probe may have a length of 15-150 nt, for example, 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, 140-150 nt. The target specific sequence in a mediator probe may be of any length, as long as it can specifically hybridize with a target nucleic acid sequence. For example, the target specific sequence in a mediator probe may have a length of 10-500 nt, for example, 10-20 nt, 20-30 nt, 30-40 nt, 40-50 nt, 50-60 nt, 60-70 nt, 70-80 nt, 80-90 nt, 90-100 nt, 100-150 nt, 150-200 nt, 200-250 nt, 250-300 nt, 300-350 nt, 350-400 nt, 400-450 nt, 450-500 nt. For example, a target specific sequence in a mediator probe may have a length of 10-140 nt, for example, 10-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt. The mediator sequence in a mediator probe may be of any length, as long as it can specifically hybridize with a detection probe and be extended. For example, the mediator sequence in a mediator probe may have a length of 5-140 nt, for example, 5-10 nt, 8-50 nt, 8-15 nt, 15-20 nt, 10-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt. In some preferred embodiments, the target specific sequence in a mediator probe may have a length of 10-100 nt (e.g. 10-90 nt, 10-80 nt, 10-50 nt, 10-40 nt, 10-30 nt, 10-20 nt), and, the mediator sequence has a length of 5-100 nt (e.g. 10-90 nt, 10-80 nt, 10-50 nt, 10-40 nt, 10-30 nt, 10-20 nt).

In some preferred embodiments, the mediator probe has 3'-OH end; preferably, the base at 3' end of such a mediator probe is not complementary to a target sequence, and therefore the mediator probe can hardly be extended. In some preferred embodiments, the 3'-end of the mediator probe is blocked, so as to inhibit its extension. The 3'-end of a nucleic acid (e.g. the mediator probe) can be blocked by various methods. For example, the mediator probe can be modified at 3'-OH of the last nucleotide, so as to block the 3' end of the mediator probe. In some embodiments, by adding a chemical moiety (e.g. biotin or alkyl) at 3'-OH of the last nucleotide of the mediator probe, the 3'-end of the mediator probe is blocked. In some embodiments, by removing 3'-OH of the last nucleotide of the mediator probe, or replacing said last nucleotide with dideoxynucleotide, the 3'-end of the mediator probe is blocked.

In some embodiments of the invention, the upstream oligonucleotide sequence may comprise or consist of naturally occurring nucleotides (e.g. deoxyribonucleotides or ribonucleotides), modified nucleotides, unnatural nucleotides, or any combination thereof. In some preferred embodiments, the upstream oligonucleotide sequence comprises or consists of natural nucleotides (e.g. deoxyribonucleotides or ribonucleotides). In some preferred embodiments, the upstream oligonucleotide sequence comprises modified nucleotides, for example, modified deoxyribonucleotides or ribonucleotides, for example, 5-methylcytosine or 5-hydroxymethylcytosine. In some preferred embodiments, the upstream oligonucleotide sequence comprises unnatural nucleotides, for example, deoxyhypoxanthine, inosine, 1-(2'-deoxy-β-D-ribofuranosyl)-3-nitropyrrole, 5-nitroindole or locked nucleic acid (LNA).

In the method of the invention, the upstream oligonucleotide sequence is not limited with respect to its length, as long as it can specifically hybridize with a target nucleic acid sequence. For example, the upstream oligonucleotide sequence may have a length of 15-150 nt, for example, 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, 140-150 nt.

In the method of the invention, the condition that allows nucleic acid hybridization, can be conventionally determined by a person skilled in the art. For example, depending on the target nucleic acid sequence to be detected, the upstream oligonucleotide sequence as used, and the target specific sequence in a mediator probe, suitable hybridization conditions can be determined. In some embodiments of the invention, the condition that allows nucleic acid hybridization is such a stringent condition that allows the hybridization of an upstream oligonucleotide sequence and the target specific sequence in a mediator probe with the corresponding target nucleic acid sequence by complementary base pairing, and, the mediator sequence in a mediator probe does not hybridize with said target nucleic acid sequence. In some preferred embodiments, under a high stringent condition, the sample is contacted with each upstream oligonucleotide sequence and each mediator probe.

In the method of the invention, after contacting the sample with each upstream oligonucleotide sequence and each mediator probe, the mediator probe needs to be cleaved to release a fragment (i.e. a mediator fragment) comprising the mediator sequence or a part thereof. Under common conditions, an enzyme having 5' nuclease activity can be used, and an upstream oligonucleotide sequence hybridized with a target nucleic acid sequence or an extension product thereof is used to induce the cleavage of the mediator probe hybridized with the target nucleic acid sequence. Particularly, in Step (1), when a mediator probe is in contact with a target nucleic acid sequence, the target specific sequence comprised therein hybridizes with the target nucleic acid sequence to form a double-stranded structure, while the mediator sequence does not hybridize with the target nucleic acid sequence, so as to retain a single-stranded structure. Therefore, an enzyme having 5' nuclease activity can be used to cleave the oligonucleotides comprising a double-stranded structure and a single-stranded structure, and to release a fragment having the single-stranded structure.

It is easy to understand that in the method of the invention, under a condition that allows nucleic acid hybridization, an upstream oligonucleotide sequence and a mediator probe will hybridize with the same strand of a target nucleic acid sequence, and the upstream oligonucleotide sequence is located upstream of the mediator probe, so as to induce the cleavage of the mediator probe. In some embodiments of the invention, the cleavage of a mediator probe can be induced in the following two manners: (A) the one that does not depend on the extension of the upstream oligonucleotide sequence; and (B) the one that depends on the extension of the upstream oligonucleotide sequence. Particularly, after the hybridization of an upstream oligonucleotide sequence and a mediator probe with a target nucleic acid sequence, if the upstream oligonucleotide sequence and the mediator probe are close enough to enable an enzyme having 5' nuclease activity to induce the cleavage of the mediator probe, the enzyme will bind to the upstream oligonucleotide sequence, and cleave the mediator probe, without the need of carrying out an extension reaction (i.e. manner A).

Alternatively, after hybridizing with a target nucleic acid sequence, if the upstream oligonucleotide sequence is far away from the mediator probe, a nucleic acid polymerase is used first, with the target nucleic acid sequence as a template, to catalyze extension of the upstream oligonucleotide sequence, and then an enzyme having 5' nuclease activity binds to the extension product of the upstream oligonucleotide sequence, and cleaves the mediator probe (i.e. manner B).

Therefore, in some preferred embodiments, after hybridizing with the target nucleic acid sequence, the upstream oligonucleotide sequence is adjacent to the upstream of the mediator probe. In such embodiments, the upstream oligonucleotide sequence directly induces an enzyme having 5' nuclease activity to cleave the mediator probe, without the need of carrying out an extension reaction. Therefore, in such embodiments, the upstream oligonucleotide sequence is an upstream probe specific for the target nucleic acid sequence, and induce the cleavage of the mediator probe in an extension-independent manner. As used herein, the term "adjacent to" intends to mean that two nucleic acid sequences are adjacent to each other, to form a gap. In some preferred embodiments, the distance between two contiguous nucleic acid sequences (e.g. an upstream oligonucleotide sequence and a mediator probe) is no more than 30 nt, for example, no more than 20 nt, for example, no more than 15 nt, for example, no more than 10 nt, for example, no more than 5 nt, for example, 4 nt, 3 nt, 2 nt, 1 nt.

In some preferred embodiments, after hybridizing with the target nucleic acid sequence, the upstream oligonucleotide sequence and the target specific sequence of the mediator probe have a partially overlapping sequence. In such embodiments, the upstream oligonucleotide sequence directly induces an enzyme having 5' nuclease activity to cleave the mediator probe, without the need of carrying out an extension reaction. Therefore, in such embodiments, the upstream oligonucleotide sequence is an upstream probe specific for the target nucleic acid sequence, which induce the cleavage of the mediator probe in an extension-independent manner. In some preferred embodiments, said partially overlapping sequence has a length of 1-10 nt, for example, 1-5 nt, or 1-3 nt.

In some preferred embodiments, after hybridizing with the target nucleic acid sequence, the upstream oligonucleotide sequence is located far from the upstream of the mediator probe. In such embodiments, the upstream oligonucleotide sequence is extended by a nucleic acid polymerase, and then the extension product produced induces an enzyme having 5' nuclease activity to cleave the mediator probe. Therefore, in such embodiments, the upstream oligonucleotide sequence is a primer specific for the target nucleic acid sequence, which is used to trigger the extension reaction, and induces the cleavage of the mediator probe in an extension-dependent manner. As used herein, the term "far" intends to mean that the two nucleic acid sequence are far away from each other, for example, the distance between them is at least 30 nt, at least 50 nt, at least 80 nt, at least 100 nt or longer.

Therefore, in some preferred embodiments, said upstream oligonucleotide sequence is a primer specific for the target nucleic acid sequence or a probe specific for the target nucleic acid sequence. Said primer is suitable for inducing the cleavage of the mediator probe in an extension-dependent manner. Said probe is suitable for inducing the cleavage of the mediator probe in an extension-independent manner.

Methods for inducing the cleavage of downstream oligonucleotides by using upstream oligonucleotides are known by a person skilled in the art, and can be used in the invention. With respect to the detailed description of these methods, please see, for example, U.S. Pat. Nos. 5,210,015, 5,487,972, 5,691,142, 5,994,069 and 7,381,532, and US application US 2008/0241838.

In some embodiments, the cleavage site of the mediator probe is at a place where the mediator sequence is linked to the target specific sequence (i.e. a place where the sequence hybridized with the target nucleic acid is linked to the sequence not hybridized with the target nucleic acid). In such embodiments, the cleavage of the mediator probe by an enzyme will release a fragment comprising the intact mediator sequence. In some embodiments, the cleavage site of the mediator probe is located within the 3'-terminal region of the mediator sequence (i.e. is located upstream of the 3'-end of the mediator sequence, and, for example, is several nucleotides, for example, 1-3 nucleotides away from the 3'-end of the mediator sequence). In such embodiments, the cleavage of the mediator probe by an enzyme will release a fragment comprising a part (5'-terminal moiety) of the mediator sequence. Therefore, in some embodiments of the invention, the mediator fragment comprises the intact mediator sequence, or a part (5'-terminal moiety) of the mediator sequence, for example, comprises at least 5 nt, at least 8 nt, at least 10 nt, at least 20 nt, at least 30 nt, at least 40 nt, at least 50 nt, for example, 5-50 nt, 5-10 nt, 10-20 nt, 20-30 nt, 30-40 nt, 40-50 nt of the 5'-end of the mediator sequence.

In the present application, various enzymes having 5' nuclease activity can be used to carry out the method of the invention. In some preferred embodiments, said enzyme having 5' nuclease activity is an enzyme having 5' exonuclease activity. In some preferred embodiments, said enzyme having 5' nuclease activity is a nucleic acid polymerase (e.g. DNA polymerase, particularly a thermally stable DNA polymerase) having 5' nuclease activity (e.g. 5' exonuclease activity). In some embodiments, nucleic acid polymerases having 5' nuclease activity are particularly advantageous, as said polymerases can not only use the target nucleic acid sequence as a template, to catalyze the extension of the upstream oligonucleotide sequence, but can also induce the cleavage of the mediator probe.

In some preferred embodiments, a DNA polymerase having 5' nuclease activity is a thermally stable DNA polymerase, which can be obtained from various bacteria, for example, *Thermus aquaticus* (Taq), *Thermus thermophiles* (Tth), *Thermus filiformis*, *Thermis flavus*, *Thermococcus literalis*, *Thermus antranildanii*, *Thermus caldophllus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus thermophllus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosiphoafricanus*, *Pyrococcus woesei*, *Pyrococcus horikoshii*, *Pyrococcus abyssi*, *Pyrodictium occultum*, *Aquifexpyrophilus* and *Aquifex aeolieus*. Preferably, said DNA polymerase having 5' nuclease activity is Taq polymerase.

Alternatively, in Step (2), two different enzymes may be used: a nucleic acid polymerase and an enzyme having 5' nuclease activity. In such embodiments, a nucleic acid polymerase uses the target nucleic acid sequence as a template to catalyze the extension of the upstream oligonucleotide sequence, and an enzyme having 5' nuclease activity binds to the extension product of the upstream oligonucleotide sequence, and catalyzes the cleavage of the mediator probe.

In some preferred embodiments, in Step (1) and/or (2), the sample is further contacted with a downstream oligonucleotide sequence (or a downstream primer) specific to the target nucleic acid sequence. In some embodiments, the use of a nucleic acid polymerase and a downstream oligonucleotide sequence (or a downstream primer) is particularly advantageous. Particularly, the nucleic acid polymerase can use the target nucleic acid sequence as a template, with the upstream oligonucleotide sequence and the downstream oligonucleotide sequence as primers, to produce additional target nucleic acid sequences, so as to enhance the sensitivity of the method of the invention.

Therefore, in some preferred embodiments, in Step (1), in addition to the upstream oligonucleotide sequences and mediator probe as defined above, for each target nucleic acid sequence to be detected, a downstream oligonucleotide sequence is further provided; wherein, said downstream oligonucleotide sequence comprises a sequence complementary to said target nucleic acid sequence; and, when hybridizing with said target nucleic acid sequence, said downstream oligonucleotide sequence is located downstream of said target specific sequence;

and then, under a condition that allows nucleic acid hybridization, said sample is contacted with the provided upstream oligonucleotide sequence, mediator probe and downstream oligonucleotide sequence.

In such embodiments, the upstream oligonucleotide sequence and the downstream oligonucleotide sequence act as an upstream primer and a downstream primer, respectively, for amplification of the target nucleic acid sequence. Therefore, it is easy to understand that the upstream oligonucleotide sequence and the downstream oligonucleotide sequence target to different strands of two complementary strands, respectively. Therefore, when the target nucleic acid sequence is a double-stranded molecule, the upstream oligonucleotide sequence and downstream oligonucleotide sequence are complementary to different strands (sense strand and antisense strand) of the target nucleic acid sequence; when the target nucleic acid sequence is a single-stranded molecule, the upstream oligonucleotide sequence and downstream oligonucleotide sequence are complementary to the target nucleic acid sequence and its complementary sequence, and therefore can be used to accomplish the amplification of the target nucleic acid sequence. However, in the present application, for simplicity, when describing the relationship between an upstream oligonucleotide sequence/downstream oligonucleotide sequence and a target nucleic acid sequence, it is generally called "complementary to the target nucleic acid sequence", without clearly distinguishing the sense strand and antisense strand of the target nucleic acid sequence, or clearly distinguishing the target nucleic acid sequence and its complementary sequence. However, a person skilled in the art can correctly understand the complementary relationship and the position relationship between the upstream oligonucleotide sequence/downstream oligonucleotide sequence and the target nucleic acid sequence.

For example, when the method of the invention is used to detect a first and second target nucleic acid sequence, a first and second downstream oligonucleotide sequence can be provided, which comprise sequences complementary to the first and second target nucleic acid sequence, respectively. Similarly, for a third target nucleic acid sequence, a third downstream oligonucleotide sequence is provided, which comprises a sequence complementary to the third target nucleic acid sequence. For a fourth target nucleic acid sequence, a fourth downstream oligonucleotide sequence can also be provided, which comprises a sequence complementary to the fourth target nucleic acid sequence.

Further, in some preferred embodiments, in Step (2), the product in Step (1) is in contact with a nucleic acid polymerase (preferably, a nucleic acid polymerase having 5' nuclease activity). In further preferred embodiments, under a condition that allows nucleic acid amplification, the product in Step (1) is in contact with a nucleic acid polymerase having 5' nuclease activity. In such embodiments, the nucleic acid polymerase will use the upstream and downstream oligonucleotides as primers, to amplify the target nucleic acid sequence. Moreover, during the amplification of the target nucleic acid, the nucleic acid polymerase induces the cleavage of the mediator probe hybridized to the target nucleic acid sequence by virtue of its 5' nuclease activity, so as to release a mediator fragment comprising the mediator sequence or a part thereof. Various nucleic acid polymerases having 5' nuclease activity can be used to carry out the method of the invention, particularly the nucleic acid polymerases as described above. In the present application, preferably, the nucleic acid polymerase used is a template-dependent nucleic acid polymerase (e.g. a template-dependent DNA polymerase).

In some embodiments of the invention, the downstream oligonucleotide sequence may comprise or consist of naturally occurring nucleotides (e.g. deoxyribonucleotides or ribonucleotides), modified nucleotides, unnatural nucleotides, or any combination thereof. In some preferred embodiments, the downstream oligonucleotide sequence comprises or consists of natural nucleotides (e.g. deoxyribonucleotides or ribonucleotides). In some preferred embodiments, the downstream oligonucleotide sequence comprises modified nucleotides, for example, modified deoxyribonucleotide or ribonucleotide, for example, 5-methylcytosine or 5-hydroxymethylcytosine. In some preferred embodiments, the downstream oligonucleotide sequence comprises unnatural nucleotides, for example, deoxyhypoxanthine, inosine, 1-(2'-deoxy-β-D-ribofuranosyl)-3-nitropyrrole, 5-nitroindole or locked nucleic acid (LNA).

In the method of the invention, the downstream oligonucleotide sequence is not limited with respect to its length, as long as it can specifically hybridize with the target nucleic acid sequence. For example, the downstream oligonucleotide sequence may have a length of 15-150 nt, for example, 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, 140-150 nt.

In some preferred embodiments, the target nucleic acid sequence is amplified in a symmetric manner. In such embodiments, for a certain target nucleic acid sequence, the upstream and downstream oligonucleotide sequence are used at an equal amount in amplification. In some preferred embodiments, the target nucleic acid sequence is amplified in an asymmetric manner. In such embodiments, for a certain target nucleic acid sequence, the upstream and downstream oligonucleotide sequence are used at a different amount in amplification. In some embodiments, the upstream oligonucleotide sequence is used in an excessive amount relative to the downstream oligonucleotide sequence (e.g. in excess of at least 1 fold, at least 2 folds, at least 5 folds, at least 8 folds, at least 10 folds, for example, in excess of 1-10 folds). In some embodiments, the downstream oligonucleotide sequence is used in an excessive amount relative to the upstream oligonucleotide sequence (e.g. in excess of at least 1 folds, at least 2 folds, at least 5 folds, at least 8 folds, at least 10 folds, for example, in excess of 1-10 folds).

In some preferred embodiments, the target nucleic acid sequence is amplified by a three-step method. In such embodiments, each round of nucleic acid amplification is subjected to three steps: performing nucleic acid denaturation at a first temperature, performing nucleic acid annealing at a second temperature, and performing nucleic acid extension at a third temperature. In some preferred embodiments, the target nucleic acid sequence is amplified by a two-step method. In such embodiments, each round of nucleic acid amplification is subjected to two steps: performing nucleic acid denaturation at a first temperature, and performing nucleic acid annealing and extension at a second temperature. The temperatures suitable for performing nucleic acid denaturation, nucleic acid annealing and nucleic acid extension can be easily determined by a person skilled in the art through conventional methods (see, for example, Joseph Sambrook, et al., Molecular Cloning, A Laboratory Manual, Cold Spring Harbor Laboratory Press, Cold Spring Harbor, N.Y. (2001)).

In the method of the invention, the mediator probe used generally corresponds to the target nucleic acid sequence one by one. In other words, for each target nucleic acid sequence to be detected, a unique mediator probe is provided. However, it is easy to understand that for the upstream oligonucleotide sequence, the downstream oligonucleotide sequence and the target nucleic acid sequence, one-to-one correspondence is not required. For example, in some cases, the sample to be detected is a DNA library, and all the fragments in the library comprise the same adaptor at one or both ends. Under such a situation, the same upstream oligonucleotide sequence may be used for extension, or the same upstream oligonucleotide sequence and/or downstream oligonucleotide sequence may be used for extension, so as to induce the cleavage of the mediator probe. Therefore, in the method of the invention, for different target nucleic acid sequences, an identical upstream oligonucleotide sequence or different upstream oligonucleotide sequences may be used; and/or, an identical downstream oligonucleotide sequence or different downstream oligonucleotide sequences may be used. For example, the first, second, third and fourth upstream oligonucleotide sequence may be identical or different. The first, second, third and fourth downstream oligonucleotide sequence may also be identical or different.

In addition, when a nucleic acid polymerase having 5' nuclease activity is used in Step (2), HANDS strategy may also be used to enhance the efficiency of nucleic acid amplification (see, for example, Nucleic Acids Research, 1997, 25 (16):3235-3241). For example, in some preferred embodiments, an identical oligonucleotide sequence may be introduced at 5' end of all the upstream oligonucleotide sequences and downstream oligonucleotide sequences, and then a common primer complementary to the identical oligonucleotide sequence (preferably, the amount thereof is generally much higher than that of the upstream and downstream oligonucleotide sequences) may be used for amplification.

Therefore, in some preferred embodiments, in Step (1), all the upstream oligonucleotide sequences (e.g. the first, second, third and fourth upstream oligonucleotide sequence) and downstream oligonucleotide sequences (e.g. the first, second, third and fourth downstream oligonucleotide sequence) as provided comprise an identical oligonucleotide sequence at 5' end, and, a common primer is further provided, said common primer has a sequence complementary to the identical oligonucleotide sequence; then, under a condition that allows nucleic acid hybridization, said sample is contacted with the provided upstream oligonucleotide sequence, mediator probe, downstream oligonucleotide sequence and common primer. In some preferred embodiments, the identical oligonucleotide sequence has a length of 8-50 nt, e.g. 8-15 nt, 15-20 nt, 20-30 nt, 30-40 nt, or 40-50 nt. Correspondingly, said common primer may have a length of 8-50 nt, e.g. 8-15 nt, 15-20 nt, 20-30 nt, 30-40 nt, or 40-50 nt. Later, in some preferred embodiments, in Step (2), the product in Step (1) is contacted with a nucleic acid polymerase (preferably, a nucleic acid polymerase having 5' nuclease activity). In further preferred embodiments, under a condition that allows nucleic acid amplification, the product in Step (1) is contacted with a nucleic acid polymerase having 5' nuclease activity. In such embodiments, the nucleic acid polymerase will use the upstream and downstream oligonucleotide as primers, to preliminarily amplify the target nucleic acid sequence, to obtain a preliminarily amplified product; later, the common primer is used to further amplify the preliminarily amplified product. Moreover, during the whole amplification, the nucleic acid polymerase cleaves the mediator probe hybridized to the target nucleic acid sequence or the preliminarily amplified product, by virtue of its 5' nuclease activity, so as to release a mediator fragment comprising the mediator sequence or a part thereof.

In some embodiments of the invention, the common primer may comprise or consist of naturally occurring nucleotides (e.g. deoxyribonucleotides or ribonucleotides), modified nucleotides, unnatural nucleotides, or any combination thereof. In some preferred embodiments, the common primer comprises or consists of natural nucleotides (e.g. deoxyribonucleotides or ribonucleotides). In some preferred embodiments, the common primer comprises modified nucleotides, for example, modified deoxyribonucleotide or ribonucleotide, for example, 5-methylcytosine or 5-hydroxymethylcytosine. In some preferred embodiments, the common primer comprises unnatural nucleotides, for example, deoxyhypoxanthine, inosine, 1-(2'-deoxy-β-D-ribofuranosyl)-3-nitropyrrole, 5-nitroindole or locked nucleic acid (LNA).

In the method of the invention, the common primer is not limited with respect to its length, as long as it can specifically hybridize with the identical oligonucleotide sequence comprised in the upstream and downstream oligonucleotide sequences. For example, the common primer may have a length of 8-50 nt, for example, 8-15 nt, 15-20 nt, 20-30 nt, 30-40 nt, or 40-50 nt.

With Respect to Step (3) and (4)

In Step (2), an enzyme having 5' nuclease activity cleaves the mediator probe hybridized to the target nucleic acid sequence, to release a mediator fragment comprising the mediator sequence or a part thereof, which is then hybridized with the detection probe in Step (3). In the present application, the detection probe comprises in 3' to 5' direction, capture sequences complementary to each mediator sequence or a part thereof, and a templating sequence. Therefore, in Step (4), in the presence of a nucleic acid polymerase, the detection probe is used as a template, for extension of the mediator fragment; while the mediator fragment is used as a primer, for triggering the extension reaction; and after the extension reaction is finished, the extension product of the mediator fragment is hybridized with the detection probe, to form a nucleic acid duplex.

In the method of the invention, the detection probe comprises multiple capture sequences complementary to multiple mediator sequences or parts thereof (e.g. a first capture sequence complementary to a first mediator sequence or a part thereof, a second capture sequence complementary to a second mediator sequence or a part thereof, a third capture sequence complementary to a third mediator sequence or a part thereof, and/or a fourth capture sequence complementary to a fourth mediator sequence or a part thereof). It is easy to understand that various capture sequences can be arranged in any order. For example, a first capture sequence may be located upstream (5' end) or downstream (3' end) of a second capture sequence. For example, the detection probe may comprise in 3' to 5' direction, a first capture sequence and a second capture sequences; or, a second capture sequence and a first capture sequence. Similarly, the detection probe may comprise other capture sequences (e.g. a first, a second, a third, a fourth capture sequences) in any order.

In addition, various capture sequences can be arranged in any manner. For example, various capture sequences may be arranged in a contiguous manner, or arranged in such a manner that they are spaced by a linking sequence. For example, a first capture sequence and a second capture sequence may be arranged contiguously; or, they are spaced by a linking sequence (also called "linker" for short here); or, there is an overlapping sequence between them. Similarly, the detection probe may comprise other capture sequences (e.g. a first, a second, a third, a fourth capture sequences) in any arrangement manner.

In some cases, it is particularly advantageous that various capture sequences are arranged in an overlapping manner. In such embodiments, multiple mediator sequences can be designed so that different mediator sequences comprise overlapping sequences. For example, a first mediator sequence and a second mediator sequence can be designed, so that the 3' terminal moiety of the first mediator sequence has the same sequence as the 5' terminal moiety of the second mediator sequence. Correspondingly, in the detection probe, the 5' terminal moiety of the first capture sequence complementary to the first mediator sequence has the same sequence as the 3' terminal moiety of the second capture sequence complementary to the second mediator sequence. Therefore, the detection probe may comprise in 3' to 5' direction, a first capture sequence and a second capture sequence, which can be arranged in an overlapping manner. In this case, the overlapping sequence is the same sequence or a part thereof as shared by the first and second capture sequences. By arranging capture sequences in an overlapping manner, the detection probe can comprise more capture sequences within a predetermined length, and therefore can hybridize with more mediator fragments. In other words, by arranging capture sequences in an overlapping manner, a single detection probe can be used in combination with more mediator probes.

As described above, in the method of the invention, a single detection probe and at least 2 (e.g. 3, 4, 5, 6, 7, 8, 9, 10, 11, 12, 13, 14, 15, 16, 17, 18, 19, 20 or more) mediator probes are used in combination. Therefore, in some preferred embodiments, the amount of a single detection probe is excessive relative to the amount of a single mediator probe (e.g. in excess of at least 1 folds, at least 2 folds, at least 5 folds, at least 10 folds, at least 20 folds). Such embodiments are advantageous in some cases, as the whole reaction system comprises enough detection probes to hybridize with the released mediator fragments, mediate the extension of the mediator fragments, and form duplexes.

As described above, the mediator fragment may comprise the intact mediator sequence or a part thereof. When the mediator fragment comprises the intact mediator sequence, said detection probe may preferably comprise a sequence complementary to said mediator sequence. When the mediator fragment comprises a part (5'-terminal moiety) of the mediator sequence, said detection probe may preferably comprise a sequence complementary to the part (5'-terminal moiety) of said mediator sequence, or, a sequence complementary to the intact mediator sequence. In some preferred embodiments, said detection probe comprises a sequence complementary to said mediator sequence. Such detection probes are particularly advantageous in some cases, as they can not only hybridize with the mediator fragment comprising the intact mediator sequence, but also hybridize with the mediator fragment comprising a part (5'-terminal moiety) of the mediator sequence. However, it should be understood that said detection probe may also comprise a sequence only complementary to a part (e.g. 3'-terminal moiety) of the mediator fragment, as long as said detection probe can stably hybridize with the mediator fragment, and start the extension reaction.

Further, in addition to the capture sequences and templating sequence, the detection probe may also comprise an additional sequence at 3' end (i.e. downstream of capture sequences). Said additional sequence generally comprises a sequence not complementary to the mediator fragment, and is not involved in the hybridization of the mediator fragment.

According to the invention, the templating sequence in the detection probe may comprise any sequence, and, is located upstream (5' end) of each capture sequence, and therefore can be used as a template for extending the mediator fragment. In some preferred embodiments, said templating sequence comprises a sequence not complementary to the mediator probe (a mediator sequence and a target specific sequence). Such templating sequences are particularly advantageous in some cases, as they can enhance the specificity of mediator fragments for hybridization with detection probes, and avoid the hybridization of mediator fragments at undesired positions, so as to avoid the production of undesired duplexes.

In some embodiments of the invention, the detection probe may comprise or consist of naturally occurring nucleotides (e.g. deoxyribonucleotides or ribonucleotides), modified nucleotides, unnatural nucleotides (e.g. peptide nucleic acid (PNA) or locked nucleic acid), or any combination thereof. In some preferred embodiments, the detection probe comprises or consists of natural nucleotides (e.g. deoxyribonucleotides or ribonucleotides). In some preferred embodiments, the detection probe comprises modified nucleotides, for example, modified deoxyribonucleotide or ribonucleotide, for example, 5-methylcytosine or 5-hydroxymethylcytosine. In some preferred embodiments, the detection probe comprises unnatural nucleotides, for example, deoxyhypoxanthine, inosine, 1-(2'-deoxy-β-D-ribofuranosyl)-3-nitropyrrole, 5-nitroindole or locked nucleic acid (LNA).

In the method of the invention, the detection probe is not limited with respect to its length. For example, the detection probe may have a length of 15-1000 nt, for example, 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, 900-1000 nt. The capture sequence in the detection probe may be of any length, as long as it can specifically hybridize with a mediator fragment. For example, the capture sequence in the detection probe may have a length of 10-500 nt, for example, 10-20 nt, 20-30 nt, 30-40 nt, 40-50 nt, 50-60 nt, 60-70 nt, 70-80 nt, 80-90 nt, 90-100 nt, 100-150 nt, 150-200 nt, 200-250 nt, 250-300 nt, 300-350 nt, 350-400 nt, 400-450 nt, 450-500 nt. The templating sequence in the detection probe may be of any length, as long as it can be used as a template for extending the mediator fragment. For example, the templating sequence in the detection probe may have a length of 1-900 nt, for example, 1-5 nt, 5-10 nt, 10-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt. In some preferred embodiments, the capture sequence in the detection probe has a length of 10-200 nt (e.g. 10-190 nt, 10-180 nt, 10-150 nt, 10-140 nt, 10-130 nt, 10-120 nt, 10-100 nt, 10-90 nt, 10-80 nt, 10-50 nt, 10-40 nt, 10-30 nt, 10-20 nt), and, the templating sequence has a length of 5-200 nt (e.g. 10-190 nt, 10-180 nt, 10-150 nt, 10-140 nt, 10-130 nt, 10-120 nt, 10-100 nt, 10-90 nt, 10-80 nt, 10-50 nt, 10-40 nt, 10-30 nt, 10-20 nt).

In some preferred embodiments, the detection probe has 3'-OH end. In some preferred embodiments, the 3'-end of the detection probe is blocked, so as to inhibit its extension. The 3'-end of a nucleic acid (e.g. detection probe) can be blocked by various methods. For example, 3'-OH of the last nucleotide of the detection probe can be modified, so as to block the 3'-end of the detection probe. In some embodiments, a chemical moiety (e.g. biotin or alkyl) can be added to 3'-OH of the last nucleotide of the detection probe, so as to block the 3'-end of the detection probe. In some embodiments, by removing 3'-OH of the last nucleotide of the detection probe, or replacing said last nucleotide with dideoxynucleotide, the 3'-end of the detection probe can be blocked.

In the method of the invention, the mediator fragment hybridizes with the detection probe, and thereby start the extension reaction of a nucleic acid polymerase. Although an un-cleaved mediator probe can also hybridize with the detection probe via the mediator sequence, the mediator probe further comprises a target specific sequence, which is located downstream of the mediator sequence and does not hybridize with the detection probe (i.e. being in a free state), and therefore the nucleic acid polymerase cannot extend the un-cleaved mediator probe hybridized with the detection probe.

As described above, the detection probe is labeled with a reporter group and a quencher group, wherein, said reporter group can generate a signal, and, said quencher group can absorb or quench the signal generated by said reporter group; and, the signal, as generated by said detection probe when hybridizing with its complementary sequence, is different from the signal, as generated when not hybridizing with its complementary sequence.

In some preferred embodiments, said detection probe is a self-quenching probe. In such embodiments, when the detection probe does not hybridize with another sequence, the quencher group is located at a position where it can absorb or quench the signal of the reporter group (e.g. the quencher group is located near the reporter group), so as to absorb or quench the signal generated by the reporter group. In such a case, said detection probe does not generate a signal. Further, when said detection probe hybridizes with its complementary sequence, the quencher group is located at a position where it cannot absorb or quench the signal of the reporter group (e.g. the quencher group is located at a position far away from the reporter group), and therefore cannot absorb or quench the signal generated by the reporter group. In such a case, said detection probe generates a signal.

The design of such self-quenching detection probes is within the ability of a person skilled in the art. For example, said detection probe can be labeled with a reporter group at 5' end and labeled with a quencher group at 3' end, or said detection probe can be labeled with a reporter group at 3' end and labeled with a quencher group at 5' end. Therefore, when said detection probe is present alone, said reporter group is close to and interacts with said quencher group, so that the signal generated by said reporter group is absorbed by said quencher group, and therefore said detection probe does not generate a signal; however, when said detection probe hybridizes with its complementary sequence, said reporter group is separated from said quencher group, so that the signal generated by the reporter group cannot be absorbed by said quencher group, and therefore said detection probe generates a signal.

However, it should be understood, it is not necessary that the detection probe is labeled with a reporter group and a quencher group at its ends. The detection probe may also be labeled with a reporter group and/or a quencher group in the inner of the probe, as long as the signal, as generated by said detection probe when hybridizing with its complementary sequence, is different from the signal, as generated when not hybridizing with its complementary sequence. For example, the upstream (or downstream) of the detection probe is labeled with a reporter group, while the downstream (or upstream) of the detection probe is labeled with a quencher group, and the distance between them is far enough (e.g. a distance of 10-20 nt, 20-30 nt, 30-40 nt, 40-50 nt, 50-60 nt, 60-70 nt, 70-80 nt, or longer). Therefore, when said detection probe is present alone, since the probe molecule is randomly coiled or a secondary structure (e.g. hairpin structure) of the probe is formed, said reporter group is close to and interacts with said quencher group, so that said the signal generated by the reporter group is absorbed by said quencher group, and therefore said detection probe does not generate a signal; and, when said detection probe hybridizes with its complementary sequence, the distance between said reporter group and said quencher group is far enough, so that said the signal generated by the reporter group cannot be absorbed by said quencher group, and therefore said detection probe generates a signal. In some preferred embodiments, the distance between a reporter group and a quencher group is 10-80 nt or longer, for example, 10-20 nt, 20-30 nt, 30-40 nt, 40-50 nt, 50-60 nt, 60-70 nt, 70-80 nt. In some preferred embodiments, the distance between a reporter group and a quencher group is no more than 80 nt, no more than 70 nt, no more than 60 nt, no more than 50 nt, no more than 40 nt, no more than 30 nt, or no more than 20 nt. In some preferred embodiments, the distance between a reporter group and a quencher group is at least 5 nt, at least 10 nt, at least 15 nt, or at least 20 nt.

Therefore, the detection probe can be labeled with a reporter group and a quencher group at any suitable positions, as long as the signal, as generated by said detection probe when hybridizing with its complementary sequence, is different from the signal, as generated when not hybridizing with its complementary sequence. However, in some preferred embodiments, at least one of the reporter group and the quencher group is located at the end (e.g. 5' or 3' end) of the detection probe. In some preferred embodiments, one of the reporter group and the quencher group is located at 5' end or 1-10 nt from 5' end of the detection probe, and there is a suitable distance between the reporter group and the quencher group, so that before the detection probe hybridizes with its complementary sequence, the quencher group can absorb or quench the signal of the reporter group. In some preferred embodiments, one of the reporter group and the quencher group is located at 3' end or 1-10 nt from 3' end of the detection probe, and there is a suitable distance between the reporter group and the quencher group, so that before the detection probe hybridizes with its complementary sequence, the quencher group can absorb or quench the signal of the reporter group. In some preferred embodiments, the distance between the reporter group and the quencher group is a distance as defined above (e.g. a distance of 10-80 nt or longer). In some preferred embodiments, one of the reporter group and the quencher group is located at 5' end of the detection probe, and the other is located at 3' end.

In the method of the invention, said reporter group and said quencher group may be any suitable groups or molecules known in the art. Their particular examples include, but are not limited to Cy2™ (506), YOPRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), PyroninY (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YOPRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705), and Quasar 705 (610). The number contained in the parenthesis represents a maximal emission wavelength, with a unit of nm.

In addition, a variety of suitable combinations of the reporter group and the quencher group are known in the art, see, for example, Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, 2nd Edition (Academic Press, New York, 1971); Griffiths, Color AND Constitution of Organic Molecules (Academic Press, New York, 1976); Bishop, editor, Indicators (Peigamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, 6th Edition (Molecular Probes, Eugene, Oreg., 1996); U.S. Pat. Nos. 3,996,345 and 4,351,760.

In some preferred embodiments, said reporter group is a fluorescent group. In such embodiments, the signal generated by the reporter group is fluorescence, and, a quencher group is a molecule or group capable of absorbing/quenching the fluorescence (e.g. another fluorescent molecule can absorb the fluorescence, or a quencher can quench the fluorescence). In some preferred embodiments, said fluorescent group includes, but is not limited to various fluorescent molecules, for example, ALEX-350, FAM, VIC, TET, CAL Fluor® Gold 540, JOE, HEX, CAL Fluor Orange 560, TAMRA, CAL Fluor Red 590, ROX, CAL Fluor Red 610, TEXAS RED, CAL Fluor Red 635, Quasar 670, CY3, CY5, CY5.5, Quasar 705, etc. In some preferred embodiments, said quencher group includes, but is not limited to various quenchers, for example, DABCYL, BHQ (e.g. BHQ-1 or BHQ-2), ECLIPSE, and/or TAMRA, etc.

In the method of the invention, the detection probe can also be modified, for example, so as to have resistance against nuclease activity (e.g. 5' nuclease activity, for example, 5' to 3' nucleic acid exonuclease activity). For example, a modification resistant to nuclease activity can be introduced into the main chain of the detection probe, for example, phosphorothioate bond, alkyl phosphate triester bond, aryl phosphate triester bond, alkyl phosphonate bond, aryl phosphonate bond, hydrogenated phosphate bond, alkyl phosphoramidate bond, aryl phosphoramidate bond, 2'-O-aminopropyl modification, 2'-0-alkyl modification, 2'-0-allyl modification, 2'-0-butyl modification, and 1-(4'-thio-PD-ribofuranosyl) modification.

In the method of the invention, the detection probe may be linear, or have a hairpin structure. In some preferred embodiments, said detection probe is linear. In some preferred embodiments, said detection probe has a hairpin structure. A hairpin structure can be naturally occurring, or can be artificially introduced. In addition, the detection probe having a hairpin structure can be constructed by conventional methods in the art. For example, two complementary oligonucleotide sequences can be added to the two ends (5' end and 3' end) of the detection probe, to enable the detection probe to form a hairpin structure. In such embodiments, the two complementary oligonucleotide sequences form the arm (stem) of a hairpin structure. The arm of the hairpin structure may have any desired length, for example, the length of the arm may be 2-15 nt, for example, 3-7 nt, 4-9 nt, 5-10 nt, 6-12 nt.

In addition, in the method of the invention, "hybridize", "nucleic acid hybridization" and "a condition that allows nucleic acid hybridization" in Step (3) may have the same meanings as defined above.

The product in Step (3) and a nucleic acid polymerase are used to carry out Step (4). In Step (4), under a condition that allows extension reaction of a nucleic acid polymerase, the nucleic acid polymerase will use the detection probe as a template, to extend the mediator fragment hybridized to the detection probe, thereby forming a duplex.

As described above in detail, each mediator probe comprises a unique mediator sequence, and in the presence of an enzyme having 5' nuclease activity, releases a mediator fragment comprising the unique mediator sequence or a part thereof. Later, each mediator fragment is hybridized to the detection probe at a different position (i.e. a capture sequence complementary to the corresponding mediator sequence or a part thereof), is extended by a nucleic acid polymerase, and for a duplex with the detection probe. Therefore, for each mediator probe, when its corresponding target sequence is present, a unique duplex will be produced in Step (4), which comprises the detection probe (as a strand) and an extension product of the mediator fragment (as another strand) corresponding to the mediator probe. Therefore, each duplex produced in Step (4) has a different structure (sequence), and thus has a different $T_m$ value, and shows a different melting peak in melting curve analysis.

In some preferred embodiments, the nucleic acid polymerase used in Step (4) is a template-dependent nucleic acid polymerase (e.g. DNA polymerase, particularly a thermally stable DNA polymerase). In some preferred embodiments, the nucleic acid polymerase is a thermally stable DNA polymerase, which can be obtained from various bacteria, for example, *Thermus aquaticus* (Taq), *Thermus thermophiles* (Tth), *Thermus filiformis, Thermis flavus, Thermococcus literalis, Thermus antranildanii, Thermus caldophllus, Thermus chliarophilus, Thermus flavus, Thermus igniterrae, Thermus lacteus, Thermus oshimai, Thermus ruber, Thermus rubens, Thermus scotoductus, Thermus silvanus, Thermus thermophllus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus woesei, Pyrococcus horikoshii, Pyrococcus abyssi, Pyrodictium occultum, Aquifexpyrophilus and Aquifex aeolieus*. Preferably, the template-dependent nucleic acid polymerase is Taq polymerase.

In some preferred embodiments, the enzyme having 5' nuclease activity used in Step (2) is a nucleic acid polymerase having 5' nuclease activity, and is the same as the nucleic acid polymerase as used in Step (4). In some preferred embodiments, the enzyme having 5' nuclease activity used in Step (2) is different from the nucleic acid polymerase used in Step (4).

For example, in some embodiments, in Step (2), a first nucleic acid polymerase is used to catalyze the extension of the upstream oligonucleotide sequence, and an enzyme having 5' nuclease activity is used to catalyze the cleavage of the mediator probe, and then in Step (4), a second nucleic acid polymerase is used to catalyze the extension of the mediator fragment. In some embodiments, in Step (2), a first nucleic acid polymerase having 5' nuclease activity is used to catalyze the extension of the upstream oligonucleotide sequence and the cleavage of the mediator probe, and then in Step (4), a second nucleic acid polymerase is used to catalyze the extension of the mediator fragment. However, particularly preferred, the same enzyme is used in Steps (2) and (4). For example, a template-dependent nucleic acid polymerase having 5' nuclease activity (e.g. a DNA polymerase, particularly a thermally stable DNA polymerase) can be used to catalyze the extension of the upstream oligonucleotide sequence and the cleavage of the mediator probe in Step (2), and catalyze the extension of the mediator fragment in Step (4).

In the method of the invention, one or more of Steps (1)-(4) may be repeated according to practical need. In some preferred embodiments, Steps (1)-(2) are repeated one or more times, and before each repetition, the step of nucleic acid denaturation is carried out once. It is easy to understand that by repeating Steps (1)-(2), more mediator fragments can be produced, which are used in the subsequent steps (i.e. Step (3)-(5)). Therefore, in some preferred embodiments, the method of the invention is carried out by the following solutions: Steps (1)-(2) are repeated one or more times, and before each repetition, the step of nucleic acid denaturation is carried out once; and then Steps (3)-(5) are carried out.

In some preferred embodiments, Steps (1)-(4) are repeated one or more times, and before each repetition, the step of nucleic acid denaturation is carried out once. It is easy to understand that by repeating Steps (1)-(4), more duplexes comprising the detection probe and the extension product of the mediator fragment can be produced, which are used in the subsequent step (i.e. Step (5)). Therefore, in some preferred embodiments, the method of the invention is carried out by the following solutions: Steps (1)-(4) are repeated one or more times, and before each repetition, the step of nucleic acid denaturation is carried out once; and then Step (5) is carried out.

In some preferred embodiments, Steps (1)-(4) of the method of the invention can be carried out by a process comprising the following Steps (a)-(f):

(a) providing a detection probe, and for each target nucleic acid sequence to be detected, providing an upstream oligonucleotide sequence, a mediator probe and a downstream oligonucleotide sequence; and, optionally, providing a common primer; wherein, said detection probe, said mediator probe, said upstream oligonucleotide sequence, said downstream oligonucleotide sequence and said common primer are as defined above;

(b) mixing a sample to be detected with the detection probe, the upstream oligonucleotide sequence, the mediator probe and the downstream oligonucleotide sequence as provided, and a template-dependent nucleic acid polymerase having 5' nuclease activity (e.g. a DNA polymerase, particularly a thermally stable DNA polymerase); and optionally, adding the common primer;

(c) under a condition that allows nucleic acid denaturation, incubating the product in the previous step;

(d) under a condition that allows nucleic acid annealing or hybridization, incubating the product in the previous step;

(e) under a condition that allows nucleic acid extension, incubating the product in the previous step; and (f) optionally, repeating Steps (c)-(e) one or more times.

In such embodiments, in Step (c), all the nucleic acid molecules in the sample are dissociated into single strands; later, in Step (d), complementary nucleic acid molecules (e.g. the upstream oligonucleotide sequence and the target nucleic acid sequence or the extension product of the downstream oligonucleotide sequence; the downstream oligonucleotide sequence and the target nucleic acid sequence or the extension product of the upstream oligonucleotide sequence; the mediator probe and the target nucleic acid sequence or an amplification product thereof; the mediator probe or the mediator fragment resulted from the cleavage of the mediator probe and the detection probe; the common primer and the upstream/downstream oligonucleotide sequence or the extension product of the upstream/downstream oligonucleotide sequence) would be annealed or hybridized, to form a duplex; later, in Step (e), the template-dependent nucleic acid polymerase having 5' nuclease activity will extend the upstream/downstream oligonucleotide sequence hybridized to the target nucleic acid sequence, cleave the free 5' end of the mediator probe hybridized to the target nucleic acid sequence, extend the mediator fragment hybridized to the detection probe, extend the common primer hybridized to the extension product of the upstream/downstream oligonucleotide sequence. Therefore, by circulation of Steps (c)-(e), the amplification of the target nucleic acid sequence, the cleavage of the mediator probe, and the formation of the duplex comprising the detection probe and the extension product of the mediator fragment can be accomplished, so as to accomplish Steps (1)-(4) of the method of the invention.

It is easy to understand that a nucleic acid polymerase will not extend the mediator probe hybridized to the detection probe, as the target specific sequence at 3' end of the mediator probe cannot hybridize with the detection probe, and is in a free state. In addition, preferably, the mediator probe is blocked at 3' end, so as to avoid the undesired extension of the mediator probe, for example, avoid the extension of the mediator probe hybridized to the target nucleic acid sequence or the detection probe.

The incubation time and temperature in Step (c) can be conventionally determined by a person skilled in the art. In some preferred embodiments, in Step (c), the product in Step (b) is incubated at a temperature of 80-105° C. (e.g. 80-85° C., 85-90° C., 90-95° C., 91° C., 92° C., 93° C., 94° C., 95° C., 96° C., 97° C., 98° C., 99° C., 100° C., 101° C., 102° C., 103° C., 104° C., or 105° C.), so as to denaturize nucleic acids. In some preferred embodiments, in Step (c), the product in Step (b) is incubated for 10 s-5 min, for example, 10-20 s, 20-40 s, 40-60 s, 1-2 min, or 2-5 min.

The incubation time and temperature in Step (d) can be conventionally determined by a person skilled in the art. In some preferred embodiments, in Step (d), the product in Step (c) is incubated at a temperature of 35-70° C. (e.g. 35-40° C., 40-45° C., 45-50° C., 50-55° C., 55-60° C., 60-65° C., or 65-70° C.), so as to allow nucleic acid annealing or hybridization. In some preferred embodiments, in Step (d), the product in Step (c) is incubated for 10 s-5 min, for example, 10-20 s, 20-40 s, 40-60 s, 1-2 min, or 2-5 min.

The incubation time and temperature in Step (e) can be conventionally determined by a person skilled in the art. In some preferred embodiments, in Step (e), the product in Step (d) is incubated at a temperature of 35-85° C. (e.g. 35-40° C., 40-45° C., 45-50° C., 50-55° C., 55-60° C., 60-65° C., 65-70° C., 70-75° C., 75-80° C., 80-85° C.), so as to allow nucleic acid extension. In some preferred embodiments, in Step (e), the product in Step (d) is incubated for 10 s-30 min, for example, 10-20 s, 20-40 s, 40-60 s, 1-2 min, 2-5 min, 5-10 min, 10-20 min or 20-30 min.

In some embodiments, Steps (d) and (e) can be carried out at different temperatures, i.e. nucleic acid annealing and extension are carried out at different temperatures. In some embodiments, Steps (d) and (e) are at the same temperature, i.e. nucleic acid annealing and extension are carried out at the same temperature. In this case, Steps (d) and (e) can be combined as one step.

In the method of the invention, Steps (c)-(e) can be repeated at least once, for example, at least 2 times, at least 5 times, at least 10 times, at least 20 times, at least 30 times, at least 40 times, or at least 50 times. In some cases, it is advantageous to repeat Steps (c)-(e) more than one time, as it can amplify the target nucleic acid sequence, and enhance the sensitivity of the detection. However, it is easy to understand that when Steps (c)-(e) are repeated one or more times, the conditions used in Steps (c)-(e) in each cycle are not necessarily the same. For example, a certain condition can be used to carry out Steps (c)-(e) in the first five cycles, and then another condition can be used to carry out Steps (c)-(e) in the remaining cycles.

Step (5)

In Step (5) of the method of invention, the product in Step (4) is subjected to melting curve analysis; and according to the result of melting curve analysis, whether said n target nucleic acid sequences are present in said sample, is determined.

As described above, a detection probe labeled with a reporter group and a quencher group can be used to carry out melting curve analysis.

In some embodiments, the product in Step (4) can be heated gradually, and the signal generated by the reporter group of the detection probe is real-time monitored, so as to obtain the curve in which the signal intensity of the product in Step (4) changes with the change in temperature. For example, the product in Step (4) can be heated gradually from a temperature of 45° C. or lower (e.g. no more than 45° C., no more than 40° C., no more than 35° C., no more than 30° C., no more than 25° C.) to a temperature of 75° C. or higher (e.g. at least 75° C., at least 80° C., at least 85° C., at least 90° C., at least 95° C.), and the signal generated by the reporter group of the detection probe is real-time monitored, so as to obtain a curve in which the signal intensity of the reporter group changes with the change in temperature. The heating rate can be conventionally determined by a person skilled in the art. For example, the heating rate can be: the temperature is increased by 0.01-1° C. per step (e.g. 0.01-0.05° C., 0.05-0.1° C., 0.1-0.5° C., 0.5-1° C., 0.04-0.4° C., for example, 0.01° C., 0.02° C., 0.03° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.), and it retains for 0.5-15 s per step (e.g. 0.5-1 s, 1-2 s, 2-3 s, 3-4 s, 4-5 s, 5-10 s, 10-15 s); or the temperature is increased by 0.01-1° C. per second (e.g. 0.01-0.05° C., 0.05-0.1° C., 0.1-0.5° C., 0.5-1° C., 0.04-0.4° C., for example, 0.01° C., 0.02° C., 0.03° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.).

In some embodiments, the product in Step (4) can be gradually cooled, and the signal generated by the reporter group of a detection probe is real-time monitored, so as to obtain a curve the signal intensity of the product in Step (4) changes with the change in temperature. For example, the product in Step (4) can be gradually cooled from a temperature of 75° C. or higher (e.g. at least 75° C., at least 80° C., at least 85° C., at least 90° C., at least 95° C.) to a temperature of 45° C. or lower (e.g. no more than 45° C., no more than 40° C., no more than 35° C., no more than 30° C., no more than 25° C.), and the signal generated by the reporter group of the detection probe is real-time monitored, so as to obtain a curve in which the signal intensity of the reporter group changes with the change in temperature. The cooling rate can be conventionally determined by a person skilled in the art. For example, the cooling rate can be: the temperature is decreased by 0.01-1° C. per step (e.g. 0.01-0.05° C., 0.05-0.1° C., 0.1-0.5° C., 0.5-1° C., 0.04-0.4° C., for example, 0.01° C., 0.02° C., 0.03° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.), and it retains for 0.5-15 s per step (e.g. 0.5-1 s, 1-2 s, 2-3 s, 3-4 s, 4-5 s, 5-10 s, 10-15 s); or the temperature is decreased by 0.01-1° C. per second (e.g. 0.01-0.05° C., 0.05-0.1° C., 0.1-0.5° C., 0.5-1° C., 0.04-0.4° C., for example, 0.01° C., 0.02° C., 0.03° C., 0.04° C., 0.05° C., 0.06° C., 0.07° C., 0.08° C., 0.09° C., 0.1° C., 0.2° C., 0.3° C., 0.4° C., 0.5° C., 0.6° C., 0.7° C., 0.8° C., 0.9° C. or 1.0° C.).

Later, the curve obtained can be subjected to derivation, so as to obtain the melting curve of the product in Step (4). According to the melting peak (melting point) in the melting curve, the presence of the mediator fragment corresponding to the melting peak (melting point) can be determined. Later, according to the correspondence relationship between the mediator sequence of the mediator fragment and the target nucleic acid sequence, the presence of the target nucleic acid sequence corresponding to said mediator fragment can be determined.

For example, when the result of melting curve analysis shows the presence or absence of the melting peak corresponding to a first duplex comprising the detection probe and the extension product of a first mediator fragment, it can be determined that a first target nucleic acid sequence is present or absent in said sample. Similarly, when the result of melting curve analysis shows the presence or absence of the melting peak corresponding to a second duplex comprising the detection probe and the extension product of a second mediator fragment, it can be determined that a second target nucleic acid sequence is present or absent in said sample. When the result of melting curve analysis shows the presence or absence of the melting peak corresponding to a third duplex comprising the detection probe and the extension product of a third mediator fragment, it can be determined that a third target nucleic acid sequence is present or absent in said sample. When the result of melting curve analysis shows the presence or absence of the melting peak corresponding to a fourth duplex comprising the detection probe and the extension product of a fourth mediator fragment, it can be determined that a fourth target nucleic acid sequence is present or absent in said sample. Therefore, by using one detection probe and at least two (e.g. 2, 3, 4, 5, 6, 7, 8, 9, 10, 11, 12, 13, 14, 15, 16, 17, 18, 19, 20 or more) mediator probes, the method of the invention can achieve the simultaneous detection (multi-detection) of at least 2 (e.g. 2, 3, 4, 5, 6, 7, 8, 9, 10, 11, 12, 13, 14, 15, 16, 17, 18, 19, 20 or more) target nucleic acid sequences.

Without restriction by theory, the resolution or accuracy of melting curve analysis can reach 0.5° C. or higher. In other words, melting curve analysis can discriminate two melting peaks, the melting points of which are different from each other by only 0.5° C. or lower (e.g. 0.1° C., 0.2° C., 0.3° C., 0.4° C., 0.5° C.). Therefore, in some embodiments of the method of the invention, the difference in melting points between any two duplexes (e.g. a first duplex and a second duplex) can be at least 0.5° C. (e.g. by designing the sequences of a first mediator sequence, a second mediator sequence and a detection probe), so that said any two duplexes (e.g. a first duplex and a second duplex) can be discriminated and distinguished by melting curve analysis. However, for the convenience of discriminating and distinguishing one from another, a greater difference in melting points between two duplexes (e.g. a first duplex and a second duplex) is preferred under some situations. Therefore, in some embodiments of the method of the invention, the difference in melting points between two duplexes (e.g. a first duplex and a second duplex) may be any desired value (e.g. at least 0.5° C., at least 1° C., at least 2° C., at least 3° C., at least 4° C., at least 5° C., at least 8° C., at least 10° C., at least 15° C., or at least 20° C.), as long as the difference in the melting points can be discriminated and distinguished by melting curve analysis.

Simultaneous Use of One or More Detection Probes

In the method as described above, one detection probe is used to achieve multiplex detection of multiple target nucleic acid sequences. However, it is easy to understand that the invention is not limited to the number of the detection probes used. The method of the invention can use one or more detection probes (e.g. at least 1, at least 2, at least 3, at least 4, at least 5, at least 6, or more detection probes). Moreover, based on the same principle as described above, at least two or more (e.g. 2, 3, 4, 5, 6, 7, 8, 9, 10, 11, 12, 13, 14, 15, 16, 17, 18, 19, 20, or more detection probes) mediator probes can be designed for each detection probe. Therefore, the method of the invention can be used in simultaneous detection of multiple target nucleic acid sequences, and the maximal number of target nucleic acid sequences, which can be simultaneously detected by the method of the invention, is much greater than the number of the detection probes used, and is equal to the sum of the number of mediator probes designed for each detection probe (i.e. the number of all the mediator probes used). In addition, it is easy to understand that one or more mediator probes can be designed for each target nucleic acid sequence. Therefore, the actual number of target nucleic acid sequences, which can be simultaneously detected by the method of the invention, can be equal to or less than the number of all the mediator probes used, but still greater than the number of the detection probes used.

Therefore, in some embodiments, the invention provides a method for detecting the presence of n target nucleic acid sequences in a sample, wherein, n is an integer of ≥2 (e.g. n is an integer of 2, 3, 4, 5, 6, 7, 8, 9, 10, 11, 12, 13, 14, 15, 16, 17, 18, 19, 20, 25, 30, 35, 40 or greater), and, said method comprises the following steps:

(1) for each target nucleic acid sequence to be detected, providing at least one upstream oligonucleotide sequence and at least one mediator probe; wherein, said upstream oligonucleotide sequence comprising a sequence complementary to said target nucleic acid sequence; and, said mediator probe comprises in 5' to 3' direction, a mediator sequence and a target specific sequence, said mediator sequence comprises a sequence not complementary to said target nucleic acid sequence, and, said target specific sequence comprising a sequence complementary to said target nucleic acid sequence; and, when hybridizing with said target nucleic acid sequence, said upstream oligonucleotide sequence is located upstream of said target specific sequence; and, the mediator sequences comprised in all the mediator probes are different from each other;

and, under a condition that allows nucleic acid hybridization, contacting the sample with the upstream oligonucleotide sequence and the mediator probe as provided;

(2) under a condition that allows cleavage of mediator probes, contacting the product in Step (1) with an enzyme having 5' nuclease activity;

(3) providing m detection probes, and under a condition that allows nucleic acid hybridization, contacting the product in Step (2) with said m detection probes, wherein, m is an integer less than n and greater than 0, and each detection probe independently comprises in 3' to 5' direction, one or more capture sequences complementary to one or more mediator sequences or parts thereof, and a templating sequence (templating sequence); and, said m detection probes comprise a plurality of (e.g. at least n) capture sequences, which are complementary to the mediator sequence or a part thereof of each mediator probe provided in Step (1), respectively; and, each detection probe is independently labeled with a reporter group and a quencher group, wherein, said reporter group can generate a signal, and, said quencher group can absorb or quench the signal generated by said reporter group; and, the signal, as generated by each detection probe when hybridizing with its complementary sequence, is different from the signal, as generated when not hybridizing with its complementary sequence; and, (4) under a condition that allows extension reaction of a nucleic acid polymerase, contacting the product in Step (3) with a nucleic acid polymerase;

(5) subjecting the product in Step (4) to melting curve analysis; and according to the result of melting curve analysis, determining whether each target nucleic acid sequence is present in said sample.

In Step (1) of such embodiments, when a certain target nucleic acid sequence is present, both the upstream oligonucleotide sequence corresponding to the target nucleic acid sequence (i.e. the upstream oligonucleotide sequence comprising a sequence complementary to the target nucleic acid sequence), and the mediator probe corresponding to the target nucleic acid sequence (i.e. a mediator probe, the target specific sequence of which comprise a sequence complementary to the target nucleic acid sequence) hybridize with the target nucleic acid sequence.

Further, in Step (2) of such embodiments, when a certain target nucleic acid sequence is present, both the upstream oligonucleotide sequence and the mediator probe corresponding to the target nucleic acid sequence hybridize with the target nucleic acid sequence, however, the mediator sequence in said mediator probe is in a free state, and does not hybridize with the target nucleic acid sequence. In such a case, in the presence of an enzyme having 5' nuclease activity, the mediator sequence or a part thereof in said mediator probe (a mediator probe corresponding to the target nucleic acid sequence) is cleaved off from said mediator probe due to the presence of the upstream oligonucleotide sequence (corresponding to the target nucleic acid sequence) or an extension product thereof, and form a mediator fragment corresponding to the target nucleic acid sequence.

Further, in Step (3) and (4) of such embodiments, when a mediator fragment corresponding to a certain target nucleic acid sequence is present, said mediator fragment hybridizes with a complementary detection probe (i.e. a detection probe comprising a capture sequence complementary to the mediator sequence or a part thereof in the mediator fragment), and, said nucleic acid polymerase will use said complementary detection probe as a template, to extend said mediator fragment, and form a duplex corresponding to said target nucleic acid sequence.

It is easy to understand that in the method of the invention, m detection probes comprise a plurality of capture sequences, and the collection of said plurality of capture sequences covers the complementary sequences of the mediator sequences or parts thereof in all the mediator probes provided in Step (1). Therefore, said m detection probes or said plurality of capture sequences can "capture" the mediator fragment cleaved from any mediator probe. That is, any mediator fragment cleaved from a mediator probe can hybridize with at least one detection probe or at least one capture sequence.

Furthermore, in Step (5) of such embodiments, when the melting peak of the duplex corresponding to a certain target nucleic acid sequence is detected or not, it is determined that said target nucleic acid sequence is present or absent in said sample.

In some embodiments, in Step (1), for each target nucleic acid sequence to be detected, at least one (or more) mediator probe is provided. Therefore, in Step (1), n (or more) mediator probes are provided, each of which is provided for a target nucleic acid sequence; later, in Step (3), said m detection probes comprise n (or more) capture sequences, which are complementary to the mediator sequences or parts thereof of n (or more) mediator probes provided in Step (1), respectively; therefore, any mediator fragment produced in Step (2) can hybridize with at least one detection probe (comprising a capture sequence complementary to the mediator sequence or a part thereof in the mediator fragment), and form a duplex, which is used in the subsequent extension and detection. In some preferred embodiments, said m detection probes comprise n capture sequences, which are complementary to the mediator sequences or parts thereof of n mediator probes, respectively.

In some preferred embodiments, said m detection probes do not comprise an identical capture sequence. In this case, for each mediator probe, there is one and only one detection probe (comprising a capture sequence complementary to the mediator sequence in the mediator probe) that hybridizes with the mediator fragment the derived from the mediator probe, and after the extension reaction, only one duplex is produced. Later, by detecting the presence of the duplex in Step (5), the presence of the target nucleic acid sequence corresponding to said mediator probe can be determined.

In some preferred embodiments, said m detection probes can comprise an identical capture sequence. In this case, for each mediator probe, there may be one or more detection probes (comprising a capture sequence complementary to the mediator sequence in the mediator probe) that hybridize with the mediator fragment derived from the mediator probe, and after the extension reaction, one or more duplexes are produced. Later, by detecting the presence of one or more duplexes in Step (5), the presence of the target nucleic acid sequence corresponding to said mediator probe can be determined.

In Step (5) of such embodiments, the melting point of the duplex and/or the reporter group of the detection probe can be used to discriminate and distinguish the duplexes. In some preferred embodiments, said m detection probes comprise identical reporter group. In this case, the product in Step (4) can be subjected to melting curve analysis, and according to melting peaks (melting points) in the melting curve, the presence of a certain duplex can be determined, and the presence of the target nucleic acid sequence corresponding to the duplex can be further determined. In some preferred embodiments, the reporter groups comprised in said m detection probes are different from each other. In this case, when the product in Step (4) is subjected to melting curve analysis, the signal of each reporter group can be real-time monitored, thereby obtaining multiple melting curves, each of which corresponding to the signal of one reporter group. Later, according to the signal type of the reporter group and the melting peaks (melting points) in the melting curve, the presence of a certain duplex can be determined, and the presence of the target nucleic acid sequence corresponding to the duplex can be further determined.

In some exemplary embodiments, at least 1, at least 2, at least 3, at least 4, at least 5, at least 6, at least 8, at least 10 detection probes (i.e. m is an integer of $\geq 1$, $\geq 2$, $\geq 3$, $\geq 4$, $\geq 5$, $\geq 6$, $\geq 8$, $\geq 10$) can be used. In some exemplary embodiments, 1-10 detection probes (i.e. m is an integer of 1-10; for example, m is 1, 2, 3, 4, 5, 6, 7, 8, 9 or 10) can be used. Further preferably, the detection probes used are independently labeled with identical or different reporter groups.

For example, in some exemplary embodiments, the method of the invention may use a first and a second detection probe, which are labeled with a first reporter group and a second reporter group, respectively. Therefore, in Step (5), the signals of the first reporter group and the second the reporter group are real-time monitored with the change in temperature, so as to obtain a first melting curve and a second melting curve. Later, according to the melting peak in the first (or the second) melting curve, the presence of the duplexes comprising the first (or the second) detection probe can be determined, and the presence of the target nucleic acid sequence, which corresponds to the mediator fragment hybridized with the first (or the second) detection probe, can be further determined.

In some exemplary embodiments, the method of the invention uses at least 1, at least 2, at least 3, at least 4, at least 5, at least 6, at least 8, or at least 10 detection probes; and, at least 2, at least 3, at least 4, at least 5, at least 6, at least 8, at least 10, at least 15, at least 20, at least 25, at least 30, at least 35, at least 40, at least 45 mediator probes. Therefore, the method of the invention can achieve simultaneous detection (multi-detection) of multiple target nucleic acid sequences, wherein the maximal number of the target nucleic acid sequences that can be detected, is equal to the number of the mediator probes used. For example, in Example 6 of the present application, the method of the invention uses 3 detection probes and 20 mediator probes, and achieves simultaneous detection (20-plex detection) of 20 target nucleic acid sequences.

It is also easy to understand that the technical features, which are described in detail for the method using one detection probe, can also be applied to the method using two or more detection probes. For example, the detailed description, as made above to a sample to be detected, a target nucleic acid sequence, a mediator probe, an upstream oligonucleotide sequence, a downstream oligonucleotide sequence, a common primer, a detection probe, a condition that allows nucleic acid hybridization, a condition that allows the cleavage of a mediator probe, an enzyme having 5' nuclease activity, a condition that allows extension reaction of a nucleic acid polymerase, a nucleic acid polymerase, melting curve analysis, repetition of steps, and the like, can be applied to the method using two or more detection probes. Therefore, in some preferred embodiments, the method of the invention using two or more detection probes can involve any one or more technical features as described above in detail, or any combination of said technical features.

For example, as described above, according to practical need, one or more steps of Steps (1)-(4) may be repeated. In some preferred embodiments, Steps (1)-(2) are repeated one or more times, and before each repetition, the step of nucleic acid denaturation is carried out once. It is easy to understand that the repetition of Steps (1)-(2) can produce more mediator fragments, which are used in subsequent steps (i.e. Step (3)-(5)). Therefore, in some preferred embodiments, the method of the invention is carried out by the following solutions: Steps (1)-(2) are repeated one or more times, and before each repetition, the step of nucleic acid denaturation is carried out once; and then Steps (3)-(5) are carried out.

In some preferred embodiments, Steps (1)-(4) are repeated one or more times, and before each repetition, the step of nucleic acid denaturation is carried out once. It is easy to understand that the repetition of Steps (1)-(4) can produce more duplexes comprising the detection probe and the extension product of the mediator fragment, which are used in subsequent steps (i.e. Step (5)). Therefore, in some preferred embodiments, the method of the invention is carried out by the following solutions: Steps (1)-(4) are repeated one or more times, and before each repetition, the step of nucleic acid denaturation is carried out once; and then Step (5) is carried out.

In some preferred embodiments, Steps (1)-(4) of the method of the invention can be carried out by a process comprising the following Steps (a)-(f):
(a) providing m detection probes, and for each target nucleic acid sequence to be detected, providing an upstream oligonucleotide sequence, a mediator probe and a downstream oligonucleotide sequence; and, optionally, providing a common primer; wherein, said detection probe, said mediator probe, said upstream oligonucleotide sequence, said downstream oligonucleotide sequence and said common primer are as defined above;
(b) mixing a sample to be detected with the detection probe, the upstream oligonucleotide sequence, the mediator probe and the downstream oligonucleotide sequence as provided, and a template-dependent nucleic acid polymerase having 5' nuclease activity (e.g. a DNA polymerase, particularly a thermally stable DNA polymerase); and optionally, adding the common primer;
(c) under a condition that allows nucleic acid denaturation, incubating the product in the previous step;
(d) under a condition that allows nucleic acid annealing or hybridization, incubating the product in the previous step;
(e) under a condition that allows nucleic acid extension, incubating the product in the previous step; and
(f) optionally, repeating Steps (c)-(e) one or more times.

With respect to Step (a)-(f), they have already been described above in detail.

Optional Step (6) and Quantitative/Semi-Quantitative Detection

The method of the invention can not only be used in qualitative detection of a target nucleic acid sequence, but also be used in quantitative or semi-quantitative detection of a target nucleic acid sequence. It is easy to understand that the higher the amount of a certain target nucleic acid sequence in a sample is, in Step (1), the more mediator probes hybridize with said target nucleic acid sequence; further, in Step (2), more mediator probes are cleaved, and more mediator fragments are released; further, in Steps (3) and (4), there are also more mediator fragments that hybridize with the detection probe, and more duplexes are produced due to extension reaction; further, in Step (5), more duplexes can be used in melting curve analysis, the signal thus produced is stronger, and the height of the melting peak is higher. Therefore, according to the relative height of the melting peak, the amount/level of the corresponding target nucleic acid sequence in the sample (quantitative or semi-quantitative detection) can be determined. Therefore, the method of the invention can not only detect the presence of two or more target nucleic acid sequences in a sample, but also be used to detect the level of said two or more target nucleic acid sequences in the sample.

Therefore, in some preferred embodiments, the method of the invention further comprises the following steps:
(6) according to the result of melting curve analysis (particularly the peak height of the melting peak in the melting curve), determining the level of the target nucleic acid sequence corresponding to the melting peak.

Probe Set and Kit

In another aspect, the invention provides a probe set, comprising one detection probe, and at least two mediator probes, wherein, said mediator probe each independently comprises in 5' to 3' direction, a mediator sequence and a target specific sequence, said target specific sequence comprises a sequence complementary to a target nucleic acid sequence, said mediator sequence comprises a sequence not complementary to said target nucleic acid sequence, and, the mediator sequences comprised in all the mediator probes are different from each other; and said detection probe comprises in 3' to 5' direction, capture sequences complementary to each mediator sequence or a part thereof, and a templating sequence; and, said detection probe is labeled with a reporter group and a quencher group, wherein, said reporter group can generate a signal, and, said quencher group can absorb or quench the signal generated by said reporter group; and, the signal, as generated by said detection probe when hybridizing with its complementary sequence, is different from the signal, as generated when not hybridizing with its complementary sequence.

In some preferred embodiments, said probe set comprises at least 2, at least 3, at least 4, at least 5, at least 6, at least 7, at least 8, at least 9, at least 10, at least 12, at least 15, or at least 20 mediator probes. Preferably, said mediator probe (or the target specific sequence comprised therein) targets to 2, 3, 4, 5, 6, 7, 8, 9, 10 or more target nucleic acid sequences. In some preferred embodiments, said probe set comprises 1 detection probe, and 2-6 (e.g. 2, 3, 4, 5 or 6) mediator probes. Therefore, said probe set can be used to detect 2-6 (e.g. 2, 3, 4, 5 or 6) target nucleic acid sequences simultaneously.

In some preferred embodiments, all the mediator probes each target to different target nucleic acid sequences. In some preferred embodiments, the mediator sequences comprised in all the mediator probes are different from each other; and, the target specific sequences comprised in all the mediator probes are different from each other.

It is easy to understand that such probe sets can be used to carry out the method of the invention as described above in detail. Therefore, the technical features of a mediator probe and a detection probe as described in detail above can also be applied to the mediator probe and the detection probe in the probe set. Therefore, in some preferred embodiments, said probe set comprises mediator probes as defined above. In some preferred embodiments, said probe set comprises detection probes as defined above.

In some preferred embodiments, said probe set further comprises, an upstream oligonucleotide sequence as defined above. For example, for each target nucleic acid sequence and each mediator probe, an upstream oligonucleotide sequence can be provided, and said upstream oligonucleotide sequence comprises a sequence complementary to said target nucleic acid sequence; and, when hybridizing with said target nucleic acid sequence, said upstream oligonucleotide sequence is located upstream to the target specific sequence of said mediator probe.

In some preferred embodiments, said probe set further comprises, a downstream oligonucleotide sequence as defined above. For example, a downstream oligonucleotide sequence can be provided for each target nucleic acid sequence and mediator probe, said downstream oligonucleotide sequence comprises a sequence complementary to said target nucleic acid sequence; and, when hybridizing with said target nucleic acid sequence, said downstream oligonucleotide sequence is located downstream to the target specific sequence of said mediator probe.

In some preferred embodiments, said probe set further comprises a common primer as defined above. For example, in some preferred embodiments, said upstream oligonucleotide sequence and downstream oligonucleotide sequence comprise an identical oligonucleotide sequence at their 5' ends. Therefore, said probe set can further comprise a common primer, which has a sequence complementary to the identical oligonucleotide sequence.

In some preferred embodiments, said probe set further comprises an upstream oligonucleotide sequence and a downstream oligonucleotide sequence as defined above. In some preferred embodiments, said probe set further comprises an upstream oligonucleotide sequence, a downstream oligonucleotide sequence and a common primer as defined above.

In another aspect, the invention provides a kit comprising one or more probe sets as defined above.

In some preferred embodiments, said kit comprises at least 1, at least 2, at least 3, at least 4, at least 5, at least 6, at least 7, at least 8, at least 9, at least 10 probe sets.

In some preferred embodiments, all the mediator sequences in the kit each target to different target nucleic acid sequences. In some preferred embodiments, the mediator sequences comprised in all the mediator probes in the kit are different from each other. In some preferred embodiments, the target specific sequences comprised in all the mediator probes in the kit are different from each other.

In some preferred embodiments, all the detection probes in the kit comprise the same reporter groups. In some preferred embodiments, all the detection probes in the kit are independently labeled with identical or different reporter groups. In some preferred embodiments, the reporter groups comprised in all the detection probes in the kit are different from each other.

In some preferred embodiments, said kit comprises 1-6 probe sets. Preferably, the reporter groups comprised in all the detection probes in the kit are different from each other. Further preferably, in the kit, the mediator sequences comprised in all the mediator probes are different from each other, and, in the kit, the target specific sequences comprised in all the mediator probes are different from each other.

The present application further provides a kit comprising m detection probes and n mediator probes, wherein, n is an integer of ≥2 (e.g. n is an integer of 2, 3, 4, 5, 6, 7, 8, 9, 10, 11, 12, 13, 14, 15, 16, 17, 18, 19, 20, 25, 30, 35, 40 or greater), m is an integer less than n and greater than 0, and, each mediator probe independently comprises in 5' to 3' direction, a mediator sequence and a target specific sequence, said target specific sequence comprises a sequence complementary to a target nucleic acid sequence, said mediator sequence comprises a sequence not complementary to said target nucleic acid sequence, and, the mediator sequences comprised in all the mediator probes are different from each other; and each detection probe independently comprises in 3' to 5' direction, one or more capture sequences complementary to one or more mediator sequences or parts thereof, and a templating sequence; and, said m detection probes comprise a plurality of (e.g. at least n) capture sequences, which are complementary to the mediator sequence or a part thereof of each mediator probe, respectively; and, each detection probe is independently labeled with a reporter group and a quencher group, wherein, said reporter group can generate a signal, and, said quencher group can absorb or quench the signal generated by said reporter group; and, the signal, as generated by each detection probe when hybridizing with its complementary sequence, is different from the signal, as generated when not hybridizing with its complementary sequence.

In exemplary embodiments of the invention, m detection probes comprise a plurality of capture sequences, the collection of said plurality of capture sequences covers the complementary sequences of the mediator sequences or parts thereof in all the mediator probes in the kit. Therefore, said m detection probes or said plurality of capture sequences can "capture" the mediator fragment cleaved from any mediator probe. That is, any mediator fragment cleaved from mediator probes can hybridize with at least one detection probe or at least one capture sequence.

In some exemplary embodiments, said kit comprises at least 1, at least 2, at least 3, at least 4, at least 5, at least 6, at least 8, at least 10 detection probes (i.e. m is an integer of ≥1, ≥2, ≥3, ≥4, ≥5, ≥6, ≥8, ≥10). In some exemplary embodiments, said kit comprises 1-10 detection probes (i.e. m is an integer of 1-10; for example, m is 1, 2, 3, 4, 5, 6, 7, 8, 9 or 10). Further preferably, said detection probes each are labeled with an identical or different reporter group.

In some exemplary embodiments, said kit comprises at least 1, at least 2, at least 3, at least 4, at least 5, at least 6, at least 8, or at least 10 detection probes; and, at least 2, at least 3, at least 4, at least 5, at least 6, at least 8, at least 10, at least 15, at least 20, at least 25, at least 30, at least 35, at least 40, at least 45 mediator probes. Therefore, the kit can be used in simultaneous detection of multiple target nucleic acid sequences, wherein the maximal number of the target nucleic acid sequences to be detected is equal to the number of the mediator probes used.

For example, in some exemplary embodiments, said kit comprises 1 detection probes and 2-6 (e.g. 2, 3, 4, 5 or 6) mediator probes, which can be used to detect 2-6 (e.g. 2, 3, 4, 5 or 6) target nucleic acid sequences simultaneously. In some exemplary embodiments, said kit comprises 2 detection probes and 3-12 (e.g. 3, 4, 5, 6, 7, 8, 9, 10, 11, 12) mediator probes, which can be used to detect 3-12 target nucleic acid sequences simultaneously. In some exemplary embodiments, said kit comprises 3 detection probes and 4-18 (e.g. 5-10) mediator probes, which can be used to detect 4-18 (e.g. 5-10) target nucleic acid sequences simultaneously. In some exemplary embodiments, said kit comprises 4 detection probes and 5-24 (e.g. 6-12) mediator probes, which can be used to detect 5-24 (e.g. 6-12) target nucleic acid sequences simultaneously. In some exemplary embodiments, said kit comprises 5 detection probes and 6-30 (e.g. 8-15) mediator probes, which can be used to detect 6-30 (e.g. 8-15) target nucleic acid sequences simultaneously. In some exemplary embodiments, said kit comprises 6 detection probes and 7-36 (e.g. 10-18) mediator probes, which can be used to detect 7-36 (e.g. 10-18) target nucleic acid sequences simultaneously. In some exemplary embodiments, said kit comprises 7 detection probes and 8-42 (e.g. 12-20) mediator probes, which can be used to detect 8-42 (e.g. 12-20, for example, 19) target nucleic acid sequences simultaneously.

It is easy to understand that such a kit can be used to carry out the method of the invention as described above in detail. Therefore, the technical features of a mediator probe and a detection probe as described above in detail can also be applied to the mediator probe and the detection probe in a kit. Therefore, such a kit can further comprise other agents needed for carrying out the method of the invention.

For example, in some preferred embodiments, the kit further comprises an upstream oligonucleotide sequence, a downstream oligonucleotide sequence, a common primer, an enzyme having 5' nuclease activity, a nucleic acid polymerase, or any combination thereof, as defined above. In some preferred embodiments, the kit further comprises an agent for nucleic acid hybridization, an agent for cleavage of a mediator probe, an agent for nucleic acid extension, an agent for nucleic acid amplification, an agent for reverse transcription, or any combination thereof. Such agents can be conventionally determined by a person skilled in the art, and include, but are not limited to, an enzyme (e.g. a nucleic acid polymerase) working buffer, dNTPs, water, a solution comprising ions (e.g. $Mg^{2+}$), Single Strand DNA-Binding Protein (SSB), or any combination thereof. For example, an agent for reverse transcription include, but are not limited to a reverse transcriptase, working buffer for a reverse transcriptase, Oligo d(T), dNTPs, nuclease-free water, RNase inhibitor, or any combination thereof.

Use of Probe Sets

The present application further relates to the use of the probe set as defined above, in the manufacture of a kit for detecting the presence or level of said target nucleic acid sequence in a sample.

It is easy to understand that said probe set or kit can be used to carry out the method of the invention as detailed described above. Therefore, the technical features of a target nucleic acid sequence, a probe set, a kit, and the components comprised therein (e.g. a mediator probe, a detection probe, an upstream oligonucleotide sequence, a downstream oligonucleotide sequence, a common primer, an enzyme having 5' nuclease activity, a nucleic acid polymerase, an agent for nucleic acid hybridization, an agent for cleavage of a mediator probe, an agent for nucleic acid extension, an agent for nucleic acid amplification, an agent for reverse transcription, or any combination thereof) as described above in detail can also be applied here.

A person skilled in the art, based on the principle described in detail in the present application, can modify, replace or combine the technical features of the technical solutions in the invention, without departing from the spirit and scope of the invention. All such technical solutions and variants thereof are covered in the set of claims or an equivalent thereof in the present application.

Beneficial Effects of Invention

As compared with the prior art, the technical solutions of the invention have the following beneficial effects:

(1) The method of the invention can achieve simultaneous detection (multi-detection) of multiple target nucleic acid sequences by using only one labeled probe (i.e. a detection probe).

(2) The method of the invention can achieve simultaneous detection (multi-detection) of multiple target nucleic acid sequences, and the maximal number of the target nucleic acid sequences that can be detected simultaneously, is much greater than the number of the labeled probes (i.e. detection probes) used.

Therefore, the invention provides a simple, high-efficiency, low-cost multiplex detection method. The maximal number of target nucleic acid sequences that can be detected by the method of the invention is not limited to the number of the labeled probes (i.e. detection probes) used. That is, the method of the invention can achieve simultaneous detection (multi-detection) of significantly more target nucleic acid sequences, based on relatively limited number of labeled probes (i.e. detection probes), which is particularly advantageous.

The embodiments of the invention are described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantageous aspects of the invention are apparent for a person skilled in the art.

DESCRIPTION OF THE DRAWINGS

FIG. 1A illustrates exemplary embodiments in which 1 detection probe and 5 mediator probes are used to detect 5 target nucleic acid molecules. In the embodiments, a self-quenched detection probe (which carries a fluorescent group and quencher group) is provided, and an upstream primer (Upstream primers 1-5), a downstream primer (Downstream primers 1-5), and a mediator probe (Mediator probes 1-5) are designed and provided for each of the target nucleic acid molecules (T1-T5); wherein, the mediator probe each comprises a unique mediator sequence (Mediator sequences 1-5), which can hybridize with said detection probe. The hybridization position for each mediator sequence on a detection probe is unique, but there may be an overlapping region between them. For example, as shown in FIG. 1A, the hybridization position for Mediator sequence 1 on the detection probe partially overlaps with that for Mediator sequence 2, and the hybridization position for Mediator sequence 4 on the detection probe partially overlaps with that for Mediator sequence 5, while the hybridization position for Mediator sequence 3 on the detection probe does not overlap with those for other mediator sequences. During detection, 5 upstream primers, 5 downstream primers, and 5 mediator probes hybridized (annealed) with their corresponding target nucleic acid molecules, respectively; later, in the presence of a nucleic acid polymerase, all the upstream primer and downstream primers were extended, respectively, and due to the extension of each of the upstream primers (Upstream primer 1-5), the corresponding mediator probe (Mediator probes 1-5) was cleaved by an enzyme having 5' nuclease activity, so as to release a mediator fragment (Mediator fragments 1-5); later, Mediator fragments 1-5 hybridized to the detection probe at different positions, respectively, and were extended by a nucleic acid polymerase, so as to produce five extension products; the five extension products had different lengths, and together with the detection probe, formed five duplexes having different $T_m$ values. Therefore, by melting curve analysis, the presence of a duplex having a specific $T_m$ value can be determined, and the presence of the target nucleic acid molecules corresponding to the duplex can be further determined. Therefore, in the method of the invention, the detection of 5 target nucleic acid molecules can be achieved by using 1 detection probe and 5 mediator probes.

FIG. 1B illustrates exemplary embodiments in which 2 detection probes and 10 mediator probes were used to detect 10 target nucleic acid molecules (T1-T10). In the embodiments, two self-quenching detection probes (a first and second detection probe) are provided, each of which carries a different fluorescent group (fluorescent groups 1-2) and a different quencher group (Quencher groups 1-2); and, an upstream primer (Upstream primers 1-10), a downstream primer (Downstream primers 1-10), and a mediator probe (Mediator probe 1-10) are designed and provided for each target nucleic acid molecule (T1-T10); wherein, each mediator probe comprises a unique mediator sequence (Mediator sequences 1-10), and Mediator sequences 1-5 can hybridize with the first detection probe, and Mediator sequences 6-10 can hybridize with the second detection probe. The hybridization position for each mediator sequence on a detection probe is unique, but there may be an overlapping region between them. For example, as shown in FIG. 1B, the hybridization position for Mediator sequence 1 on the first detection probe partially overlaps with that for Mediator sequence 2, the hybridization position for Mediator sequence 4 on the first detection probe partially overlaps with that for Mediator sequence 5, the hybridization position for Mediator sequence 3 on the first detection probe does not hybridize with those for other mediator sequences; the hybridization position for Mediator sequence 6 on the second detection probe partially overlaps with that for Mediator sequence 7, the hybridization position for Mediator sequence 9 on the second detection probe partially overlaps with that for Mediator sequence 10, the hybridization position for Mediator sequence 8 on the second detection probe does not overlap with those for other mediator sequences. During the detection, 10 upstream primers, 10 downstream primers, 10 mediator probes hybridized (annealed) with their corresponding target nucleic acid molecules, respectively; later, in the presence of a nucleic acid polymerase, all the upstream primers and downstream primers were extended, respectively; and due to the extension of each upstream primer (Upstream primers 1-10), the corresponding mediator probe (Mediator probe 1-10) was cleaved by an enzyme having 5' nuclease activity, so as to release a mediator fragment (Mediator fragment 1-10); later, Mediator fragments 1-5 hybridized to the first detection probe at different positions, and were extended by a nucleic acid polymerase, so as to produce 5 extension products; the 5 extension products had different lengths, and together with the first detection probe, formed 5 duplexes having different $T_m$ values. Similarly, Mediator fragments 6-10 hybridized to the second detection probe at different positions, and were extended by a nucleic acid polymerase, so as to produce another 5 extension products; the 5 extension products had different lengths, and together with the second detection probe, formed another 5 duplexes having different $T_m$ values. Later, fluorescent groups (fluorescent group 1-2) on the first and second detection probe were used to carry out melting curve analysis, respectively, and the presence of a duplex having a specific $T_m$ value could be determined, and the presence of the target nucleic acid molecule corresponding to the duplex could be determined. Therefore, in the method of the invention, 2 detection probes and 10 mediator probes can be used to achieve the detection of 10 target nucleic acid molecules.

FIGS. 2A-2D show the amplification curves of 4 real-time PCRs using the mediator probe BRAF-MP1 and the liner fluorescent probe UP-L2, wherein, Reaction A uses Taq DNA polymerase having 5'→3' exonuclease activity and 200 nM mediator probe (FIG. 2A); Reaction B uses Taq DNA polymerase having 5'→3' exonuclease activity and 0 nM mediator probe (FIG. 2B); Reaction C uses KlenTaq 1 DNA polymerase having no 5'→3' exonuclease activity and 200 nM mediator probe (FIG. 2C); Reaction D uses KlenTaq 1 DNA polymerase having no 5'→3' exonuclease activity and 0 nM mediator probe (FIG. 2D); and, in FIGS. 2A-2D, the solid line represents the experimental result using 293T cell genomic DNA as a template; the dashed line represents the experimental result using water as a template (negative control).

FIGS. 3A-3D show the amplification curves of 4 real-time PCRs using the mediator probe BRAF-MP1 and the fluorescent probe UP-MB having a hairpin structure, wherein, Reaction A uses Taq DNA polymerase having 5'→3' exonuclease activity and 200 nM mediator probe (FIG. 3A); Reaction B uses Taq DNA polymerase having 5'→3' exonuclease activity and 0 nM mediator probe (FIG. 3B); Reaction C uses KlenTaq 1 DNA polymerase having no 5'→3' exonuclease activity and 200 nM mediator probe (FIG. 3C); Reaction D uses KlenTaq 1 DNA polymerase having no 5'→3' exonuclease activity and 0 nM mediator probe (FIG. 3D); and, in FIG. 3A-3D, the solid line represents the experimental result using 293T cell genomic DNA as a template; the dashed line represents the experimental result using water as a template (negative control).

FIGS. 4A-4B show the amplification curves and melting curves of 4 real-time PCRs using the mediator probe BRAF-MP1 and the fluorescent probe UP-L2 (FIG. 4A) or UP-MB (FIG. 4B), wherein, in the assay of FIG. 4A, the mediator probe BRAF-MP1, the fluorescent probe UP-L2 and polymerase Taq are used; in the assay of FIG. 4B, the mediator probe BRAF-MP1, the fluorescent probe UP-MB and polymerase Taq are used; and, in the assays of FIGS. 4A-4B, the solid line represents the experimental result using 293T cell genomic DNA as a template; the dashed line represents the experimental result using water as a template (negative control).

FIGS. 9A-9B show the amplification curves and melting curves of real-time PCRs in which the amplification is carried out by a two-step method (FIG. 9A) or a three-step method (FIG. 9B); wherein, in said real-time PCR, the mediator probe BRAF-MP2, the hairpin fluorescent probe UP-MB, polymerase Taq and a specified amount (100 ng, 10 ng, 1 ng, 100 pg or 10 pg) of 293T cell genomic DNA are used; and, the solid line in the figure represents the experimental result using 293T cell genomic DNA as a template; the dashed line represents the experimental result using water as a template (negative control).

FIG. 10 shows the amplification curves and melting curves of 3 real-time PCRs using a plasmid carrying wild-type KRAS gene or mutant KRAS gene or water as a template; wherein, in said real-time PCR, the mediator probe KRAS-MP2, the hairpin fluorescent probe UP-MB and polymerase Taq are used; and, and the black solid line represents the experimental result using a plasmid carrying wild-type KRAS gene as a template; the grey solid line represents the experimental result using a plasmid carrying mutant KRAS gene as a template; the dashed line represents the experimental result using water as a template (negative control).

FIG. 11 shows the amplification curves and melting curves of real-time PCRs using 2 mediator probes and 1 fluorescent probe; wherein, in said real-time PCR, 4 primers (BRAF-F, BRAF-R, KRAS-F and KRAS-R), 2 mediator probes (BRAF-MP2 and KRAS-MP3), the hairpin fluorescent probe UP-MB, polymerase Taq and a specified amount (100 ng, 10 ng, 1 ng, 100 pg or 10 pg) of 293T cell genomic DNA are used; and, the solid line in the figure represents the experimental result using 293T cell genomic DNA as a template; the dashed line represents the experimental result using water as a template (negative control).

FIG. 12 shows the melting curves of real-time PCRs using 4 mediator probes and 1 fluorescent probe; wherein, in said real-time PCR, 9 primers, 4 mediator probes, and 1 fluorescent probe as described in Table 4, polymerase TaqHS and a specified amount (100 ng, 10 ng, 1 ng, or 100 pg) of cellular genomic DNA obtained from a normal male are used; and, the solid line in the figure shows the experimental result using the genomic DNA as a template; the dashed line represents the experimental result using water as a template (negative control).

FIGS. 13A-13C show the melting curves of 83 real-time PCRs using 20 mediator probes and 6 fluorescent probes; wherein, in said real-time PCR, 41 primers, 20 mediator probes, and 6 fluorescent probes as described in Table 5, polymerase TaqHS and cellular genomic DNA obtained from normal males (83 samples in total) are used; FIG. 13A shows the melting curve obtained from ROX detection channel; FIG. 13B shows the melting curve obtained from FAM detection channel; FIG. 13C shows the melting curve obtained from Cy5 detection channel; and, the solid line in the figure shows the experimental result using the cellular genomic DNA (83 samples) as a template; the dashed line represents the experimental result using water as a template (negative control).

Figure 1A:
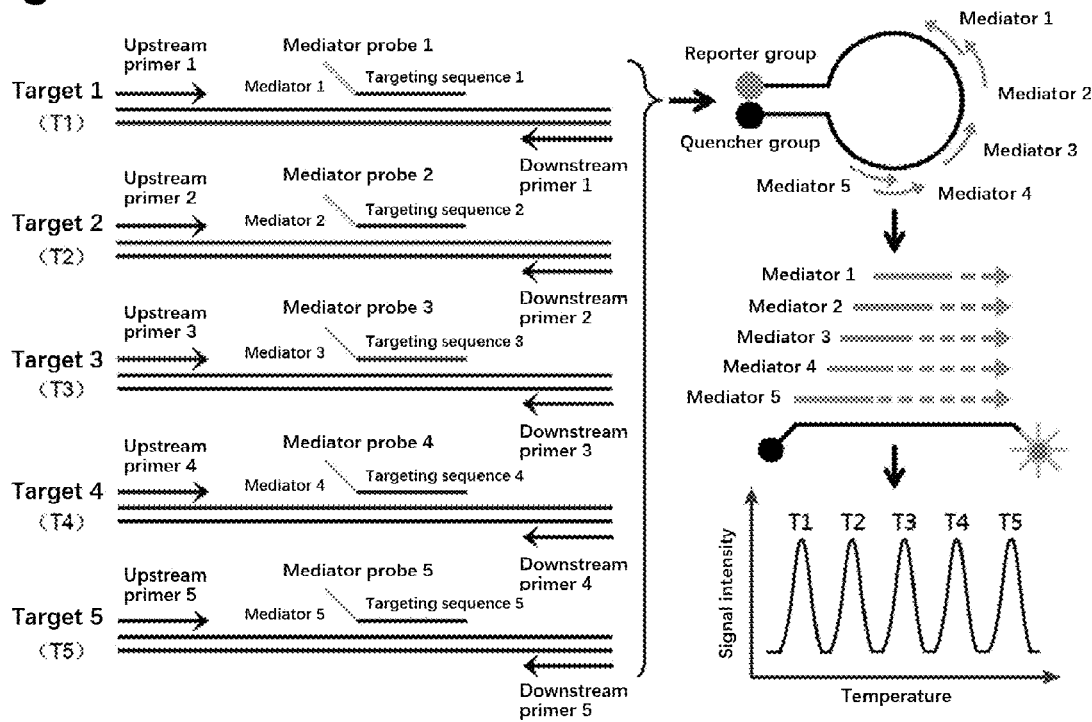
FIGS. 1A-1B illustrate exemplary embodiments for the method of the invention, to describe the basic principle of the method of the invention.
Figure 1B:
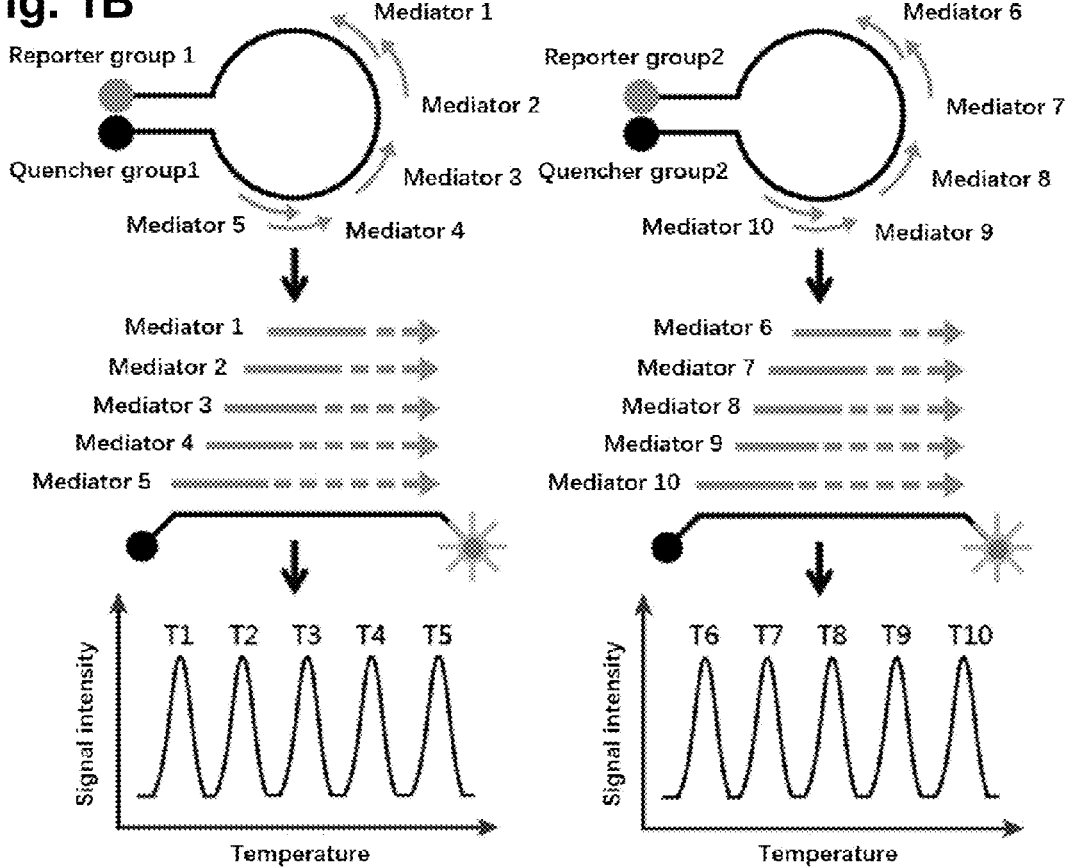

Specific Modes for Carrying Out the Invention

The invention is illustrated by reference to the following examples which are used only for the purpose of illustration (not intended to limit the protection scope of the invention). It should be understood that the examples are only used to illustrate the principle and technical effects of the invention, rather than showing all the possibility of the invention. The invention is not limited to the materials, reaction conditions or parameters mentioned in these examples. A person skilled in the art, based on the principle of the invention, can use other similar materials or reaction conditions to carry out other technical solutions. Such technical solutions do not depart from the basic principle and concept of the invention, and fall into the scope of the invention.

Example 1

Real-Time PCR Assay Using Mediator Probes and Fluorescent Probes

In the example, BRAF gene was used as an exemplary target sequence to be detected, to establish a real-time PCR assay using a mediator probe and a fluorescent probe, and to evaluate the effect of using a linear fluorescent probe and a hairpin fluorescent probe (i.e. a fluorescent probe having a hairpin structure) in said real-time PCR assay. The fluorescent probes (linear or hairpin) used were self-quenching fluorescent probes, one end of which was labeled with a fluorescent group (e.g. ROX), the other end of which was labeled with a quencher group (e.g. BHQ2).

In brief, a 25-μL PCR reaction system was used to carry out real-time PCR, said PCR reaction system comprised 1× buffer A (67 mM Tris-HCl, 16.6 mM $(NH_4)_2SO_4$, 6.7 μM EDTA and 0.085 mg/mL BSA), 3.0 mM $MgCl_2$, 0.2 mM dNTPs, 2.0 U polymerase Taq (Linglan Biotechnology Co., Ltd., Shanghai) or KlenTaq 1 (AB Bioscience, UK), 400 nM Upstream primer and 400 nM Downstream primer, 0 or 200 nM mediator probe, 200 nM fluorescent probe (linear or hairpin), 0.1 μL Single Strand DNA-Binding Protein (SSB), and 5 μL 293T cell genomic DNA. The reaction conditions of real-time PCR were: 95° C., 5 min; and then 50 cycles of (95° C., 20 s and 61° C., 1 min); and, collecting fluorescence at 61° C. The experimental apparatus used was Bio-Rad CFX96 real-time PCR instrument (Bio-Rad, USA). The primers and probes used were synthesized by Shanghai Sangon Co., Ltd. The sequences of primers and probes used were shown in Table 1.

TABLE 1

Sequences of primers and probes used

|  | Sequence (5' → 3') | SEQ ID NO |
|---|---|---|
| Upstream primer BRAF-F | TGTTTTCCTTTACTTA CTACACCTCAG | 1 |
| Downstream primer BRAF-R | TCAGTGGAAAAATAGC CTCAATTC | 2 |
| mediator probe BRAF-MP1 | AAATCGTTCTGGGCTC TACGCTACAGTGAAAT CTCGATGGAGTGGGTC C-$C_7NH_2$ | 3 |
| Fluorescent probe | | |
| UP-L2 (linear) | ROX-5'-TTGTCACCT GTCCTAGAGAGCGTAG AGCCCAGAACGATTT-BHQ2 | 4 |

TABLE 1-continued

Sequences of primers and probes used

|  | Sequence (5' → 3') | SEQ ID NO |
|---|---|---|
| UP-MB (hairpin) | ROX-5'-CCCGGCTTG TCACCTGTCCTAGAGA GCGTAGAGCCCAGAAC GATTTGCCGGG-BHQ2 | 5 |

Note:
-$C_7NH_2$ was used to block 3'-OH of a mediator probe (the same below).

The experimental results were shown in FIGS. 2A-3D. FIGS. 2A-2D show the amplification curves of 4 real-time PCRs using the mediator probe BRAF-MP1 and the liner fluorescent probe UP-L2, wherein, Reaction A uses Taq DNA polymerase having 5'→3' exonuclease activity and 200 nM mediator probe (FIG. 2A); Reaction B uses Taq DNA polymerase having 5'→3' exonuclease activity and 0 nM mediator probe (FIG. 2B); Reaction C uses KlenTaq 1 DNA polymerase having no 5'→3' exonuclease activity and 200 nM mediator probe (FIG. 2C); Reaction D uses KlenTaq 1 DNA polymerase having no 5'→3' exonuclease activity and 0 nM mediator probe (FIG. 2D); and, in FIGS. 2A-2D, the solid line represents the experimental result using 293T cell genomic DNA as a template; the dashed line represents the experimental result using water as a template (negative control).

The result of FIGS. 2A-2D show that real-time PCR fluorescent signal was generated only in Reaction A, and no fluorescent signal was generated in Reaction B, C or D. These results show that when a polymerase having 5'→3' exonuclease activity (e.g. Taq polymerase) was used, mediator probes and linear fluorescent probes could be used in real-time PCR.

FIGS. 3A-3D show the amplification curves of 4 real-time PCRs using the mediator probe BRAF-MP1 and the fluorescent probe UP-MB having a hairpin structure, wherein, Reaction A uses Taq DNA polymerase having 5'→3' exonuclease activity and 200 nM mediator probe (FIG. 3A); Reaction B uses Taq DNA polymerase having 5'→3' exonuclease activity and 0 nM mediator probe (FIG. 3B); Reaction C uses KlenTaq 1 DNA polymerase having no 5'→3' exonuclease activity and 200 nM mediator probe (FIG. 3C); Reaction D uses KlenTaq 1 DNA polymerase having no 5'→3' exonuclease activity and 0 nM mediator probe (FIG. 3D); and, in FIGS. 3A-3D, the solid line represents the experimental result using 293T cell genomic DNA as a template; the dashed line represents the experimental result using water as a template (negative control).

The result of FIGS. 3A-3D show that real-time PCR fluorescent signal was generated only in Reaction A, and no fluorescent signal was generated in Reaction B, C or D. These results show that when a polymerase having 5'→3' exonuclease activity (e.g. Taq polymerase) was used, mediator probes and fluorescent probes having a hairpin structure could be used in real-time PCR.

Example 2

Post-PCR MCA Assay Using Mediator Probes and Fluorescent Probes

In the example, BRAF gene was used as an exemplary target sequence to be detected, to evaluate the effect of using a linear fluorescent probe and a hairpin fluorescent probe in post-PCR MCA method.

As described in Example 1, a 25-μL PCR reaction system was used to carry out real-time PCR. The PCR reaction system used was the same as the one used in Example 1. The PCR reaction conditions used were: 95° C., 5 min; 50 cycles (95° C., 20 s and 61° C., 1 min); and 35° C., 10 min; and, collecting fluorescence at 61° C. After PCR was finished, melting curve analysis was carried out according to the following procedures: 95° C., 2 min; 45° C., 2 min; and then increasing the temperature of the reaction system from 45° C. to 95° C. at a heating rate of 0.5° C./step (the duration for each step was 5 s), during which fluorescent signal was collected. The experimental results were shown in FIGS. 4A-4B.

FIGS. 4A-4B show the amplification curves and melting curves of 4 real-time PCRs using the mediator probe BRAF-MP1 and the fluorescent probe UP-L2 (FIG. 4A) or UP-MB (FIG. 4B), wherein, in the assay of FIG. 4A, the mediator probe BRAF-MP1, the fluorescent probe UP-L2 and polymerase Taq are used; in the assay of FIG. 4B, the mediator probe BRAF-MP1, the fluorescent probe UP-MB and polymerase Taq are used; and, in the assays of FIGS. 4A-4B, the solid line represents the experimental result using 293T cell genomic DNA as a template; the dashed line represents the experimental result using water as a template (negative control).

The result of FIGS. 4A-4B show that when a reaction system comprising a mediator probe and a fluorescent probe (linear or hairpin) was used to carry out real-time PCR and the subsequent MCA, the target peaks could be detected at about 78° C. in the experimental groups. These results show that a mediator probe and a fluorescent probe (linear or hairpin) could be used to carry out post-PCR MCA assay. In addition, the result of FIGS. 4A-4B also show that when a linear fluorescent probe was used to carry out MCA assay, a non-specific peak could be detected at about 60° C. (which represents the duplex formed by the mediator probe and the linear fluorescent probe). By contrast, when a hairpin fluorescent probe was used to carry out MCA assay, the non-specific peak was significantly weakened. These results show that a hairpin fluorescent probe had better specificity than a linear fluorescent probe. Therefore, under some situations, a hairpin fluorescent probe may be preferred.

Example 3

Selection of the Length of Mediator Sequences

In the example, multiple mediator probes having mediator sequences of different lengths were designed and synthesized, and the method described in Example 2 was used to evaluate the effect of the length of a mediator sequence on post-PCR MCA assay.

In brief, 3 mediator probes were designed and synthesized, and the lengths of the mediator sequences comprised therein were 19, 15 and 13 bases, respectively. The particular sequences of the 3 mediator probes were shown in Table 2.

TABLE 2

Sequences of mediator probes

| mediator probe | Sequence (5' → 3') | SEQ ID NO: |
|---|---|---|
| BRAF-MP1 | AAATCGTTCTGGGCTCTACGC TACAGTGAAATCTCGATGGAG TGGGTCC-C$_7$NH$_2$ | 3 |

TABLE 2-continued

Sequences of mediator probes

| mediator probe | Sequence (5' → 3') | SEQ ID NO: |
|---|---|---|
| BRAF-MP2 | AAATCGTTCTGGGCTCTACAG TGAAATCTCGATGGAGTGGGT CC-C$_7$NH$_2$ | 6 |
| BRAF-MP3 | AAATCGTTCTGGGCAGTGAAA TCTCGATGGAGTGGGTCC- C$_7$NH$_2$ | 7 |

As described in Example 2, a 25-μL PCR reaction system was used to carry out real-time PCR and the subsequent MCA assay. Except for the mediator probes used, the PCR reaction system, the PCR reaction conditions and the MCA assay conditions as used were the same as those used in Example 2. The experimental results were shown in FIGS. 5-6.

Figure 5A:
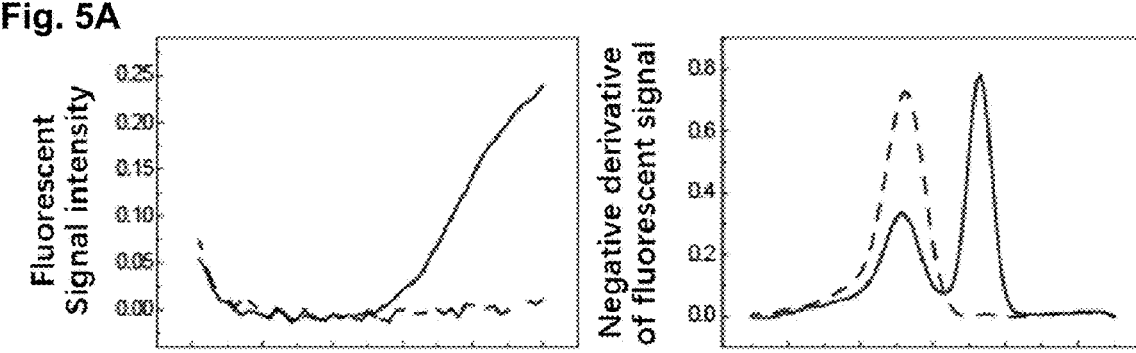
FIGS. 5A-5C show the amplification curves and melting curves of 3 real-time PCRs using the mediator probe (BRAF-MP1, BRAF-MP2, or BRAF-MP3) and the linear fluorescent probe UP-L2; wherein, in the assay of FIG. 5A, the mediator probe BRAF-MP1, the fluorescent probe UP-L2 and polymerase Taq are used; in the assay of FIG. 5B, the mediator probe BRAF-MP2, the fluorescent probe UP-L2 and polymerase Taq are used; in the assay of FIG. 5C, the mediator probe BRAF-MP3, the fluorescent probe UP-L2 and polymerase Taq are used; and, in the assays of FIGS. 5A-5C, the solid line represents the experimental result using 293T cell genomic DNA as a template; the dashed line represents the experimental result using water as a template (negative control).
Figure 5B:
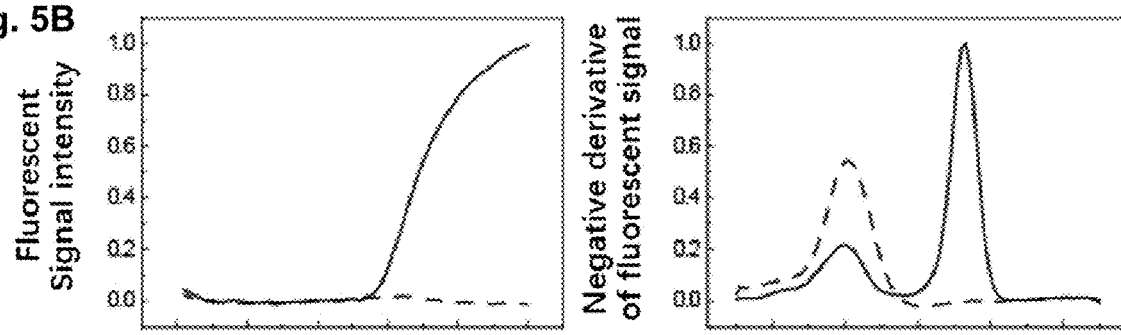
Figure 5C:
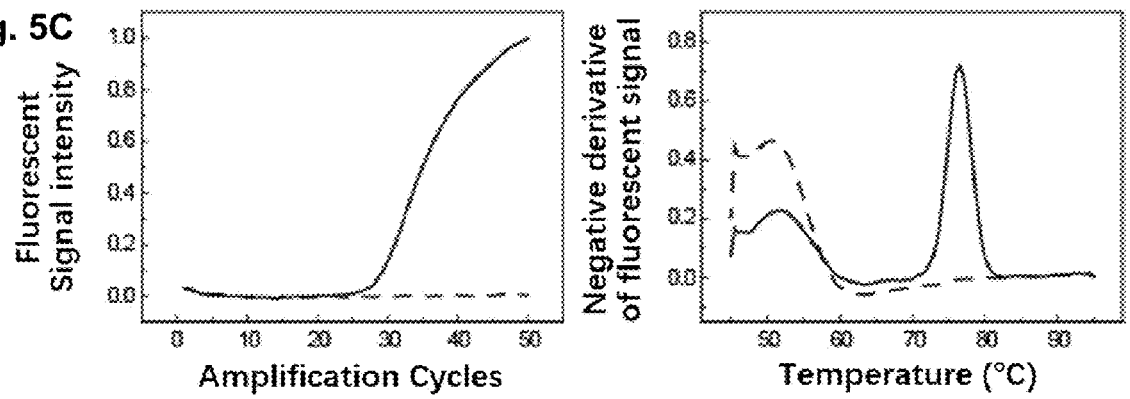

FIGS. 5A-5C show the amplification curves and melting curves of 3 real-time PCRs using the mediator probe (BRAF-MP1, BRAF-MP2, or BRAF-MP3) and the linear fluorescent probe UP-L2; wherein, in the assay of FIG. 5A, the mediator probe BRAF-MP1, the fluorescent probe UP-L2 and polymerase Taq are used; in the assay of FIG. 5B, the mediator probe BRAF-MP2, the fluorescent probe UP-L2 and polymerase Taq are used; in the assay of FIG. 5C, the mediator probe BRAF-MP3, the fluorescent probe UP-L2 and polymerase Taq are used; and, in the assays of FIGS. 5A-5C, the solid line represents the experimental result using 293T cell genomic DNA as a template; the dashed line represents the experimental result using water as a template (negative control).

Figure 6A:
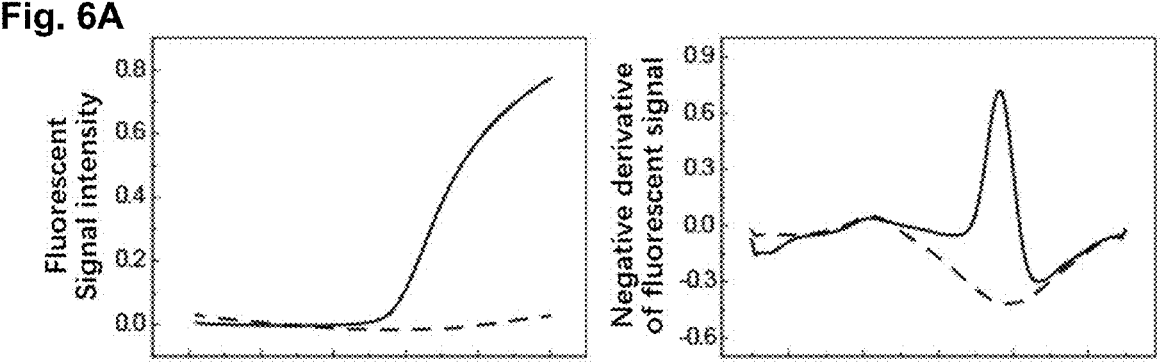
FIGS. 6A-6C show the amplification curves and melting curves of 3 real-time PCRs using the mediator probe (BRAF-MP1, BRAF-MP2, or BRAF-MP3) and the hairpin fluorescent probe UP-MB; wherein, in the assay of FIG. 6A, the mediator probe BRAF-MP1, the fluorescent probe UP-MB and polymerase Taq; in the assay FIG. 6B, the mediator probe BRAF-MP2, the fluorescent probe UP-MB and polymerase Taq are used; in the assay of FIG. 6C, the mediator probe BRAF-MP3, the fluorescent probe UP-MB and polymerase Taq are used; and, in the assays of FIGS. 6A-6C, the solid line represents the experimental result using 293T cell genomic DNA as a template; the dashed line represents the experimental result using water as a template (negative control).
Figure 6B:
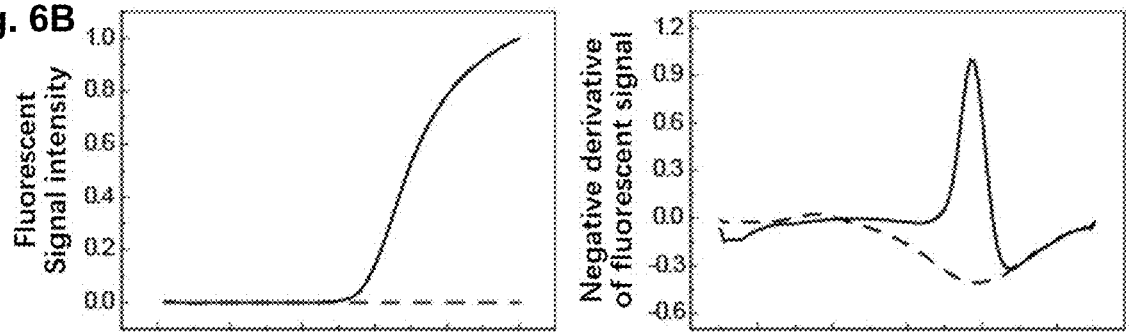
Figure 6C:
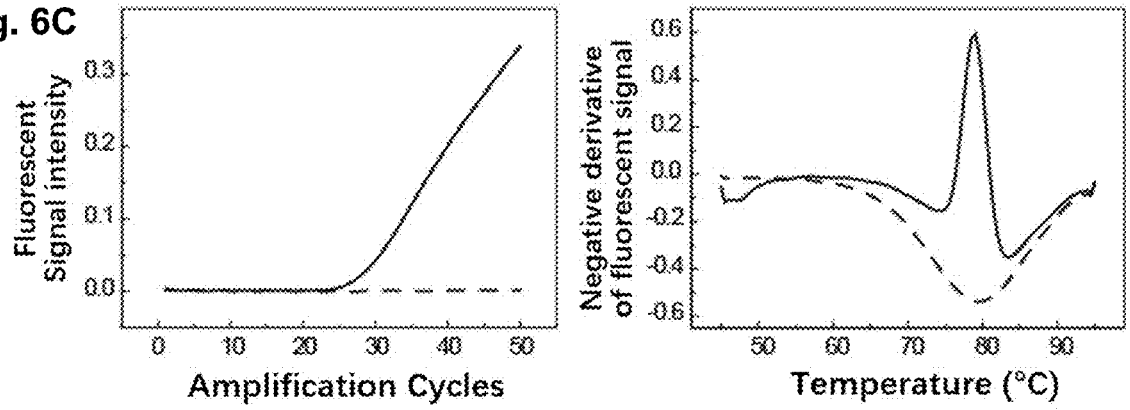

FIGS. 6A-6C show the amplification curves and melting curves of 3 real-time PCRs using the mediator probe (BRAF-MP1, BRAF-MP2, or BRAF-MP3) and the hairpin fluorescent probe UP-MB; wherein, in the assay of FIG. 6A, the mediator probe BRAF-MP1, the fluorescent probe UP-MB and polymerase Taq; in the assay FIG. 6B, the mediator probe BRAF-MP2, the fluorescent probe UP-MB and polymerase Taq are used; in the assay of FIG. 6C, the mediator probe BRAF-MP3, the fluorescent probe UP-MB and polymerase Taq are used; and, in the assays of FIGS. 6A-6C, the solid line represents the experimental result using 293T cell genomic DNA as a template; the dashed line represents the experimental result using water as a template (negative control).

The results in FIGS. 5A-6C show that three mediator probes having mediator sequences of different lengths together with fluorescent probes (linear or hairpin), could be used to carry out post-PCR MCA assay. Therefore, these results show that according to practical need, a mediator probe of a suitable length could be selected to carry out post-PCR MCA assay. In addition, the results of FIGS. 5-6 also show that with the decrease in the mediator length of mediator probes, the $T_m$ value of the nonspecific peak decreased gradually, and the signal intensity reduced continuously. Therefore, according to practical need, the mediator length of a mediator probe can be properly optimized, so as to reduce the interference of nonspecific peaks.

In addition, the results of FIGS. 5A-6C also show that when a linear fluorescent probe was used to carry out MCA assay, a nonspecific peak (which represented a duplex formed by the mediator probe and the linear fluorescent probe) could be detected. By contrast, when a hairpin fluorescent probe was used to carry out MCA assay, the signal of the non-specific peak was significantly decreased or even undetected. These results show that a hairpin fluorescent probe had better specificity than a linear fluorescent probe, could better overcome the interference of a nonspecific peak resulted from hybridization between a mediator probe and a fluorescent probe. Therefore, under some situations, a hairpin fluorescent probe may be preferred.

Example 4

Sensitivity of Mediator Probe and Hairpin Fluorescent Probe-Based Post-PCR MCA Assay In the example, sensitivity of mediator probe and hairpin fluorescent probe-based post-PCR MCA assay was studied. In brief, as described in Example 2, a 25-μL PCR reaction system was used to carry out real-time PCR and the subsequent MCA assay, wherein, the mediator probe used was BRAF-MP2, the fluorescent probe used was UP-MB, the polymerase used was Taq, and the template used was 293T cell genomic DNA (the amount of which was 100 ng, 10 ng, 1 ng, 100 pg or 10 pg; the assay was repeated for three times for each amount). Except for the amount of genomic DNA, the PCR reaction system, the PCR reaction conditions and the MCA assay conditions used were the same as those used in Example 2. The result was shown in FIG. 7.

Figure 7:
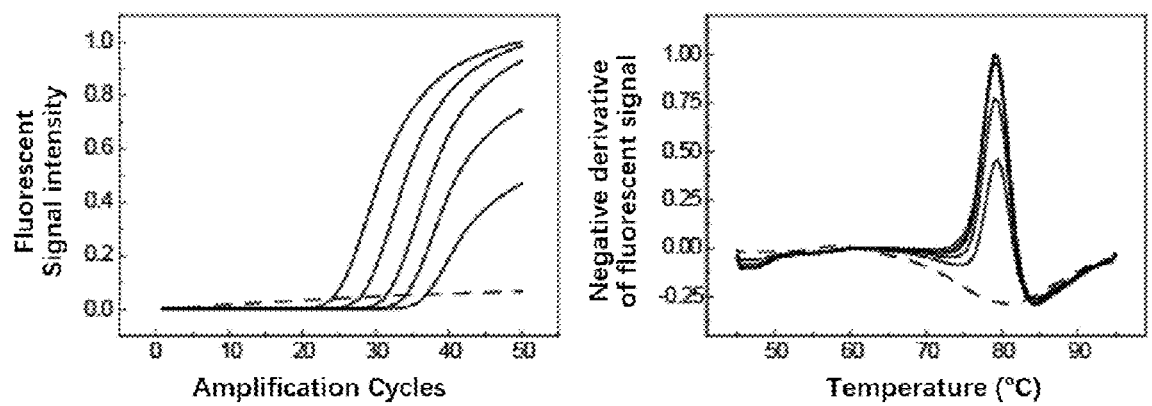
FIG. 7 shows the amplification curves and melting curves of 5 real-time PCRs using a specific amount (100 ng, 10 ng, 1 ng, 100 pg or 10 pg) of 293T cell genomic DNA as a template; wherein, in said real-time PCR, the mediator probe BRAF-MP2, the hairpin fluorescent probe UP-MB and polymerase Taq are used; and, the solid line in the figure represents the experimental result using 293T cell genomic DNA as a template; the dashed line represents the experimental result using water as a template (negative control).

FIG. 7 shows the amplification curves and melting curves of 5 real-time PCRs using a specific amount (100 ng, 10 ng, 1 ng, 100 pg or 10 pg) of 293T cell genomic DNA as a template; wherein, in said real-time PCR, the mediator probe BRAF-MP2, the hairpin fluorescent probe UP-MB and polymerase Taq are used; and, the solid line in the figure represents the experimental result using 293T cell genomic DNA as a template; the dashed line represents the experimental result using water as a template (negative control).

The result of FIG. 7 shows that when genomic DNA at an amount as low as 10 pg was used as a template, a specific target peak could still be detected by the mediator probe and hairpin fluorescent probe-based post-PCR MCA assay. This shows that said post-PCR MCA assay had a very high sensitivity and could even be used to detect a single human genome.

Example 5

Selection of PCR Amplification Conditions

In the example, PCR amplification conditions were evaluated for their effect on mediator probe and hairpin fluorescent probe-based post-PCR MCA assay.

(1) Symmetric Amplification and Asymmetric Amplification

In brief, as described in Example 4, a 25-μL PCR reaction system was used to carry out real-time PCR and the subsequent MCA assay, wherein, the mediator probe used was BRAF-MP2, the fluorescent probe used was UP-MB, the polymerase used was Taq, and the template used was a specified amount (100 ng, 10 ng, 1 ng or 100 pg) of 293T cell genomic DNA. Except for the concentrations of primers, the PCR reaction system, the PCR reaction conditions and the MCA assay conditions used were the same as those used in Example 4. In symmetric PCR, the primers used were 400 nM upstream primer and 400 nM downstream primer. In asymmetric PCR, the primers used were 800 nM upstream primer (the primer and a probe were in reverse directions, i.e. an extension product thereof bound to the probe) and 80 nM downstream primer. The experimental results were shown in FIG. 8.

Figure 8A:
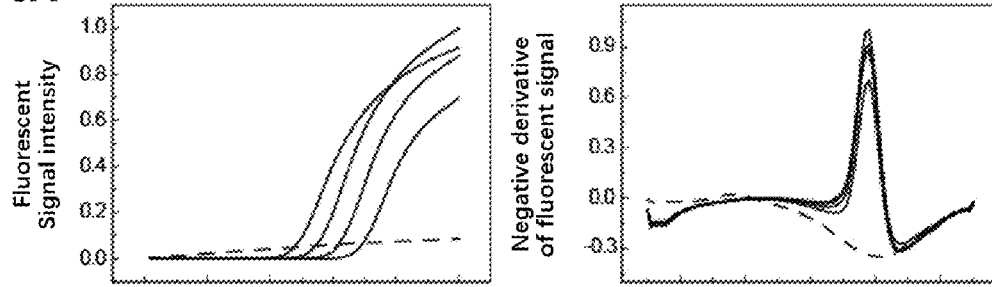
FIGS. 8A-8B show the amplification curves and melting curves of real-time PCRs in which the amplification is carried out in a symmetric manner (FIG. 8A) or in an asymmetric manner (FIG. 8B); wherein, in said real-time PCR, the mediator probe BRAF-MP2, the hairpin fluorescent probe UP-MB, polymerase Taq and a specified amount (100 ng, 10 ng, 1 ng or 100 pg) of 293T cell genomic DNA are used; and, the solid line in the figure represents the experimental result using 293T cell genomic DNA as a template; the dashed line represents the experimental result using water as a template (negative control).
Figure 8B:
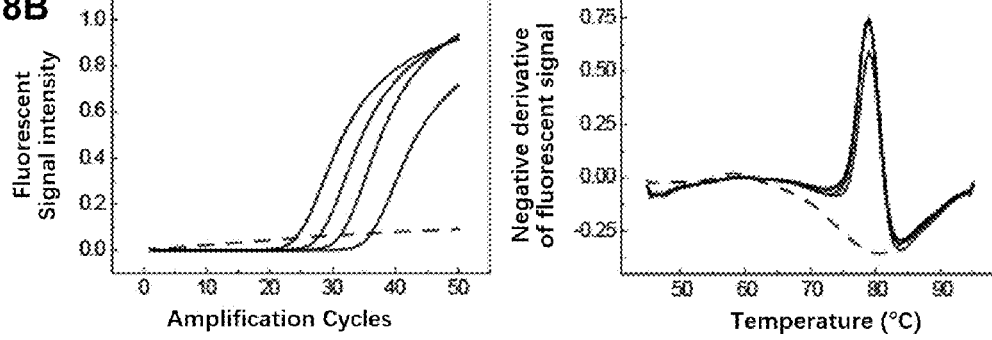

FIGS. 8A-8B show the amplification curves and melting curves of real-time PCRs in which the amplification is carried out in a symmetric manner (FIG. 8A) or in an asymmetric manner (FIG. 8B); wherein, in said real-time PCR, the mediator probe BRAF-MP2, the hairpin fluorescent probe UP-MB, polymerase Taq and a specified amount (100 ng, 10 ng, 1 ng or 100 pg) of 293T cell genomic DNA are used; and, the solid line in the figure represents the experimental result using 293T cell genomic DNA as a template; the dashed line represents the experimental result using water as a template (negative control).

The result of FIGS. 8A-8B show that under conditions of symmetric amplification or asymmetric amplification, the mediator probe and hairpin fluorescent probe-based post-PCR MCA assay could detect the specific target peak; and under the two conditions, there were no significant difference in Cq value of PCR and specific peaks generated in MCA assay. Therefore, in said post-PCR MCA assay, PCR amplification could be carried out in a symmetric or an asymmetric manner.

(2) Two-Step PCR and Three-Step PCR

In brief, as described in Example 4, a 25-μL PCR reaction system was used to carry out real-time PCR and the subsequent MCA assay, wherein, the mediator probe used was BRAF-MP2, the fluorescent probe used was UP-MB, the polymerase used was Taq, and the template used was a specified amount (100 ng, 10 ng, 1 ng, 100 pg or 10 pg) of 293T cell genomic DNA. Except for PCR reaction conditions, the PCR reaction system and the MCA assay conditions used were the same as those used in Example 4. The amplification conditions used in two-step PCR were: 95° C., 5 min; and then 50 cycles of (95° C., 20 s and 61° C., 1 min). The amplification conditions used in three-step PCR were: 95° C., 5 min; and then 50 cycles of (95° C., 20 s; 61° C., 40 s; and 72° C., 20 s). The experimental results were shown in FIG. 9.

FIGS. 9A-9B show the amplification curves and melting curves of real-time PCRs in which the amplification is carried out by a two-step method (FIG. 9A) or a three-step method (FIG. 9B); wherein, in said real-time PCR, the mediator probe BRAF-MP2, the hairpin fluorescent probe UP-MB, polymerase Taq and a specified amount (100 ng, 10 ng, 1 ng, 100 pg or 10 pg) of 293T cell genomic DNA are used; and, the solid line in the figure represents the experimental result using 293T cell genomic DNA as a template; the dashed line represents the experimental result using water as a template (negative control).

The result of FIGS. 9A-9B show that under the conditions of two-step PCR or three-step PCR, the mediator probe and hairpin fluorescent probe-based post-PCR MCA assay could detect the specific target peak. In addition, the result of FIGS. 9A-9B also show that under the conditions of two-step PCR, said post-PCR MCA assay could be used to detect genomic DNA at a concentration as low as 10 pg; under the conditions of three-step PCR, said post-PCR MCA assay could be used to detect genomic DNA at a concentration as low as 100 pg. These results show that in said post-PCR MCA assay, PCR amplification could be carried out in a two-step manner or a three-step manner; and, when a two-step method was used to carry out PCR amplification, said post-PCR MCA assay have a higher sensitivity.

Example 6

Effect of Target Sequence Variation on the Mediator Probe and Hairpin Fluorescent Probe-Based Post-PCR MCA Assay One characteristic of the mediator probe and hairpin fluorescent probe-based post-PCR MCA assay, is that the detected melting point depends on the mediator sequence and fluorescent probe, and is not associated with the target sequence. Therefore, even if there was variation in the target sequence to be detected (as a result, the target sequence did not completely match with the target specific sequence in the mediator probe (e.g. there was one or more mismatched bases)), said post-PCR MCA assay could detect the specific peak, and the melting point of the specific peak retained unchanged, as long as the mediator probe could bind to the target sequence during real-time PCR annealing/extension. In order to verify this characteristic, in the example, target sequence variation/mutation was evaluated for its effect on the mediator probe and hairpin fluorescent probe-based post-PCR MCA assay.

In brief, a 25-μL PCR reaction system was used to carry out real-time PCR, said PCR reaction system comprised 1× buffer A (67 mM Tris-HCl, 16.6 mM $(NH_4)_2SO_4$, 6.7 μM EDTA and 0.085 mg/mL BSA), 3.0 mM $MgCl_2$, 0.2 mM dNTPs, 2.0 U polymerase Taq, 400 nM Upstream primer and 400 nM Downstream primer, 200 nM Mediator probe KRAS-MP2, 200 nM fluorescent probe UP-MB, 0.1 μL single strand DNA-binding protein (SSB), and 5 pL plasmid carrying wild-type KRAS gene or mutant KRAS gene (as a template). Sequences of the primers and probes used were shown in Table 3.

TABLE 3

Sequences of the primers and probes used

| | Sequence (5' → 3') | SEQ ID NO: |
|---|---|---|
| Upstream primer KRAS-F | ATTATAAGGCCTGCTGAAAATGAC | 8 |
| Downstream primer KRAS-R | GCACCAGTAATATGCATATTAAAAC | 9 |
| Mediator probe KRAS-MP2 | AAATCGTTCTGGGCTCTACGTGGTA GTTGGAGCTGGTGGCGT-$C_7NH_2$ | 10 |
| Fluorescent probe UP-MB | ROX-5'-CCCGGCTTGTCACCTGTC CTAGAGAGCGTAGAGCCCAGAACGA TTTGCCGGG-BHQ2 | 5 |

As compared with wild-type KRAS gene, mutant KRAS gene had a G→A base mutation in Exon 2, and was used to simulate target sequence variation. The target specific sequence in the mediator probe used completely matched with the sequence of the wild-type KRAS gene, but had one mismatch with the mutant KRAS gene.

The reaction conditions of real-time PCR were: 95° C., 5 min; 50 cycles of (95° C., 20 s and 61° C., 1 min); and 35° C., 10 min; and, collecting fluorescence at 61° C. After PCR was finished, melting curve analysis was carried out according to the following procedures: 95° C., 2 min; 45° C., 2 min; and then increasing the temperature of the reaction system from 45° C. to 95° C. at a heating rate of 0.5° C./step (the duration was 5 s for each step), during which ROX fluorescent signal was collected. The experimental apparatus used was Bio-Rad CFX96 real-time PCR instrument (Bio-Rad, USA). The experimental results were shown in FIG. 10.

FIG. 10 shows the amplification curves and melting curves of 3 real-time PCRs using a plasmid carrying wild-type KRAS gene or mutant KRAS gene or water as a template; wherein, in said real-time PCR, the mediator probe KRAS-MP2, the hairpin fluorescent probe UP-MB and polymerase Taq are used; and, and the black solid line represents the experimental result using a plasmid carrying the wild-type KRAS gene as a template; the grey solid line represents the experimental result using a plasmid carrying the mutant KRAS gene as a template; the dashed line represents the experimental result using water as a template (negative control).

The result of FIG. 10 shows that when the plasmid carrying the wild-type or mutant KRAS gene was used as a template, the mediator probe and hairpin fluorescent probe-based post-PCR MCA assay could detect a specific target peak, and under said two conditions, the detected specific target peaks had the same melting point. These experimental results show that the mediator probe and hairpin fluorescent probe-based post-PCR MCA assay could tolerate certain target sequence variation/mutation; and, as long as the target sequence variation or mutation did not affect the binding of the mediator probe to the varied or mutated target sequence during real-time PCR annealing/extension, said post-PCR MCA assay could still be used to detect the varied/mutated target sequence, and the melting point of the detected specific peak retained unchanged.

Example 7. Duplex detection In the example, two mediator probes and one fluorescent probe were used in a single post-PCR MCA assay to achieve simultaneous detection and discrimination (i.e. duplex detection) of 2 target sequences. In the experiment, BRAF gene and KRAS gene were used as exemplary target sequences to be detected, and a specified amount of 293T cell genomic DNA was used as a sample to be detected.

In brief, a 25-μL PCR reaction system was used to carry out real-time PCR, said PCR reaction system comprised 1× buffer A (67 mM Tris-HCl, 16.6 mM $(NH_4)_2SO_4$, 6.7 μM EDTA and 0.085 mg/mL BSA), 3.0 mM $MgCl_2$, 0.2 mM dNTPs, 2.0 U polymerase Taq, 400 nM primers BRAF-F (SEQ ID NO: 1), BRAF-R (SEQ ID NO: 2), KRAS-F (SEQ ID NO: 8) and KRAS-R (SEQ ID NO: 9), 100 nM mediator probe BRAF-MP2 (SEQ ID NO: 6, comprising a target specific sequence specific for BRAF gene), 200 nM mediator probe KRAS-MP3 (5'-CTC TCT AGG ACA GGT GGT GGC GTA GGC AAG AGT GC-C7$NH_2$-3' (SEQ ID NO: 11); comprising a target specific sequence specific for KRAS gene), 200 nM fluorescent probe UP-MB (SEQ ID NO: 5), 0.1 μL single strand DNA-binding protein (SSB), and a specified amount of 293T cell genomic DNA (100 ng, 10 ng, 1 ng, 100 pg or 10 pg; the assay was repeated for three times for each amount). The PCR reaction conditions and MCA assay conditions used were the same as those used in Example 6. The result was shown in FIG. 11.

FIG. 11 shows the amplification curves and melting curves of real-time PCRs using 2 mediator probes and 1 fluorescent probe; wherein, in said real-time PCR, 4 primers (BRAF-F, BRAF-R, KRAS-F and KRAS-R), 2 mediator probes (BRAF-MP2 and KRAS-MP3), the hairpin fluorescent probe UP-MB, polymerase Taq and a specified amount (100 ng, 10 ng, 1 ng, 100 pg or 10 pg) of 293T cell genomic DNA are used; and, the solid line in the figure represents the experimental result using 293T cell genomic DNA as a template; the dashed line represents the experimental result using water as a template (negative control).

The result of FIG. 11 shows that in the melting curve, two distinguishable specific peaks (marked as peak of BRAF and marked as peak of KRAS) appeared, the melting points of which corresponded to the duplexes formed by the fluorescent probe UP-MB and the extension products of the mediator sequences in the mediator probes BRAF-MP2 and KRAS-MP3, respectively. This result shows that by using two mediator probes and a fluorescent probe, simultaneous detection and discrimination (i.e. duplex detection) of two target sequences can be achieved in a single post-PCR MCA assay. In addition, the result of FIG. 11 also shows that the sensitivity of said duplex PCR MCA assay was very high (the detection limit could be as low as 10 pg genomic DNA), and could even be used in detection of a single human genome.

Example 8

Quadruplex Detection

In the example, by using four mediator probes and a fluorescent probe, simultaneous detection and discrimination (i.e. quadruplex detection) of 4 target sequences was achieved in a single post-PCR MCA assay. In this experiment, three detection sites (sY82, sY86 and sY242) on Y chromosome and an internal reference gene (ZFX/Y gene) were used as exemplary target sequences to be detected, and a specified amount of cellular genomic DNA obtained from a normal male was used as a sample to be detected.

In brief, a 25-µL PCR reaction system was used to carry out real-time PCR, said PCR reaction system comprised 1× buffer A (67 mM Tris-HCl, 16.6 mM $(NH_4)_2SO_4$, 6.7 µM EDTA and 0.085 mg/mL BSA), 11.0 mM $MgCl_2$, 0.7 mM dNTPs, 5.0 U polymerase TaqHS (TaKaRa, Dalian), the primers (8 primers and 1 common amplification primer) and the probes (4 mediator probes and 1 fluorescent probe) as shown in Table 4, and a specified amount of cellular genomic DNA obtained from a normal male (100 ng, 10 ng, 1 ng, or 100 pg; the assay was repeated for three times for each amount).

The PCR reaction conditions used were as followed: 95° C., 5 min; 4 cycles of (95° C., 20 s and 61° C., 1 min); 46 cycles of (95° C., 20 s and 62° C., 1 min); and 35° C., 30 min. After PCR was finished, melting curve analysis was carried out according to the following procedures: 95° C., 2 min; 40° C., 2 min; and then increasing the temperature of the reaction system from 40° C. to 95° C. at a heating rate of 0.4° C./step (the duration was 5 s for each step), during which ROX fluorescent signal was collected. The experimental apparatus used was Bio-Rad CFX96 real-time PCR instrument (Bio-Rad, USA). The result was shown in FIG. 12.

FIG. 12 shows the melting curves of real-time PCRs using 4 mediator probes and 1 fluorescent probe; wherein, in said real-time PCR, 9 primers, 4 mediator probes and 1 fluorescent probe as described in Table 4, polymerase TaqHS and a specified amount (100 ng, 10 ng, 1 ng, or 100 pg) of cellular genomic DNA obtained from a normal male were used; and, the solid line in the figure shows the experimental result using genomic DNA as a template; the dashed line represents the experimental result using water as a template (negative control).

The result of FIG. 12 shows that in the melting curve, four distinguishable specific peaks (marked as 4 peaks, i.e. 242, ZF, 82 and 86, respectively) appeared, the melting points of which corresponded to the duplexes formed by said fluorescent probes and the extension products of the mediator sequences in the mediator probes 242-MP, ZF-MP, 82-MP and 86-MP. This result shows that by using four mediator probes and a fluorescent probe, simultaneous detection and discrimination (i.e. quadruplex detection) of 4 target sequences could be achieved in a single post-PCR MCA assay. In addition, the result of FIG. 12 also shows that the sensitivity of said quadruplex PCR MCA assay was high (the detection limit could be as low as 100 pg genomic DNA).

Example 9

20-Plex Detection

In the example, by using 20 mediator probes and 6 fluorescent probes, simultaneous detection and discrimination (i.e. 20-plex detection) of 20 target sequences was achieved in a single post-PCR MCA assay. In this experiment, 18 detection sites (sY242, sY82, sY86, sY152, sY145, sY84, sY124, sY127, sY128, sY133, sY143, sY134, sY155, sY154, sY157, sY254, sY239 and sY255) on Y chromosome and two internal reference genes (SRY gene and ZFX/Y gene) were used as exemplary target sequences to be detected, and cellular genomic DNA obtained from 83 normal males were used as samples to be detected.

In brief, a 25-µL PCR reaction system was used to carry out real-time PCR, said PCR reaction system comprised lxbuffer A (67 mM Tris-HCl, 16.6 mM $(NH_4)_2SO_4$, 6.7 µM EDTA and 0.085 mg/mL BSA), 11.0 mM $MgCl_2$, 0.7 mM dNTPs, 5.0 U polymerase TaqHS (TaKaRa, Dalian), the primers (40 primers and 1 common amplification primer) and probes (20 mediator probes and 6 fluorescent probes) as shown in Table 5, and 5 µL cell genomic DNA.

In said 6 fluorescent probes, fluorescent probes UP1 and UP2 were labeled with ROX and BHQ2, and their fluorescent signal was detected by ROX channel; fluorescent probes UP3 and UP4 were labeled with FAM and BHQ1, and their fluorescent signal was detected by FAM channel; fluorescent probes UP5 and UP6 were labeled with Cy5 and BHQ2, and their fluorescent signal was detected by Cy5 channel. The mediator sequences in Mediator probes 82-MP, 86-MP, 242-MP, ZF-MP could bind to fluorescent probe UP1, and were used to detect the target sequences sY82, sY86, sY242, and ZFX/Y, respectively. The mediator sequences in Mediator probes 152-MP, 145-MP, 84-MP, and SRY-MP could bind to fluorescent probe UP2, and were used to detect the target sequences sY152, sY145, sY84, SRY, respectively. The mediator sequences in mediator probes 124-MP, 127-MP, 128-MP could bind to fluorescent probe UP3, and were used to detect the target sequences sY124, sY127, and sY128, respectively. The mediator sequences in Mediator probes 133-MP, 143-MP, and 134-MP could bind to fluorescent probe UP4, and were used to detect the target sequences sY133, sY143 and sY134. The mediator sequences in Mediator probes 155-MP, 154-MP, and 157-MP could bind to fluorescent probe UP5, and were used to detect the target sequences sY155, sY154, and sY157. The mediator sequences in Mediator probes 254-MP, 239-MP, and 255-MP could bind to fluorescent probe UP6, and were used to detect the target sequences sY254, sY239 and sY255.

In this experiment, cellular genomic DNA from 83 normal males were used as samples to be tested (83 samples in total), and 83 real-time PCRs were carried out. The PCR reaction conditions used were as followed: 95° C., 5 min; 4 cycles of (95° C., 20 s and 61° C., 1 min); 46 cycles of (95° C., 20 s and 62° C., 1 min); and 35° C., 30 min. After PCR was finished, melting curve analysis was carried out according to the following procedures: increasing the temperature of the reaction system from 45° C. to 98° C. at a heating rate of 0.1° C./step (the duration was 5 s for each step); and then keeping it at 45° C. for 2 min; later, increasing the temperature of the reaction system from 45° C. to 98° C. at a heating rate of 0.04° C./step (the duration was 5 s for each step). During the whole process of MCA assay, the fluorescent signal from 3 detection channels (ROX, FAM and Cy5) was collected. The experimental apparatus used was Bio-Rad CFX96 real-time PCR instrument (Bio-Rad, USA). The result was shown in FIGS. 13A-13C.

FIGS. 13A-13C show the melting curves of 83 real-time PCRs using 20 mediator probes and 6 fluorescent probes; wherein, in said real-time PCR, 41 primers, 20 mediator probes and 6 fluorescent probe as described in Table 5, polymerase TaqHS and cellular genomic DNA obtained from normal males (83 samples in total) are used; FIG. 13A shows the melting curve obtained from ROX detection channel; FIG. 13B shows the melting curve obtained from FAM detection channel; FIG. 13C shows the melting curve obtained from Cy5 detection channel; and, the solid line in the figure shows the experimental result using cellular genomic DNA (83 samples) as a template; the dashed line represents the experimental result using water as a template (negative control).

The result of FIGS. 13A-13C show that in the melting curve obtained from ROX detection channel, 8 specific distinguishable peaks (marked as 8 peaks, i.e. 242, ZF, 82, 86, 152, 145, SRY, and 84, respectively) appeared, the melting points of which corresponded to the duplexes formed by fluorescent probe UP1 or UP2 and the extension products of the mediator sequences in Mediator probes 242-MP, ZF-MP, 82-MP, 86-MP, 152-MP, 145-MP, SRY-MP, and 84-MP; in the melting curve obtained from FAM detection channel, 6 distinguishable specific peaks (marked as 6 peaks, i.e. 124, 127, 128, 133, 143, and 134, respectively), the melting points of which corresponded to the duplexes formed by fluorescent probe UP3 or UP4 and the extension products of the mediator sequences in Mediator probes 124-MP, 127-MP, 128-MP, 133-MP, 143-MP, and 134-MP, respectively; in the melting curve obtained from Cy5 detection channel, 6 specific distinguishable peaks (marked as 6 peaks, i.e. 155, 154, 157, 254, 239, and 255, respectively) appeared, the melting points of which corresponded to the duplexes formed by fluorescent probe UP5 or UP6 and the extension products of the mediator sequences in Mediator probes 155-MP, 154-MP, 157-MP, 254-MP, 239-MP, and 255-MP, respectively. These experimental results show that by using 20 mediator probes and 6 fluorescent probes, simultaneous detection and discrimination (i.e. 20-plex detection) of 20 target sequences could be achieved in a single post-PCR MCA assay.

In addition, the result of FIGS. 13A-13C also show that for the detected 83 samples, the shapes of the 83 melting curves obtained were substantively the same, and in these melting curves, the $T_m$ values of 20 specific peaks were substantively the same (CV<0.5%). This shows that said 20-plex PCR MCA assay had very excellent repeatability and reliability.

In order to further confirm the reliability of said methods above, another 92 samples were subjected to blind test by using said methods. Among said 92 samples, 33 samples were cellular genomic DNA obtained from different normal males; 58 samples were cellular genomic DNA obtained from different males having microdeletions on Y chromosome; 1 sample was cellular genomic DNA obtained from a normal female. The 92 samples were detected by using said 20-plex PCR MCA assay.

Later, traditional PCR-agarose gel electrophoresis was also used to detect the 92 samples. The result shows that the detection result of 20-plex PCR MCA assay was completely concordant with the detection result of PCR-agarose gel electrophoresis. This also shows that the 20-plex PCR MCA assay of the invention had very excellent reliability. Some typical detection results of said 20-plex PCR MCA assay were shown in FIG. 14.

Figure 14:
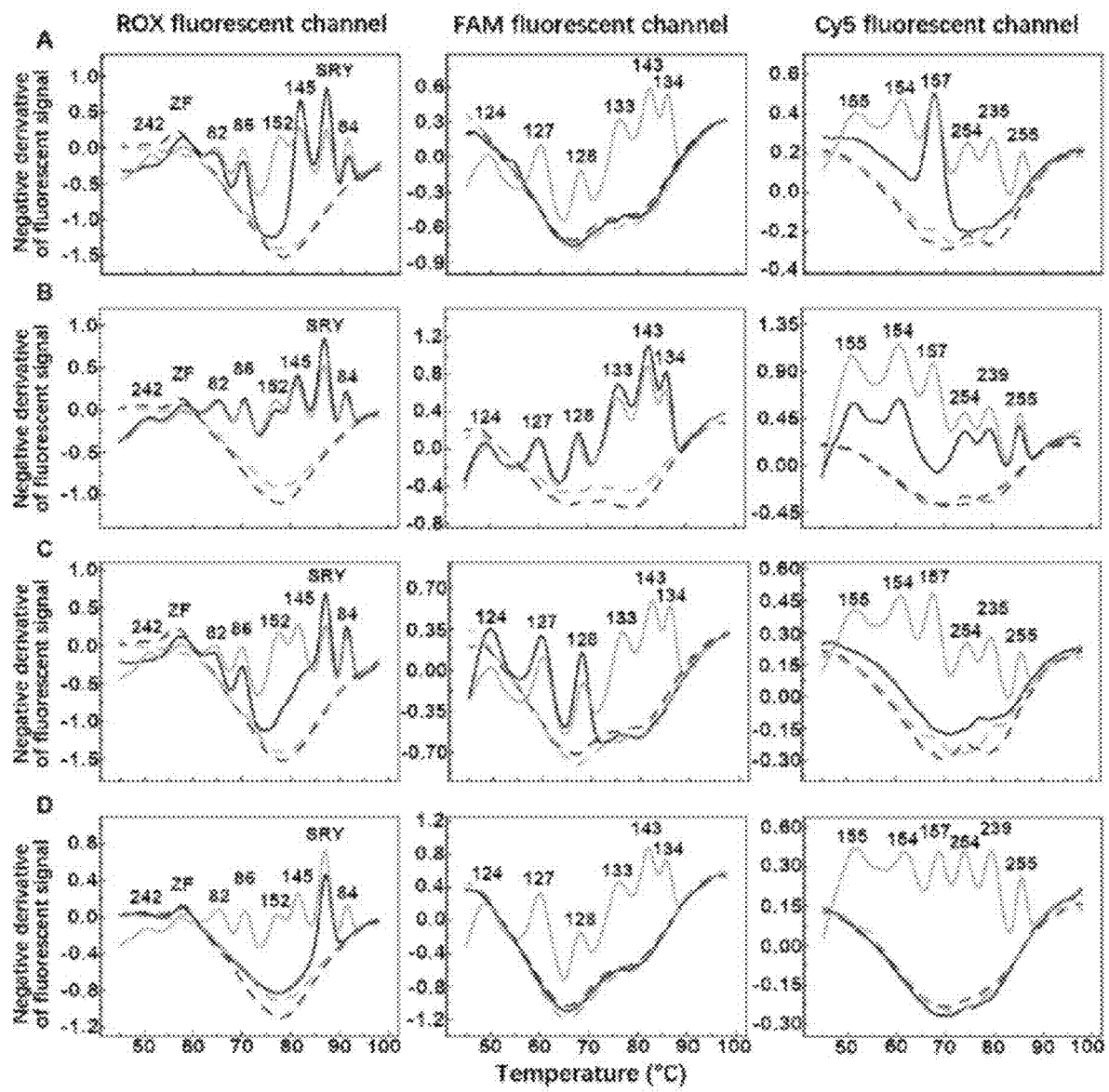
FIG. 14 shows the representative experimental result obtained by detecting 92 samples by using 20-plex PCR MCA; wherein, the black solid line shows the experimental result using cellular genomic DNA from males having microdeletions on Y chromosome, as a template; the grey solid line shows the experimental result using normal male cellular genomic DNA as a template; the dashed black line represents the experimental result using normal female cellular genomic DNA as a template; the dashed grey line represents the experimental result using water as a template.

FIG. 14 shows the representative experimental result obtained by detecting 92 samples by using 20-plex PCR MCA assay; wherein, the black solid line shows the experimental result using cellular genomic DNA from males having microdeletions on Y chromosome, as a template; the grey solid line shows the experimental result using cellular genomic DNA from normal males as a template; the dashed black line represents the experimental result using cellular genomic DNA from a normal female as a template; the dashed grey line represents the experimental result using water as a template. These experimental results show again that by using 20 mediator probes and 6 fluorescent probes, it can achieve the simultaneous detection and discrimination (i.e. 20-plex detection) of 20 target sequences in a single post-PCR MCA assay.

Although the specific embodiments of the invention have been described in detail, those skilled in the art would understand that, based on all the disclosed teachings, various modifications and changes can be made to details, and such modifications and changes are within the scope of the invention. The scope of the invention is given by the appended claims and any equivalents thereof.

TABLE 4

Sequences and amounts of the primers and probes used in Example 8

| Target gene | Primer and probe | Conc. (μM) | Sequence (5' → 3') | SEQ ID NO |
|---|---|---|---|---|
| | Common amplification primer | 0.8 | GCAAGCCCTCACGTAGCGAA | 12 |
| | Fluorescent probe UP1 | 0.0375 | ROX-CGAGCAAAAAGAAGTGTGAGAGGTGTGATGAGCTCG-BHQ2 | 13 |
| sY82 | Upstream primer H-82-F | 0.006 | GCAAGCCCTCACGTAGCGAAATCCTGCCCTTCTGAATCTC | 14 |
| | Downstream primer H-82-R | 0.006 | GCAAGCCCTCACGTAGCGAACTGATGGATGATGGGATGTTTG | 15 |
| | Mediator probe 82-MP | 0.006 | CACCTCTCACATGTATTTAGCAGCAACATGGCTAGAACTGGAGG-$C_7NH_2$ | 16 |

TABLE 4-continued

Sequences and amounts of the primers and probes used in Example 8

| Target gene | Primer and probe | Conc. (μM) | Sequence (5' → 3') | SEQ ID NO |
|---|---|---|---|---|
| sY86 | Upstream primer H-86-F | 0.006 | GCAAGCCCTCACGTAGCGAAGCCCCTTAAACAACAACCT | 17 |
|  | Downstream primer H-86-R | 0.006 | GCAAGCCCTCACGTAGCGAAACAGGGAGAAGACAGCATCT | 18 |
|  | Mediator probe 86-MP | 0.006 | TCATCACACCTCTGAGATCAAGCTATGGCCAGGGCTGG-C$_7$NH$_2$ | 19 |
| sY242 | Upstream primer H-242-F | 0.015 | GCAAGCCCTCACGTAGCGAAGCAATGGAGTAGCCAGACA | 20 |
|  | Downstream primer H-242-R | 0.015 | GCAAGCCCTCACGTAGCGAATCTGCCACTAAACTGTAAGCTC | 21 |
|  | Mediator probe242-MP | 0.02 | CGCACTTCTTTTGATGGGGGGCAAGGCTGACAGC-C$_7$NH$_2$ | 22 |
| ZFX/Y | Upstream primer H-ZF-F | 0.01 | GCAAGCCCTCACGTAGCGAAGAAATACCGCTGTACTGACTG | 23 |
|  | Downstream primer H-ZF-R | 0.01 | GCAAGCCCTCACGTAGCGAAGGAAAGTTCTTGCTGTGGAC | 24 |
|  | Mediator probe ZF-MP | 0.01 | TCTCACACTTCTTCACAGAATTTACACTTGTGCATTTTGTTGGCTCC-C$_7$NH$_2$ | 25 |

TABLE 5

Sequences and amounts of the primers and probes used in Example 9

| Target gene | Primers and probes | Conc. (nM) | Sequence (5' → 3') | SEQ ID NO |
|---|---|---|---|---|
|  | Common amplification primers | 3200 | GCAAGCCCTCACGTAGCGAA | 12 |
|  | Fluorescent probe UP1 | 60 | ROX-CGAGCAAAAAGAAGTGTGAGAGGTGTGATGAGCTCG-BHQ2 | 13 |
| sY82 | Upstream primer H-82-F | 7.5 | GCAAGCCCTCACGTAGCGAAATCCTGCCCTTCTGAATCTC | 14 |
|  | Downstream primer H-82-R | 7.5 | GCAAGCCCTCACGTAGCGAACTGATGGATGATGGGATGTTTG | 15 |
|  | Mediator probe 82-MP | 6.0 | CACCTCTCACATGTATTTAGCAGCAACATGGCTAGAACTGGAGG-C$_7$NH$_2$ | 16 |
| sY86 | Upstream primer H-86-F | 7.5 | GCAAGCCCTCACGTAGCGAAGCCCCTTAAACAACAACCT | 17 |
|  | Downstream primer H-86-R | 7.5 | GCAAGCCCTCACGTAGCGAAACAGGGAGAAGACAGCATCT | 18 |
|  | Mediator probe 86-MP | 6.0 | TCATCACACCTCTGAGATCAAGCTATGGCCAGGGCTGG-C$_7$NH$_2$ | 19 |
| sY242 | Upstream primer H-242-F | 27.5 | GCAAGCCCTCACGTAGCGAAGCAATGGAGTAGCCAGACA | 20 |
|  | Downstream primer H-242-R | 27.5 | GCAAGCCCTCACGTAGCGAATCTGCCACTAAACTGTAAGCTC | 21 |
|  | Mediator probe 242-MP | 200.0 | CGCACTTCTTTTGATGGGGGGCAAGGCTGACAGC-C$_7$NH$_2$ | 22 |
| ZFX/Y | Upstream primer H-ZF-F | 7.5 | GCAAGCCCTCACGTAGCGAAGAAATACCGCTGTACTGACTG | 23 |
|  | Downstream primer H-ZF-R | 7.5 | GCAAGCCCTCACGTAGCGAAGGAAAGTTCTTGCTGTGGAC | 24 |
|  | Mediator probe ZF-MP | 8.0 | TCTCACACTTCTTCACAGAATTTACACTTGTGCATTTTGTTGGCTCC-C$_7$NH$_2$ | 25 |
|  | Fluorescent probe UP2 | 50 | ROX-CGGCGGAGTGGGCACGGAGAGCGCTGGACAGTGT + G + GA + C + CCACGTCTCGCAGCAGGCCGCCG-BHQ2 | 26 |
| sY152 | Upstream primer H-152-F | 7.5 | GCAAGCCCTCACGTAGCGAAGCGCTCTAAGAATTGGGTAAAG | 27 |
|  | Downstream primer H-152-R | 7.5 | GCAAGCCCTCACGTAGCGAAACAGGAGGGTACTTAGCAG | 28 |
|  | Mediator probe 152-MP | 60 | AGCGCTCTCCGTCTGCCATGTTTCAGCTCTTTGACAGCA-C$_7$NH$_2$ | 29 |
| sY145 | Upstream primer H-145-F | 7.5 | GCAAGCCCTCACGTAGCGAACTTCCTACATTTGTCTTCATAACTTC | 30 |
|  | Downstream primer H-145-R | 7.5 | GCAAGCCCTCACGTAGCGAAAGAGTGTGATTTCTCATATTTGGTC | 31 |
|  | Mediator probe 145-MP | 200 | ACACTGTCCAGCGACTTTTGGCTGGGCTGACTACCAGT-C$_7$NH$_2$ | 32 |
| SRY | Upstream primer H-SRY-F | 7.5 | GCAAGCCCTCACGTAGCGAACCAGTGGAAAATGCTTACTGA | 33 |
|  | Downstream primer H-SRY-R | 7.5 | GCAAGCCCTCACGTAGCGAAATCTGCGGGAAGCAAACTG | 34 |
|  | Mediator probe SRY-MP | 200 | GTCCACACTGTATCGACCTCGTCGGAAGGCGAAGATG-C$_7$NH$_2$ | 35 |
| sY84 | Upstream primer H-84-F | 30 | GCAAGCCCTCACGTAGCGAACCTATTTGTTTTAAGGTGCCATTC | 36 |
|  | Downstream primer H-84-R | 30 | GCAAGCCCTCACGTAGCGAAAGCTTGCATTAGGCAGACAC | 37 |
|  | Mediator probe 84-MP | 200 | CCTGCTGCGAGAGCAAATTCCCTTAATCTGCACGAAACATGGG-C$_7$NH$_2$ | 38 |
|  | Fluorescent probe UP3 | 40 | FAM-AAGCCCAAAAAGAGAACAGTATCAGTCACACGGGCTT-BHQ1 | 39 |
| sY124 | Upstream primer H-124-F | 30 | GCAAGCCCTCACGTAGCGAATGCCACAGTAAAATGAAGCATC | 40 |
|  | Downstream primer H-124-R | 30 | GCAAGCCCTCACGTAGCGAATGTTTTCTTCCAGGGCAATG | 41 |
|  | Mediator probe 124-MP | 200 | TTCTCTTTTTGGGTCTAGAAGTGCCAtCCGAAACCA-C$_7$NH$_2$ | 42 |
| sY127 | Upstream primer H-127-F | 22.5 | GCAAGCCCTCACGTAGCGAAGAATATAGCCCAAAACTAATCAGCA | 43 |
|  | Downstream primer H-127-R | 22.5 | GCAAGCCCTCACGTAGCGAAAACATCTGGCTCACCCATATAAG | 44 |
|  | Mediator probe 127-MP | 200 | ATACTGTTCTCTAGCACCCACTGGAATCTACCAAAGCCCA-C$_7$NH$_2$ | 45 |

TABLE 5-continued

Sequences and amounts of the primers and probes used in Example 9

| Target gene | Primers and probes | Conc. (nM) | Sequence (5' → 3') | SEQ ID NO |
|---|---|---|---|---|
| sY128 | Upstream primer H-128-F | 7.5 | GCAAGCCCTCACGTAGCGAAAGTGAACAGGATTGGCAAAGA | 46 |
| | Downstream primer H-128-R | 7.5 | GCAAGCCCTCACGTAGCGAAGCAAAACTTTCAACTTCCAAATTCA | 47 |
| | Mediator probe 128-MP | 200 | GTGACTGATACCATGAGTGGACATAAGCAAAGCACTTTGGATCA-$C_7$-$NH_2$ | 48 |
| | Fluorescent probe UP4 | 75 | FAM-GCGCGCCAGCGGACGAGGCTGTGCACCGGTCGGAGGTGGGGGCGCGC-BHQ1 | 49 |
| sY133 | Upstream primer H-133-F | 7.5 | GCAAGCCCTCACGTAGCGAATTCACCAGGACAGAGCCA | 50 |
| | Downstream primer H-133-R | 7.5 | GCAAGCCCTCACGTAGCGAATGGCAATGTTTTCTCCCTTCA | 51 |
| | Mediator probe 133-MP | 200 | CACAGCCTCGTCCCATCATGAACTCACACATGCACACACATCC-$C_7$-$NH_2$ | 52 |
| sY143 | Upstream primer H-143-F | 15 | GCAAGCCCTCACGTAGCGAAGCAGGATGAGAAGCAGGTAG | 53 |
| | Downstream primer H-143-R | 15 | GCAAGCCCTCACGTAGCGAACCTGACATCTAAATAATCTGTGGTG | 54 |
| | Mediator probe 143-MP | 200 | GACCGGTGCACCAATGAAAGAACCCCTCCACAATGAAAAGCCT-$C_7$-$NH_2$ | 55 |
| sY134 | Upstream primer H-134-F | 7.5 | GCAAGCCCTCACGTAGCGAAATTCTACTTGAAGCGTTCTGTGA | 56 |
| | Downstream primer H-134-R | 7.5 | GCAAGCCCTCACGTAGCGAACAACCACTGCCAAAACTTTCA | 57 |
| | Mediator probe 134-MP | 100 | CCCACCTCCGACCACCCAAGCAAAACACCTACTTTCCACT-$C_7$-$NH_2$ | 58 |
| | Fluorescent probe UP5 | 60 | Cy5-GCTGCAAAAAACTCAACGATGTGGAAGTCAGCAGC-BHQ2 | 59 |
| sY155 | Upstream primer H-155-F | 15 | GCAAGCCCTCACGTAGCGAAAGCTCAGAGAAACTTACAACACT | 60 |
| | Downstream primer H-155-R | 15 | GCAAGCCCTCACGTAGCGAATGCATTTGAATGTGTAGTGGAGA | 61 |
| | Mediator probe 155-MP | 200 | GCTGAGTTTTTGGGTGGTACAGAGATATTTATGACGGATCCCAACA-$C_7$-$NH_2$ | 62 |
| sY154 | Upstream primer H-154-F | 15 | GCAAGCCCTCACGTAGCGAATTTGCACCAGGATTAAGTGAAGA | 63 |
| | Downstream primer H-154-R | 15 | GCAAGCCCTCACGTAGCGAAGTCAGATGTAAGATTGATGCCA | 64 |
| | Mediator probe 154-MP | 200 | ATCGTTGAGTTGGTTCCTCCAGAGCCAGGATGTAACC-$C_7$-$NH_2$ | 65 |
| sY157 | Upstream primer H-157-F | 7.5 | GCAAGCCCTCACGTAGCGAAGCAAAACATTGGGAATATCTTGGA | 66 |
| | Downstream primer H-157-R | 7.5 | GCAAGCCCTCACGTAGCGAATACAGGTTATCCACATTTCTTATCT | 67 |
| | Mediator probe 157-MP | 40 | TTCCACATCGTCGTTGTAATAGCAGAAGGTAGGAGATCACTAAAGTGGC-$C_7$-$NH_2$ | 68 |
| | Fluorescent probe UP6 | 60 | Cy5-CCGGCGGGGAGGGACCGTCGTGGCAGGAGGAGCAGCTCACCAGGCCGCCGG-BHQ2 | 69 |
| sY254 | Upstream primer H-254-F | 7.5 | GCAAGCCCTCACGTAGCGAATTTTGTACTTCCTGGAGGTTTAG | 70 |
| | Downstream primer H-254-R | 7.5 | GCAAGCCCTCACGTAGCGAACCAATCTCAGTTTCATCCATCT | 71 |
| | Mediator probe254-MP | 200 | CCACGACGGTCTGGTCATTCGGGGATAAATGGGGGAGAAATTTCCA-$C_7$-$NH_2$ | 72 |
| sY239 | Upstream primer H-239-F | 7.5 | GCAAGCCCTCACGTAGCGAAGTGTGTTTGTTTTTGTTTTTGTGAC | 73 |
| | Downstream primer H-239-R | 7.5 | GCAAGCCCTCACGTAGCGAACAGGAAATCTTTCTAAGTGGACA | 74 |
| | Mediator probe 239-MP | 200 | CTCCTGCCACGAGGAGCCATGTGCAGAAAAATTCACTGATGC-$C_7$-$NH_2$ | 75 |
| sY255 | Upstream primer H-255-F | 7.5 | GCAAGCCCTCACGTAGCGAATTACAGGATTCGGCGTGA | 76 |

The invention claimed is:

1. A probe set, comprising a detection probe, and at least two mediator probes, wherein, said mediator probes each independently comprises in 5' to 3' direction, a mediator sequence and a target specific sequence, said target specific sequence comprises a sequence complementary to a target nucleic acid sequence, said mediator sequence comprises a sequence not complementary to said target nucleic acid sequence, and, the mediator sequences comprised in at least two mediator probes are different from each other; and said detection probe comprises in 3' to 5' direction, at least two capture sequences which are complementary to the mediator sequences or parts thereof of the at least two mediator probes, and are able to hybridize with and capture the mediator sequences of the at least two mediator probes, and a templating sequence; and, said detection probe is labeled with a reporter group and a quencher group, wherein, said reporter group can generate a signal, and, said quencher group can absorb or quench the signal generated by said reporter group; and, the signal, as generated by said detection probe when hybridizing with at least one of its complementary sequences, is different from the signal, as generated when not hybridizing with one of its complementary sequences.

2. The probe set according to claim 1, wherein said probe set has one or more of the following features:

(i) said probe set comprises at least 3, at least 4, at least 5, at least 6, at least 7, at least 8, at least 9, at least 10, at least 12, at least 15, or at least 20 mediator probes;

(ii) said probe set comprises at least 3 mediator probes and the mediator sequences comprised in all the mediator probes are different from each other;

(iii) the target specific sequences comprised in at least two or all the mediator probes are different from each other;

(iv) at least two or all the mediator probes target to different target nucleic acid sequences, respectively; and (v) said probe set comprises more than one detection probe; and each detection probe is independently labeled with identical or different reporter groups.

3. The probe set according to claim 1, wherein, said mediator probes each independently have one or more of the following features:

(a) said mediator probes each independently comprise or consist of naturally occurring nucleotides, modified nucleotides, unnatural nucleotides, or any combination thereof;
(b) the mediator sequence of each mediator probe comprises a modified nucleotide, an unnatural nucleotide, or any combination thereof;
(c) said mediator probes each independently have a length of 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, or 900-1000 nt;
(d) the target specific sequences in said mediator probes each independently have a length of 10-20 nt, 20-30 nt, 30-40 nt, 40-50 nt, 50-60 nt, 60-70 nt, 70-80 nt, 80-90 nt, 90-100 nt, 100-150 nt, 150-200 nt, 200-250 nt, 250-300 nt, 300-350 nt, 350-400 nt, 400-450 nt, or 450-500 nt;
(e) the mediator sequences in said mediator probes each independently have a length of 5-10 nt, 10-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, or 130-140 nt; and
(f) at least one mediator probe has a 3'-OH end, or the 3'-end thereof is blocked.

4. The probe set according to claim 1, wherein said detection probe has one or more of the following features:
(a) said detection probe comprises or consists of naturally occurring nucleotides, modified nucleotides, unnatural nucleotides, or any combination thereof;
(b) said detection probe has a length of 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, or 900-1000 nt;
(c) each capture sequence in said detection probe independently has a length of 10-20 nt, 20-30 nt, 30-40 nt, 40-50 nt, 50-60 nt, 60-70 nt, 70-80 nt, 80-90 nt, 90-100 nt, 100-150 nt, 150-200 nt, 200-250 nt, 250-300 nt, 300-350 nt, 350-400 nt, 400-450 nt, or 450-500 nt;
(d) the templating sequence in said detection probe has a length of 1-5 nt, 5-10 nt, 10-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, or 800-900 nt;
(e) said detection probe is a self-quenching probe;
(f) in said detection probe, the reporter group is a fluorescent group; and, the quencher group is a molecule or a group capable of absorbing or quenching fluorescence;
(g) said detection probe is resistant to nuclease activity;
(h) said detection probe is linear or has a hairpin structure;
(i) said detection probe comprises multiple capture sequences; and, said multiple capture sequences are arranged in a contiguous manner, or arranged in such a manner that they are spaced by a linking sequence; and,
(j) said detection probe comprises multiple capture sequences; and, said multiple capture sequences are arranged in an overlapping manner.

5. The probe set according to claim 1, wherein said detection probe has one or more of the following features:
(a) the distance between said reporter group and said quencher group is 10-80 nt or longer;
(b) said detection probe is resistant to 5' nuclease activity;
(c) said detection probe has a main chain comprising a modification resistant to nuclease activity; and (d) said detection probe has a main chain comprising phosphorothioate bond, alkyl phosphate triester bond, aryl phosphate triester bond, alkyl phosphonate bond, aryl phosphonate bond, hydrogenated phosphate bond, alkyl phosphoramidate bond, aryl phosphoramidate bond, 2'-O-aminopropyl modification, 2'-O-alkyl modification, 2'-O-allyl modification, 2'-O-butyl modification, and/or 1-(4'-thio-PD-ribofuranosyl) modification.

6. A kit comprising one or more probe sets as defined in claim 1.

7. The kit according to claim 6, wherein said kit has one or more of the following features:
(i) said kit comprises at least 2, at least 3, at least 4, at least 5, at least 6, at least 7, at least 8, at least 9, or at least 10 probe sets;
(ii) at least two or all the mediator probes in the kit target to different target nucleic acid sequences, respectively;
(iii) the mediator sequences comprised in at least two or all the mediator probes in the kit are different from each other;
(iv) the target specific sequences comprised in at least two or all the mediator probes in the kit are different from each other;
(v) the detection probes in the kit are independently labeled with the same reporter groups; and
(vi) the detection probes in the kit are independently labeled with different reporter groups.

8. The kit according to claim 6, wherein the kit further comprises: a first oligonucleotide sequence, a second oligonucleotide sequence, a common primer, an enzyme having 5' nuclease activity, a nucleic acid polymerase, an agent for nucleic acid hybridization, an agent for cleavage of a mediator probe, an agent for nucleic acid extension, an agent for nucleic acid amplification, an agent for reverse transcription, or any combination thereof.

9. The kit according to claim 8, wherein the kit comprises a first oligonucleotide sequence which has one or more of the following features:
(1) said first oligonucleotide sequence comprises a sequence complementary to a target nucleic acid sequence; and, when hybridizing with the target nucleic acid sequence, said first oligonucleotide sequence is located upstream to the target specific sequence of a mediator probe;
(2) said first oligonucleotide sequence comprises or consists of naturally occurring nucleotides, modified nucleotides, unnatural nucleotides, or any combination thereof;
(3) said first oligonucleotide sequence has a length of 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, or 140-150 nt; and
(4) said first oligonucleotide sequence is a primer specific for a target nucleic acid sequence or a probe specific for a target nucleic acid sequence.

10. The kit according to claim 8, wherein the kit comprises a second oligonucleotide sequence which has one or more of the following features:
(1) said second oligonucleotide sequence comprises a sequence complementary to a target nucleic acid sequence; and, when hybridizing with said target nucleic acid sequence, said second oligonucleotide sequence is located downstream to the target specific sequence of a mediator probe;

(2) said second oligonucleotide sequences comprises or consists of naturally occurring nucleotides, modified nucleotides, unnatural nucleotides, or any combination thereof; and (3) said second oligonucleotide sequences has a length of 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, or 140-150 nt.

11. The kit according to claim 8, wherein the kit comprises a first oligonucleotide sequence, a second oligonucleotide sequence and a common primer; and wherein the first oligonucleotide sequence and the second oligonucleotide sequence have an identical oligonucleotide sequence at 5' end; and, the common primer has a sequence complementary to the identical oligonucleotide sequence;

optionally, said common primer has one or more of the following features:

(a) said common primer comprises or consists of naturally occurring nucleotides, modified nucleotides, unnatural nucleotides, or any combination thereof; and (b) said common primer has a length of 8-15 nt, 15-20 nt, 20-30 nt, 30-40 nt, or 40-50 nt.

12. The kit according to claim 8, wherein the kit comprises an enzyme having 5' nuclease activity or a nucleic acid polymerase, and said enzyme having 5' nuclease activity or said nucleic acid polymerase has one or more of the following features:

(1) said enzyme having 5' nuclease activity or said nucleic acid polymerase is a nucleic acid polymerase having 5' nuclease activity;

(2) said enzyme having 5' nuclease activity or said nucleic acid polymerase is a DNA polymerase having 5' nuclease activity;

(3) said enzyme having 5' nuclease activity or said nucleic acid polymerase is a DNA polymerase originated from a bacterium selected from: *Thermus aquaticus* (Taq), *Thermus thermophiles* (Tth), *Thermus filiformis*, *Therrnis flavus*, *Thermococcus literalis*, *Thermus antranildanii*, *Thermus caldophllus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus thermophllus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosiphoafricanus*, *Pyrococcus woesei*, *Pyrococcus horikoshii*, *Pyrococcus abyssi*, *Pyrodictium occultum*, *Aquifexpyrophilus* and *Aquifex aeolieus*; and (4) said enzyme having 5' nuclease activity or said nucleic acid polymerase is Taq polymerase.

13. A kit comprising m detection probes and n mediator probes, wherein, n is an integer of ≥2, m is an integer less than n and greater than 0, and, each mediator probe independently comprises in 5' to 3' direction, a mediator sequence and a target specific sequence, said target specific sequence comprises a sequence complementary to a target nucleic acid sequence, said mediator sequence comprises a sequence not complementary to said target nucleic acid sequence, and, the mediator sequences comprised in at least two mediator probes are different from each other; and each detection probe independently comprises in 3' to 5' direction, one or more capture sequences complementary to one or more mediator sequences or parts thereof, and a templating sequence; and, said m detection probes comprise a plurality of capture sequences, which are complementary to the mediator sequences or parts thereof of the mediator probes, respectively; and, wherein at least one of the detection probes comprises at least two capture sequences, which are complementary to the mediator sequences or parts thereof of at least two mediator probes, and are able to hybridize with and capture the mediator sequences of the at least two mediator probes; and each detection probe is independently labeled with a reporter group and a quencher group, wherein, said reporter group can generate a signal, and, said quencher group can absorb or quench the signal generated by said reporter group; and, the signal, as generated by each detection probe when hybridizing with its complementary sequence, is different from the signal, as generated when not hybridizing with its complementary sequence.

14. The kit according to claim 13, wherein the kit has one or more of the following features:

(a) n is an integer of 3, 4, 5, 6, 7, 8, 9, 10, 11, 12, 13, 14, 15, 16, 17, 18, 19, 20, 25, 30, 35, 40 or greater;

(b) m is an integer of 2, 3, 4, 5, 6, 8, 10 or greater;

(c) when m≥2, said m detection probes are independently labeled with different reporter groups;

(d) the kit comprises at least 3, at least 4, at least 5, at least 6, at least 8, at least 10, at least 15, at least 20, at least 25, at least 30, at least 35, at least 40, or at least 45 mediator probes; and (e) the kit comprises at least 2, at least 3, at least 4, at least 5, at least 6, at least 8, or at least 10 detection probes.

15. The kit according to claim 13, wherein said mediator probe each independently have one or more of the following features:

(a) said mediator probes each independently comprise or consist of naturally occurring nucleotides, modified nucleotides, unnatural nucleotides, or any combination thereof;

(b) the mediator sequence of at least one mediator probe comprises a modified nucleotide, an unnatural nucleotide, or any combination thereof;

(c) said mediator probes each independently have a length of 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, or 900-1000 nt;

(d) the target specific sequences in said mediator probes each independently have a length of 10-20 nt, 20-30 nt, 30-40 nt, 40-50 nt, 50-60 nt, 60-70 nt, 70-80 nt, 80-90 nt, 90-100 nt, 100-150 nt, 150-200 nt, 200-250 nt, 250-300 nt, 300-350 nt, 350-400 nt, 400-450 nt, or 450-500 nt;

(e) the mediator sequences in said mediator probes each independently have a length of 5-10 nt, 10-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, or 130-140 nt; and (f) the mediator sequences comprised in at least two or all the mediator probes are different from each other;

(g) the target specific sequences comprised in at least two or all the mediator probes are different from each other; and (h) at least two or all the mediator probes target to different target nucleic acid sequences, respectively.

16. The kit according to claim 13, wherein each detection probe independently has one or more of the following features:

(a) each detection probe independently comprises or consists of naturally occurring nucleotides, modified nucleotides, unnatural nucleotides, or any combination thereof;
(b) each detection probe independently has a length of 15-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, 800-900 nt, or 900-1000 nt;
(c) each capture sequence in each detection probe independently has a length of 10-20 nt, 20-30 nt, 30-40 nt, 40-50 nt, 50-60 nt, 60-70 nt, 70-80 nt, 80-90 nt, 90-100 nt, 100-150 nt, 150-200 nt, 200-250 nt, 250-300 nt, 300-350 nt, 350-400 nt, 400-450 nt, or 450-500 nt;
(d) the templating sequence in each detection probe independently has a length of 1-5 nt, 5-10 nt, 10-20 nt, 20-30 nt, 30-40 nt, 40-50 nt, 50-60 nt, 60-70 nt, 70-80 nt, 80-90 nt, 90-100 nt, 100-200 nt, 200-300 nt, 300-400 nt, 400-500 nt, 500-600 nt, 600-700 nt, 700-800 nt, or 800-900 nt;
(e)
(e) at least one detection probe is a self-quenching probe;
(f) the reporter group is a fluorescent group; and, the quencher group is a molecule or a group capable of absorbing or quenching fluorescence;
(g) at least one detection probe is resistant to nuclease activity;
(h) each detection probe independently is linear or has a hairpin structure;
(i) at least one detection probe comprises multiple capture sequences; and, said multiple capture sequences are arranged in a contiguous manner, or arranged in such a manner that they are spaced by a linking sequence;
(j) at least one detection probe comprises multiple capture sequences; and, said multiple capture sequences are arranged in an overlapping manner;
(k) said reporter group is located upstream to said quencher group; or, said reporter group is located downstream to said quencher group;
(l) the distance between said reporter group and said quencher group is 10-80 nt or longer;
(m) at least one detection probe is resistant to 5' nuclease activity;
(n) at least one detection probe has a main chain comprising a modification resistant to nuclease activity; and
(o) at least one detection probe has a main chain comprising phosphorothioate bond, alkyl phosphate triester bond, aryl phosphate triester bond, alkyl phosphonate bond, aryl phosphonate bond, hydrogenated phosphate bond, alkyl phosphoramidate bond, aryl phosphoramidate bond, 2'-O-aminopropyl modification, 2'-O-alkyl modification, 2'-O-allyl modification, 2'-O-butyl modification, and/or 1-(4'-thio-PD-ribofuranosyl) modification.

17. The kit according to claim 13, wherein the kit further comprises: an first oligonucleotide sequence, a second oligonucleotide sequence, a common primer, an enzyme having 5' nuclease activity, a nucleic acid polymerase, an agent for nucleic acid hybridization, an agent for cleavage of a mediator probe, an agent for nucleic acid extension, an agent for nucleic acid amplification, an agent for reverse transcription, or any combination thereof.

18. The kit according to claim 17, wherein said kit comprises a first oligonucleotide sequence and a second oligonucleotide sequence, characterized by one or more of the following features:

(1) said first oligonucleotide sequence comprises a sequence complementary to a target nucleic acid sequence; and, when hybridizing with the target nucleic acid sequence, said first oligonucleotide sequence is located upstream to the target specific sequence of a mediator probe;
(2) said first oligonucleotide sequences comprises or consists of naturally occurring nucleotides, modified nucleotides, unnatural nucleotides, or any combination thereof;
(3) said first oligonucleotide sequences has a length of 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, or 140-150 nt;
(4) said first oligonucleotide sequence, upon hybridization with a target nucleic acid sequence, is each independently located far from the upstream of the mediator probe, or located near the upstream of the mediator probe, or has a partially overlapping sequence with the target specific sequence of the mediator probe;
(5) said first oligonucleotide sequence is a primer specific for a target nucleic acid sequence or a probe specific for a target nucleic acid sequence;
(6) said second oligonucleotide sequence comprises a sequence complementary to a target nucleic acid sequence; and, when hybridizing with said target nucleic acid sequence, said second oligonucleotide sequence is located downstream to the target specific sequence of a mediator probe;
(7) said second oligonucleotide sequences comprises or consists of naturally occurring nucleotides, modified nucleotides, unnatural nucleotides, or any combination thereof; and
(8) said second oligonucleotide sequences has a length of 15-20 nt, 20-30 nt, 30-40 nt, 40-50 nt, 50-60 nt, 60-70 nt, 70-80 nt, 80-90 nt, 90-100 nt, 100-110 nt, 110-120 nt, 120-130 nt, 130-140 nt, or 140-150 nt.

19. The kit according to claim 17, wherein the kit comprises a first oligonucleotide sequence, a second oligonucleotide sequence and a common primer; and wherein the first oligonucleotide sequence and the second oligonucleotide sequence have an identical oligonucleotide sequence at 5' end; and the common primer has a sequence complementary to the identical oligonucleotide sequence;

optionally, said common primer has one or more of the following features:
(a) said common primer comprises or consists of naturally occurring nucleotides, modified nucleotides, unnatural nucleotides, or any combination thereof; and
(b) said common primer has a length of 8-15 nt, 15-20 nt, 20-30 nt, 30-40 nt, or 40-50 nt.

20. The kit according to claim 17, wherein the kit comprises an enzyme having 5' nuclease activity or a nucleic acid polymerase, and said enzyme having 5' nuclease activity or said nucleic acid polymerase has one or more of the following features:
(1) said enzyme having 5' nuclease activity or said nucleic acid polymerase is a nucleic acid polymerase having 5' nuclease activity;
(2) said enzyme having 5' nuclease activity or said nucleic acid polymerase is a DNA polymerase having 5' nuclease activity;
(3) said enzyme having 5' nuclease activity or said nucleic acid polymerase is a DNA polymerase originated from a bacterium selected from: *Thermus aquaticus* (Taq), *Thermus thermophiles* (Tth), *Thermus filiformis, Therrnis flavus, Thermococcus literalis, Thermus antra-*

*nildanii, Thermus caldophllus, Thermus chliarophilus, Thermus flavus, Thermus igniterrae, Thermus lacteus, Thermus oshimai, Thermus ruber, Thermus rubens, Thermus scotoductus, Thermus silvanus, Thermus thermophllus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosiphoafricanus, Pyrococcus* woesei, *Pyrococcus horikoshii, Pyrococcus abyssi, Pyrodictium occultum, Aquifexpyrophilus* and *Aquifex aeolieus*; and (4) said enzyme having 5' nuclease activity or said nucleic acid polymerase is Taq polymerase.

\* \* \* \* \*

SEQUENCE LISTING

<160> NUMBER OF SEQ ID NOS: 78

<210> SEQ ID NO 1
<211> LENGTH: 27
<212> TYPE: DNA
<213> ORGANISM: Artificial Sequence
<220> FEATURE:
<223> OTHER INFORMATION: primer

<400> SEQUENCE: 1
tgttttcctt tacttactac acctcag                27

<210> SEQ ID NO 2
<211> LENGTH: 24
<212> TYPE: DNA
<213> ORGANISM: Artificial Sequence
<220> FEATURE:
<223> OTHER INFORMATION: primer -continued

<400> SEQUENCE: 2
tcagtggaaa aatagcctca attc                                            24

<210> SEQ ID NO 3
<211> LENGTH: 49
<212> TYPE: DNA
<213> ORGANISM: Artificial Sequence
<220> FEATURE:
<223> OTHER INFORMATION: probe

<400> SEQUENCE: 3
aaatcgttct gggctctacg ctacagtgaa atctcgatgg agtgggtcc                 49

<210> SEQ ID NO 4
<211> LENGTH: 40
<212> TYPE: DNA
<213> ORGANISM: Artificial Sequence
<220> FEATURE:
<223> OTHER INFORMATION: probe

<400> SEQUENCE: 4
ttgtcacctg tcctagagag cgtagagccc agaacgattt                           40

<210> SEQ ID NO 5
<211> LENGTH: 52
<212> TYPE: DNA
<213> ORGANISM: Artificial Sequence
<220> FEATURE:
<223> OTHER INFORMATION: probe

<400> SEQUENCE: 5
cccggcttgt cacctgtcct agagagcgta gagcccagaa cgatttgccg gg             52

<210> SEQ ID NO 6
<211> LENGTH: 44
<212> TYPE: DNA
<213> ORGANISM: Artificial Sequence
<220> FEATURE:
<223> OTHER INFORMATION: probe

<400> SEQUENCE: 6
aaatcgttct gggctctaca gtgaaatctc gatggagtgg gtcc                      44

<210> SEQ ID NO 7
<211> LENGTH: 39
<212> TYPE: DNA
<213> ORGANISM: Artificial Sequence
<220> FEATURE:
<223> OTHER INFORMATION: probe

<400> SEQUENCE: 7
aaatcgttct gggcagtgaa atctcgatgg agtgggtcc                            39

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
attataaggc ctgctgaaaa tgac                                            24

<210> SEQ ID NO 9

```
<211> LENGTH: 25
<212> TYPE: DNA
<213> ORGANISM: Artificial Sequence
<220> FEATURE:
<223> OTHER INFORMATION: primer

<400> SEQUENCE: 9
gcaccagtaa tatgcatatt aaaac                                            25

<210> SEQ ID NO 10
<211> LENGTH: 42
<212> TYPE: DNA
<213> ORGANISM: Artificial Sequence
<220> FEATURE:
<223> OTHER INFORMATION: probe

<400> SEQUENCE: 10
aaatcgttct gggctctacg tggtagttgg agctggtggc gt                         42

<210> SEQ ID NO 11
<211> LENGTH: 35
<212> TYPE: DNA
<213> ORGANISM: Artificial Sequence
<220> FEATURE:
<223> OTHER INFORMATION: probe

<400> SEQUENCE: 11
ctctctagga caggtggtgg cgtaggcaag agtgc                                 35

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcaagccctc acgtagcgaa                                                  20

<210> SEQ ID NO 13
<211> LENGTH: 36
<212> TYPE: DNA
<213> ORGANISM: Artificial Sequence
<220> FEATURE:
<223> OTHER INFORMATION: probe

<400> SEQUENCE: 13
cgagcaaaaa gaagtgtgag aggtgtgatg agctcg                                36

<210> SEQ ID NO 14
<211> LENGTH: 40
<212> TYPE: DNA
<213> ORGANISM: Artificial Sequence
<220> FEATURE:
<223> OTHER INFORMATION: primer

<400> SEQUENCE: 14
gcaagccctc acgtagcgaa atcctgccct tctgaatctc                            40

<210> SEQ ID NO 15
<211> LENGTH: 42
<212> TYPE: DNA
<213> ORGANISM: Artificial Sequence
<220> FEATURE:
<223> OTHER INFORMATION: primer

<400> SEQUENCE: 15
```

```
gcaagccctc acgtagcgaa ctgatggatg atgggatgtt tg              42
```

<210> SEQ ID NO 16
<211> LENGTH: 44
<212> TYPE: DNA
<213> ORGANISM: Artificial Sequence
<220> FEATURE:
<223> OTHER INFORMATION: probe

<400> SEQUENCE: 16

```
cacctctcac atgtatttag cagcaacatg gctagaactg gagg            44
```

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17

```
gcaagccctc acgtagcgaa gccccttaaa caacaacct                  39
```

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18

```
gcaagccctc acgtagcgaa acagggagaa gacagcatct                 40
```

<210> SEQ ID NO 19
<211> LENGTH: 38
<212> TYPE: DNA
<213> ORGANISM: Artificial Sequence
<220> FEATURE:
<223> OTHER INFORMATION: probe

<400> SEQUENCE: 19

```
tcatcacacc tctgagatca agctatggcc agggctgg                   38
```

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20

```
gcaagccctc acgtagcgaa gcaatggagt agccagaca                  39
```

<210> SEQ ID NO 21
<211> LENGTH: 42
<212> TYPE: DNA
<213> ORGANISM: Artificial Sequence
<220> FEATURE:
<223> OTHER INFORMATION: primer

<400> SEQUENCE: 21

```
gcaagccctc acgtagcgaa tctgccacta aactgtaagc tc              42
```

<210> SEQ ID NO 22
<211> LENGTH: 34
<212> TYPE: DNA

```
<213> ORGANISM: Artificial Sequence
<220> FEATURE:
<223> OTHER INFORMATION: probe

<400> SEQUENCE: 22
cgcacttctt ttgatggggg gcaaggctga cagc                              34

<210> SEQ ID NO 23
<211> LENGTH: 41
<212> TYPE: DNA
<213> ORGANISM: Artificial Sequence
<220> FEATURE:
<223> OTHER INFORMATION: primer

<400> SEQUENCE: 23
gcaagccctc acgtagcgaa gaaataccgc tgtactgact g                      41

<210> SEQ ID NO 24
<211> LENGTH: 40
<212> TYPE: DNA
<213> ORGANISM: Artificial Sequence
<220> FEATURE:
<223> OTHER INFORMATION: primer

<400> SEQUENCE: 24
gcaagccctc acgtagcgaa ggaaagttct tgctgtggac                        40

<210> SEQ ID NO 25
<211> LENGTH: 47
<212> TYPE: DNA
<213> ORGANISM: Artificial Sequence
<220> FEATURE:
<223> OTHER INFORMATION: probe

<400> SEQUENCE: 25
tctcacactt cttcacagaa tttacacttg tgcattttgt tggctcc                47

<210> SEQ ID NO 26
<211> LENGTH: 61
<212> TYPE: DNA
<213> ORGANISM: Artificial Sequence
<220> FEATURE:
<223> OTHER INFORMATION: probe

<400> SEQUENCE: 26
cggcggagtg ggcacggaga gcgctggaca gtgtggaccc acgtctcgca gcaggccgcc  60
g                                                                  61

<210> SEQ ID NO 27
<211> LENGTH: 42
<212> TYPE: DNA
<213> ORGANISM: Artificial Sequence
<220> FEATURE:
<223> OTHER INFORMATION: primer

<400> SEQUENCE: 27
gcaagccctc acgtagcgaa gcgctctaag aattgggtaa ag                     42

<210> SEQ ID NO 28
<211> LENGTH: 39
<212> TYPE: DNA
<213> ORGANISM: Artificial Sequence
<220> FEATURE:
<223> OTHER INFORMATION: primer

<400> SEQUENCE: 28
```

```
gcaagccctc acgtagcgaa acaggagggt acttagcag                              39

<210> SEQ ID NO 29
<211> LENGTH: 39
<212> TYPE: DNA
<213> ORGANISM: Artificial Sequence
<220> FEATURE:
<223> OTHER INFORMATION: probe

<400> SEQUENCE: 29
agcgctctcc gtctgccatg tttcagctct ttgacagca                              39

<210> SEQ ID NO 30
<211> LENGTH: 46
<212> TYPE: DNA
<213> ORGANISM: Artificial Sequence
<220> FEATURE:
<223> OTHER INFORMATION: primer

<400> SEQUENCE: 30
gcaagccctc acgtagcgaa cttcctacat ttgtcttcat aacttc                      46

<210> SEQ ID NO 31
<211> LENGTH: 45
<212> TYPE: DNA
<213> ORGANISM: Artificial Sequence
<220> FEATURE:
<223> OTHER INFORMATION: primer

<400> SEQUENCE: 31
gcaagccctc acgtagcgaa agagtgtgat ttctcatatt tggtc                       45

<210> SEQ ID NO 32
<211> LENGTH: 38
<212> TYPE: DNA
<213> ORGANISM: Artificial Sequence
<220> FEATURE:
<223> OTHER INFORMATION: probe

<400> SEQUENCE: 32
acactgtcca gcgacttttg gctgggctga ctaccagt                               38

<210> SEQ ID NO 33
<211> LENGTH: 41
<212> TYPE: DNA
<213> ORGANISM: Artificial Sequence
<220> FEATURE:
<223> OTHER INFORMATION: primer

<400> SEQUENCE: 33
gcaagccctc acgtagcgaa ccagtggaaa atgcttactg a                           41

<210> SEQ ID NO 34
<211> LENGTH: 39
<212> TYPE: DNA
<213> ORGANISM: Artificial Sequence
<220> FEATURE:
<223> OTHER INFORMATION: primer

<400> SEQUENCE: 34
gcaagccctc acgtagcgaa atctgcggga agcaaactg                              39

<210> SEQ ID NO 35
<211> LENGTH: 37
<212> TYPE: DNA
```

```
<213> ORGANISM: Artificial Sequence
<220> FEATURE:
<223> OTHER INFORMATION: probe

<400> SEQUENCE: 35
gtccacactg tatcgacctc gtcggaaggc gaagatg                              37

<210> SEQ ID NO 36
<211> LENGTH: 44
<212> TYPE: DNA
<213> ORGANISM: Artificial Sequence
<220> FEATURE:
<223> OTHER INFORMATION: primer

<400> SEQUENCE: 36
gcaagccctc acgtagcgaa cctatttgtt ttaaggtgcc attc                      44

<210> SEQ ID NO 37
<211> LENGTH: 40
<212> TYPE: DNA
<213> ORGANISM: Artificial Sequence
<220> FEATURE:
<223> OTHER INFORMATION: primer

<400> SEQUENCE: 37
gcaagccctc acgtagcgaa agcttgcatt aggcagacac                           40

<210> SEQ ID NO 38
<211> LENGTH: 43
<212> TYPE: DNA
<213> ORGANISM: Artificial Sequence
<220> FEATURE:
<223> OTHER INFORMATION: probe

<400> SEQUENCE: 38
cctgctgcga gagcaaattc ccttaatctg cacgaaacat ggg                       43

<210> SEQ ID NO 39
<211> LENGTH: 39
<212> TYPE: DNA
<213> ORGANISM: Artificial Sequence
<220> FEATURE:
<223> OTHER INFORMATION: probe

<400> SEQUENCE: 39
aagcccaaaa aagagaacag tatcagtcac acggggctt                            39

<210> SEQ ID NO 40
<211> LENGTH: 42
<212> TYPE: DNA
<213> ORGANISM: Artificial Sequence
<220> FEATURE:
<223> OTHER INFORMATION: primer

<400> SEQUENCE: 40
gcaagccctc acgtagcgaa tgccacagta aaatgaagca tc                        42

<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41
gcaagccctc acgtagcgaa tgttttcttc cagggcaatg                           40
```

```
<210> SEQ ID NO 42
<211> LENGTH: 38
<212> TYPE: DNA
<213> ORGANISM: Artificial Sequence
<220> FEATURE:
<223> OTHER INFORMATION: probe

<400> SEQUENCE: 42
ttctcttttt tgggtctaga agtgccattc ggaaacca                            38

<210> SEQ ID NO 43
<211> LENGTH: 45
<212> TYPE: DNA
<213> ORGANISM: Artificial Sequence
<220> FEATURE:
<223> OTHER INFORMATION: primer

<400> SEQUENCE: 43
gcaagccctc acgtagcgaa gaatatagcc caaaactaat cagca                    45

<210> SEQ ID NO 44
<211> LENGTH: 43
<212> TYPE: DNA
<213> ORGANISM: Artificial Sequence
<220> FEATURE:
<223> OTHER INFORMATION: primer

<400> SEQUENCE: 44
gcaagccctc acgtagcgaa aacatctggc tcacccatat aag                      43

<210> SEQ ID NO 45
<211> LENGTH: 40
<212> TYPE: DNA
<213> ORGANISM: Artificial Sequence
<220> FEATURE:
<223> OTHER INFORMATION: probe

<400> SEQUENCE: 45
atactgttct ctagcaccca ctggaatcta ccaaagccca                          40

<210> SEQ ID NO 46
<211> LENGTH: 41
<212> TYPE: DNA
<213> ORGANISM: Artificial Sequence
<220> FEATURE:
<223> OTHER INFORMATION: primer

<400> SEQUENCE: 46
gcaagccctc acgtagcgaa agtgaacagg attggcaaag a                        41

<210> SEQ ID NO 47
<211> LENGTH: 45
<212> TYPE: DNA
<213> ORGANISM: Artificial Sequence
<220> FEATURE:
<223> OTHER INFORMATION: primer

<400> SEQUENCE: 47
gcaagccctc acgtagcgaa gcaaaacttt caacttccaa attca                    45

<210> SEQ ID NO 48
<211> LENGTH: 44
<212> TYPE: DNA
<213> ORGANISM: Artificial Sequence
<220> FEATURE:
```

```
<223> OTHER INFORMATION: probe

<400> SEQUENCE: 48
gtgactgata ccatgagtgg acataagcaa agcactttgg atca                              44

<210> SEQ ID NO 49
<211> LENGTH: 47
<212> TYPE: DNA
<213> ORGANISM: Artificial Sequence
<220> FEATURE:
<223> OTHER INFORMATION: probe

<400> SEQUENCE: 49
gcgcgccagc ggacgaggct gtgcaccggt cggaggtggg ggcgcgc                           47

<210> SEQ ID NO 50
<211> LENGTH: 38
<212> TYPE: DNA
<213> ORGANISM: Artificial Sequence
<220> FEATURE:
<223> OTHER INFORMATION: primer

<400> SEQUENCE: 50
gcaagccctc acgtagcgaa ttcaccagga cagagcca                                    38

<210> SEQ ID NO 51
<211> LENGTH: 41
<212> TYPE: DNA
<213> ORGANISM: Artificial Sequence
<220> FEATURE:
<223> OTHER INFORMATION: primer

<400> SEQUENCE: 51
gcaagccctc acgtagcgaa tggcaatgtt ttctcccttc a                                41

<210> SEQ ID NO 52
<211> LENGTH: 43
<212> TYPE: DNA
<213> ORGANISM: Artificial Sequence
<220> FEATURE:
<223> OTHER INFORMATION: probe

<400> SEQUENCE: 52
cacagcctcg tcccatcatg aactcacaca tgcacacaca tcc                              43

<210> SEQ ID NO 53
<211> LENGTH: 40
<212> TYPE: DNA
<213> ORGANISM: Artificial Sequence
<220> FEATURE:
<223> OTHER INFORMATION: primer

<400> SEQUENCE: 53
gcaagccctc acgtagcgaa gcaggatgag aagcaggtag                                  40

<210> SEQ ID NO 54
<211> LENGTH: 45
<212> TYPE: DNA
<213> ORGANISM: Artificial Sequence
<220> FEATURE:
<223> OTHER INFORMATION: primer

<400> SEQUENCE: 54
gcaagccctc acgtagcgaa cctgacatct aaataatctg tggtg                            45
```

```
<210> SEQ ID NO 55
<211> LENGTH: 43
<212> TYPE: DNA
<213> ORGANISM: Artificial Sequence
<220> FEATURE:
<223> OTHER INFORMATION: probe

<400> SEQUENCE: 55
gaccggtgca ccaatgaaag aacccctcca caatgaaaag cct            43

<210> SEQ ID NO 56
<211> LENGTH: 43
<212> TYPE: DNA
<213> ORGANISM: Artificial Sequence
<220> FEATURE:
<223> OTHER INFORMATION: primer

<400> SEQUENCE: 56
gcaagccctc acgtagcgaa attctacttg aagcgttctg tga            43

<210> SEQ ID NO 57
<211> LENGTH: 41
<212> TYPE: DNA
<213> ORGANISM: Artificial Sequence
<220> FEATURE:
<223> OTHER INFORMATION: primer

<400> SEQUENCE: 57
gcaagccctc acgtagcgaa caaccactgc caaaactttc a              41

<210> SEQ ID NO 58
<211> LENGTH: 41
<212> TYPE: DNA
<213> ORGANISM: Artificial Sequence
<220> FEATURE:
<223> OTHER INFORMATION: probe

<400> SEQUENCE: 58
cccacctccg accacccaag acaaaacacc tactttccac t              41

<210> SEQ ID NO 59
<211> LENGTH: 35
<212> TYPE: DNA
<213> ORGANISM: Artificial Sequence
<220> FEATURE:
<223> OTHER INFORMATION: probe

<400> SEQUENCE: 59
gctgcaaaaa actcaacgat gtggaagtca gcagc                     35

<210> SEQ ID NO 60
<211> LENGTH: 43
<212> TYPE: DNA
<213> ORGANISM: Artificial Sequence
<220> FEATURE:
<223> OTHER INFORMATION: primer

<400> SEQUENCE: 60
gcaagccctc acgtagcgaa agctcagaga aacttacaac act            43

<210> SEQ ID NO 61
<211> LENGTH: 43
<212> TYPE: DNA
<213> ORGANISM: Artificial Sequence
<220> FEATURE:
<223> OTHER INFORMATION: primer
```

<400> SEQUENCE: 61
gcaagccctc acgtagcgaa tgcatttgaa tgtgtagtgg aga         43

<210> SEQ ID NO 62
<211> LENGTH: 47
<212> TYPE: DNA
<213> ORGANISM: Artificial Sequence
<220> FEATURE:
<223> OTHER INFORMATION: probe

<400> SEQUENCE: 62
gctgagtttt ttgggtggta cagagatatt tatgacggat cccaaca     47

<210> SEQ ID NO 63
<211> LENGTH: 43
<212> TYPE: DNA
<213> ORGANISM: Artificial Sequence
<220> FEATURE:
<223> OTHER INFORMATION: primer

<400> SEQUENCE: 63
gcaagccctc acgtagcgaa tttgcaccag gattaagtga aga         43

<210> SEQ ID NO 64
<211> LENGTH: 42
<212> TYPE: DNA
<213> ORGANISM: Artificial Sequence
<220> FEATURE:
<223> OTHER INFORMATION: primer

<400> SEQUENCE: 64
gcaagccctc acgtagcgaa gtcagatgta agattgatgc ca          42

<210> SEQ ID NO 65
<211> LENGTH: 37
<212> TYPE: DNA
<213> ORGANISM: Artificial Sequence
<220> FEATURE:
<223> OTHER INFORMATION: probe

<400> SEQUENCE: 65
atcgttgagt tggttcctcc agagccagga tgtaacc                37

<210> SEQ ID NO 66
<211> LENGTH: 44
<212> TYPE: DNA
<213> ORGANISM: Artificial Sequence
<220> FEATURE:
<223> OTHER INFORMATION: primer

<400> SEQUENCE: 66
gcaagccctc acgtagcgaa gcaaaacatt gggaatatct tgga        44

<210> SEQ ID NO 67
<211> LENGTH: 45
<212> TYPE: DNA
<213> ORGANISM: Artificial Sequence
<220> FEATURE:
<223> OTHER INFORMATION: primer

<400> SEQUENCE: 67
gcaagccctc acgtagcgaa tacaggttat ccacatttct tatct       45

<210> SEQ ID NO 68
<211> LENGTH: 49

```
<212> TYPE: DNA
<213> ORGANISM: Artificial Sequence
<220> FEATURE:
<223> OTHER INFORMATION: probe

<400> SEQUENCE: 68
ttccacatcg tcgttgtaat agcagaaggt aggagatcac taaagtggc          49

<210> SEQ ID NO 69
<211> LENGTH: 51
<212> TYPE: DNA
<213> ORGANISM: Artificial Sequence
<220> FEATURE:
<223> OTHER INFORMATION: probe

<400> SEQUENCE: 69
ccggcgggga gggaccgtcg tggcaggagg agcagctcac caggccgccg g        51

<210> SEQ ID NO 70
<211> LENGTH: 43
<212> TYPE: DNA
<213> ORGANISM: Artificial Sequence
<220> FEATURE:
<223> OTHER INFORMATION: primer

<400> SEQUENCE: 70
gcaagccctc acgtagcgaa ttttgtactt cctggaggtt tag                 43

<210> SEQ ID NO 71
<211> LENGTH: 42
<212> TYPE: DNA
<213> ORGANISM: Artificial Sequence
<220> FEATURE:
<223> OTHER INFORMATION: primer

<400> SEQUENCE: 71
gcaagccctc acgtagcgaa ccaatctcag tttcatccat ct                  42

<210> SEQ ID NO 72
<211> LENGTH: 46
<212> TYPE: DNA
<213> ORGANISM: Artificial Sequence
<220> FEATURE:
<223> OTHER INFORMATION: probe

<400> SEQUENCE: 72
ccacgacggt ctggtcattc ggggataaat gggggagaaa tttcca              46

<210> SEQ ID NO 73
<211> LENGTH: 45
<212> TYPE: DNA
<213> ORGANISM: Artificial Sequence
<220> FEATURE:
<223> OTHER INFORMATION: primer

<400> SEQUENCE: 73
gcaagccctc acgtagcgaa gtgtgtttgt ttttgttttt gtgac               45

<210> SEQ ID NO 74
<211> LENGTH: 43
<212> TYPE: DNA
<213> ORGANISM: Artificial Sequence
<220> FEATURE:
<223> OTHER INFORMATION: primer

<400> SEQUENCE: 74
```

```
gcaagccctc acgtagcgaa caggaaatct ttctaagtgg aca                43

<210> SEQ ID NO 75
<211> LENGTH: 42
<212> TYPE: DNA
<213> ORGANISM: Artificial Sequence
<220> FEATURE:
<223> OTHER INFORMATION: probe

<400> SEQUENCE: 75
ctcctgccac gaggagccat gtgcagaaaa attcactgat gc                 42

<210> SEQ ID NO 76
<211> LENGTH: 38
<212> TYPE: DNA
<213> ORGANISM: Artificial Sequence
<220> FEATURE:
<223> OTHER INFORMATION: primer

<400> SEQUENCE: 76
gcaagccctc acgtagcgaa ttacaggatt cggcgtga                      38

<210> SEQ ID NO 77
<211> LENGTH: 38
<212> TYPE: DNA
<213> ORGANISM: Artificial Sequence
<220> FEATURE:
<223> OTHER INFORMATION: primer

<400> SEQUENCE: 77
gcaagccctc acgtagcgaa gccacgtcct ttggtagt                      38

<210> SEQ ID NO 78
<211> LENGTH: 38
<212> TYPE: DNA
<213> ORGANISM: Artificial Sequence
<220> FEATURE:
<223> OTHER INFORMATION: probe

<400> SEQUENCE: 78
cctggtgagc tcagaacgtc tggcggaatc caaacact                      38
```